(12) United States Patent
Hoefman et al.

(10) Patent No.: US 11,008,393 B2
(45) Date of Patent: May 18, 2021

(54) PHARMACEUTICAL COMPOSITIONS COMPRISING A POLYPEPTIDE THAT BINDS TO IL-6

(71) Applicant: Ablynx N.V., Ghent-Zwijnaarde (BE)

(72) Inventors: Sven Hoefman, Kortrijk (BE); Maria-Laura Sargentini-Maier, Brussels (BE); Katrien Van Beneden, Scheldewindeke (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 62 days.

(21) Appl. No.: 16/143,580

(22) Filed: Sep. 27, 2018

(65) Prior Publication Data

US 2019/0119392 A1    Apr. 25, 2019

Related U.S. Application Data

(62) Division of application No. 14/904,864, filed as application No. PCT/EP2015/074364 on Oct. 21, 2015, now Pat. No. 10,118,967.

(60) Provisional application No. 62/066,562, filed on Oct. 21, 2014.

(51) Int. Cl.
| | |
|---|---|
| C07K 16/28 | (2006.01) |
| A61K 31/519 | (2006.01) |
| A61K 39/395 | (2006.01) |
| C07K 16/18 | (2006.01) |
| A61K 39/00 | (2006.01) |

(52) U.S. Cl.
CPC ........ *C07K 16/2866* (2013.01); *A61K 31/519* (2013.01); *A61K 39/3955* (2013.01); *C07K 16/18* (2013.01); *A61K 2039/505* (2013.01); *A61K 2039/54* (2013.01); *A61K 2039/545* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
CPC ................................................ C07K 16/2866
See application file for complete search history.

(56) References Cited

U.S. PATENT DOCUMENTS

| | | | |
|---|---|---|---|
| 5,116,964 A | 5/1992 | Capon et al. | |
| 5,888,510 A | 3/1999 | Kishimoto et al. | |
| 6,261,560 B1 | 7/2001 | Tsujinaka et al. | |
| 6,664,374 B1 | 12/2003 | Saxinger | |
| 8,629,244 B2 | 1/2014 | Kolkman et al. | |
| 8,748,581 B2 | 6/2014 | Beirnaert et al. | |
| 8,962,805 B2 | 2/2015 | Beirnaert et al. | |
| 9,181,350 B2 | 11/2015 | Beirnaert et al. | |
| 9,273,150 B2 | 3/2016 | Beirnaert et al. | |
| 9,605,072 B2 | 3/2017 | Kolkman et al. | |
| 9,611,326 B2 | 4/2017 | Kolkman et al. | |
| 9,617,341 B2 | 4/2017 | Kolkman et al. | |
| 10,118,967 B2 | 11/2018 | Hoefman et al. | |
| 10,138,302 B2 | 11/2018 | Holz et al. | |
| 10,392,440 B2 | 8/2019 | Beirnaert et al. | |
| 10,618,964 B2 | 4/2020 | Compernolle et al. | |
| 10,618,966 B2 | 4/2020 | Kolkman et al. | |
| 2005/0089932 A1 | 4/2005 | Kolkman et al. | |
| 2005/0142635 A1 | 6/2005 | Tsuchiya et al. | |
| 2007/0036785 A1 | 2/2007 | Kishimoto et al. | |
| 2007/0280945 A1 | 12/2007 | Stevens et al. | |
| 2010/0215664 A1 | 8/2010 | Kolkman et al. | |
| 2011/0243954 A1 | 10/2011 | Revets et al. | |
| 2012/0077731 A1 | 3/2012 | Beirnaert et al. | |
| 2012/0171209 A1 | 7/2012 | Compernolle et al. | |
| 2012/0244158 A1 | 9/2012 | Brige et al. | |
| 2014/0212417 A1 | 7/2014 | Holz et al. | |
| 2014/0221623 A1 | 8/2014 | Kolkman et al. | |
| 2014/0329278 A1 | 11/2014 | Beirnaert et al. | |
| 2014/0343257 A1 | 11/2014 | Beirnaert et al. | |
| 2014/0348830 A1 | 11/2014 | Beirnaert et al. | |
| 2014/0349342 A1 | 11/2014 | Kolkman et al. | |
| 2015/0037338 A1 | 2/2015 | Beirnaert et al. | |
| 2015/0050268 A9 | 2/2015 | Holz et al. | |
| 2016/0326252 A1 | 11/2016 | Hoefman et al. | |
| 2016/0333099 A1 | 11/2016 | Beirnaert et al. | |
| 2018/0016342 A1 | 1/2018 | Kolkman et al. | |
| 2019/0119393 A1 | 4/2019 | Holz et al. | |

FOREIGN PATENT DOCUMENTS

| | | |
|---|---|---|
| CN | 1535728 A | 10/2004 |
| EP | 0 257 406 A2 | 3/1988 |
| EP | 0 312 996 A2 | 4/1989 |
| EP | 0 325 474 A2 | 7/1989 |
| EP | 0 409 607 A2 | 1/1991 |
| EP | 0 411 946 A2 | 2/1991 |
| EP | 0 527 809 A1 | 2/1993 |

(Continued)

OTHER PUBLICATIONS

No Author Listed], Ablynx initiates Phase I bioavailability study with subcutaneous formulation of its anti-IL-6R Nanobody partnered with AbbVie. GlobeNewswire. Apr. 23, 2014, p. 3pp.

No Author Listed], Ablynx Reports Positive Phase I Data for ALX-0061 in Rheumatoid Arthritis. Press release. Ablynx. Ghent, Belgium. Nov. 30, 2011.

No Author Listed], Ablynx' anti-IL-6R Nanobody partnered with AbbVie demonstrates a bioavailability of more than 80% after subcutaneous injection. GlobeNewswire. Oct. 23, 2014; p. 3pp.

(Continued)

*Primary Examiner* — Prema M Mertz
(74) *Attorney, Agent, or Firm* — Wolf, Greenfield & Sacks, P.C.

(57) ABSTRACT

Methods are provided for the treatment of IL-6R related diseases. More specifically, specific dose regimens and pre-filled syringes are provided for subcutaneous administration, to subjects suffering an IL-6R related disease, of immunoglobulin single variable domains that bind IL-6R.

7 Claims, 6 Drawing Sheets

Specification includes a Sequence Listing.

(56) References Cited

FOREIGN PATENT DOCUMENTS

| | | |
|---|---|---|
| EP | 0 572 118 A1 | 12/1993 |
| EP | 0 628 639 B1 | 12/1994 |
| EP | 0 409 607 B1 | 10/1996 |
| JP | 2000/500644 A | 1/2000 |
| WO | WO 1997/13781 A2 | 4/1997 |
| WO | WO 2005/003345 A2 | 1/2005 |
| WO | WO 2006/023144 A2 | 3/2006 |
| WO | WO 2006/079372 A1 | 8/2006 |
| WO | WO 2007/042289 A2 | 4/2007 |
| WO | WO 2007/104529 A2 | 9/2007 |
| WO | WO 2008/020079 A1 | 2/2008 |
| WO | WO 2008/071685 A1 | 6/2008 |
| WO | WO 2008/074840 A2 | 6/2008 |
| WO | WO 2008/077945 A2 | 7/2008 |
| WO | WO 2009/004065 A2 | 1/2009 |
| WO | WO 2009/010539 A2 | 1/2009 |
| WO | WO 2009/095489 A2 | 8/2009 |
| WO | WO 2010/100135 A1 | 9/2010 |
| WO | WO 2010/115995 A2 | 10/2010 |
| WO | WO 2010/115998 A2 | 10/2010 |
| WO | WO 2011/026945 A1 | 3/2011 |
| WO | WO 2011/026948 A1 | 3/2011 |
| WO | WO 2011/098518 A2 | 8/2011 |
| WO | WO 2012/064627 A2 | 5/2012 |
| WO | WO 2013/041722 A1 | 3/2013 |
| WO | WO 2016/062766 A1 | 4/2016 |

OTHER PUBLICATIONS

No Author Listed], Ablynx's anti-IL-6R Nanobody, ALX-0061, shows excellent 24 week safety and efficacy results in a phase II clinical trial in rheumatoid arthritis. Feb. 13, 2013. Ghent, Belgium.
No Author Listed], Compelling topline results from the Phase IIb combination therapy study of vobarilizumab, ALX-0061 (anti-IL-6R), in patients with moderate to severe RA. Presentation by Ablynx, Aug. 9, 2016.
No Author Listed], Topline results from the Phase IIb monotherapy study of vobarilizumab. ALX-0061 (anti-IL-6R), in patients with moderate to severe RA. Presentation by Ablynx, Jul. 7, 2016.
Ali et al., Improvements in the cell-free production of functional antibodies using cell extract from protease-deficient *Escherichia coli* mutant. J Biosci Bioeng. Feb. 2005;99(2):181-6.
Atreya et al., Blockade of interleukin 6 trans signaling suppresses T-cell resistance against apoptosis in chronic intestinal inflammation: evidence in Crohn disease and experimental colitis in vivo. Nat Med. May 2000;6(5):583-8. Erratum in: Nat Med. Nov. 2010;16(11):1341.
Bataille et al., Biologic effects of anti-interleukin-6 murine monoclonal antibody in advanced multiple myeloma. Blood. Jul. 15, 1995;86(2):685-91.
Beck et al., Brief report: alleviation of systemic manifestations of Castleman's disease by monoclonal anti-interleukin-6 antibody. N Engl J Med. Mar. 3, 1994;330(9):602-5.
Becker et al., TGF-beta suppresses tumor progression in colon cancer by inhibition of IL-6 trans-signaling. Immunity. Oct. 2004;21(4):491-501.
Boulanger et al., Hexameric structure and assembly of the interleukin-6/IL-6 alpha-receptor/gp130 complex. Science. Jun. 27, 2003;300(5628):2101-4. Erratum in: Science. Aug. 15, 2003;301(5635):918.
Brorson et al., Mutational analysis of avidity and fine specificity of anti-levan antibodies. J Immunol. Dec. 15, 1999;163(12):6694-701.
Brummell et al., Probing the combining site of an anti-carbohydrate antibody by saturation-mutagenesis: role of the heavy-chain CDR3 residues. Biochemistry. Feb. 2, 1993;32(4):1180-7.
Campbell et al., Essential role for interferon-gamma and interleukin-6 in autoimmune insulin-dependent diabetes in NOD/Wehi mice. J Clin Invest. Feb. 1991;87(2):739-42.
Choy et al., Therapeutic benefit of blocking interleukin-6 activity with an anti-interleukin-6 receptor monoclonal antibody in rheumatoid arthritis: a randomized, double-blind, placebo-controlled, dose-escalation trial. Arthritis Rheum. Dec. 2002;46(12):3143-50.
Colman, Effects of amino acid sequence changes on antibody-antigen interactions. Res Immunol. Jan. 1994;145(1):33-6.
David et al., A study of the structural correlates of affinity maturation: antibody affinity as a function of chemical interactions, structural plasticity and stability. Mol Immunol. Feb. 2007;44(6):1342-51. Epub Jul. 18, 2006.
De Bruyn et al., Anti-IL-6 receptor Nanobody (ALX-0061) seamless "first-in-human" phase I/II POC study in patients with active RA on stable MTX treatment. Arthritis & Rheumatism. Oct. 1, 2012; 64(10) Suppl.: S561.
Decanniere et al., A single-domain antibody fragment in complex with RNase A: noncanonical loop structures and nanomolar affinity using two CDR loops. Structure. Apr. 15, 1999;7(4):361-70.
Desgeorges et al., Concentrations and origins of soluble interleukin 6 receptor-alpha in serum and synovial fluid. J Rheumatol. Aug. 1997;24(8):1510-6.
Desmyter et al., Antigen specificity and high affinity binding provided by one single loop of a camel single-domain antibody. J Biol Chem. Jul. 13, 2001;276(28):26285-90. Epub May 7, 2001.
Desmyter et al., Crystal structure of a camel single-domain VH antibody fragment in complex with lysozyme. Nat Struct Biol. Sep. 1996;3(9):803-11.
Doganci et al., The IL-6R alpha chain controls lung CD4+CD25+ Treg development and function during allergic airway inflammation in vivo. J Clin Invest. Feb. 2005;115(2):313-25. Erratum in: J Clin Invest. May 2005;115(5):1388. Lehr, Hans A [added].
Emilie et al., Cytokines in HIV infection. Int J Immunopharmacol. May-Jun. 1994;16(5-6):391-6.
Emilie et al., Administration of an anti-interleukin-6 monoclonal antibody to patients with acquired immunodeficiency syndrome and lymphoma: effect on lymphoma growth and on B clinical symptoms. Blood. Oct. 15, 1994;84(8):2472-9.
Frankel et al., Characterization of diphtheria fusion proteins targeted to the human interleukin-3 receptor. Protein Eng. Aug. 2000;13(8):575-81.
Frey et al., Population pharmacokinetic analysis of tocilizumab in patients with rheumatoid arthritis. J Clin Pharmacol. Jul. 2010;50(7):754-66. doi: 10.1177/0091270009350623. Epub Jan. 23, 2010.
Gaillard et al., Identification of a novel antigenic structure of the human receptor for interleukin-6 involved in the interaction with the glycoprotein 130 chain. Immunology. Sep. 1996;89(1):135-41.
Gratacos et al., Serum cytokines (IL-6, TNF-alpha, IL-1 beta and IFN-gamma) in ankylosing spondylitis: a close correlation between serum IL-6 and disease activity and severity. Br J Rheumatol. Oct. 1994;33(10):927-31.
Grau et al., Interleukin 6 production in experimental cerebral malaria: modulation by anticytokine antibodies and possible role in hypergammaglobulinemia. J Exp Med. Nov. 1, 1990;172(5):1505-8.
Grogg et al., HIV infection and lymphoma. J Clin Pathol. Dec. 2007;60(12):1365-72.
Hibi et al., Molecular cloning and expression of an IL-6 signal transducer, gp130. Cell. Dec. 21, 1990;63(6):1149-57.
Hinton et al., An engineered human IgG1 antibody with longer serum half-life. J Immunol. Jan. 1, 2006;176(1):346-56.
Hirano et al., Interleukin 6 and its receptor in the immune response and hematopoiesis. Int J Cell Cloning. Jan. 1990;8 Suppl 1:155-66; discussion 166-7.
Hirano et al., Biological and clinical aspects of interleukin 6. Immunol Today. Dec. 1990;11(12):443-9.
Hirano et al., Purification to homogeneity and characterization of human B-cell differentiation factor (BCDF or BSFp-2). Proc Natl Acad Sci U S A. Aug. 1985;82(16):5490-4.
Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
Holz et al., Twenty-four weeks of treatment with a novel anti-IL-6 receptor Nanobody(R) (ALX-0061) resulted in 84% ACR20 improvement and 58% DAS28 remission in a phase I/II study in RA. Annals

(56) References Cited

OTHER PUBLICATIONS of the Rheumatic Diseases. Jun. 2013; 72(suppl 3):64. Annual European Congress of Rheumatology (EULAR). Madrid, Spain. Jun. 12-15, 2013.
Holz et al.: Developing Nanobodies: from bench to bedside. Internet citation. Jun. 24, 2008. pp. 1-37. Retrieved from the internet http://www.pda.org/Presentation/2008/PDAEBEDublin/holzjosefin. asp.
Hosea et al., Prediction of human pharmacokinetics from preclinical information: comparative accuracy of quantitative prediction approaches. J Clin Pharmacol. May 2009;49(5):513-33. doi:10.1177/0091270009333209. Epub Mar. 19, 2009.
Houdebine, Production of pharmaceutical proteins by transgenic animals. Comp Immunol Microbiol Infect Dis. Mar. 2009;32(2):107-21. doi: 10.1016/j.cimid.2007.11.005. Epub Feb. 19, 2008.
Imazeki et al., IL-6 functions in cynomolgus monkeys blocked by a humanized antibody to human IL-6 receptor. Int J Immunopharmacol. Jul. 1998;20(7):345-57.
Ishihara et al., IL-6 in autoimmune disease and chronic inflammatory proliferative disease. Cytokine Growth Factor Rev. Aug.-Oct. 2002;13(4-5):357-68.
Ishihara et al., Molecular basis of the cell specificity of cytokine action. Biochim Biophys Acta. Nov. 11, 2002;1592(3):281-96.
Ito et al., A pilot randomized trial of a human anti-interleukin-6 receptor monoclonal antibody in active Crohn's disease. Gastroenterology. 2004;126:989-96.
Jang et al., Pharmacokinetic/pharmacodynamic (PK/PD) modeling and trial simulations to guide dose selection with CNTO 328, a chimeric anti-IL-6 monoclonal antibody (Mab), in patients with renal cell carcinoma (RCC). Journal of Clinical Oncology, 2004 ASCO Annual Meeting Proceedings (Post-Meeting Edition). 2004;22(14S, Jul. 15 Supplement):2608. Abstract.
Jilka et al., Increased osteoclast development after estrogen loss: mediation by interleukin-6. Science. Jul. 3, 1992;257(5066):88-91.
Jones et al., Replacing the complementarity-determining regions in a human antibody with those from a mouse. Nature. May 29-Jun. 4, 1986;321(6069):522-5.
Jones et al., Therapeutic strategies for the clinical blockade of IL 6/gp130 signaling. J Clin Invest. Sep. 2011;121(9):3375-83. doi: 10.1172/JCI57158. Epub Sep. 1, 2011.
Kalai et al., Participation of two Ser-Ser-Phe-Tyr repeats in interleukin-6 (IL-6)-binding sites of the human IL-6 receptor. Eur J Biochem. Jun. 15, 1996;238(3):714-23.
Kaufman et al., Transgenic analysis of a 100-kb human beta-globin cluster-containing DNA fragment propagated as a bacterial artificial chromosome. Blood. Nov. 1, 1999;94(9):3178-84. Erratum in: Blood Feb. 1, 2000;95(3):744.
Kipriyanov, Generation of bispecific and tandem diabodies. Methods Mol Biol. 2009;562:177-93.
Klein et al., Murine anti-interleukin-6 monoclonal antibody therapy for a patient with plasma cell leukemia. Blood. Sep. 1, 1991;78(5):1198-204.
Ko et al., Production of antibodies in plants: approaches and perspectives. Curr Top Microbiol Immunol. 2009;332:55-78. doi: 10.1007/978-3-540-70868-1_4.
Kobayashi et al., Tryptophan H33 plays an important role in pyrimidine (6-4) pyrimidone photoproduct binding by a high-affinity antibody. Protein Eng. Oct. 1999;12(10):879-84.
Lederman et al., A single amino acid substitution in a common African allele of the CD4 molecule ablates binding of the monoclonal antibody, OKT4. Mol Immunol. Nov. 1991;28(11):1171-81.
Levi et al., Effect of tocilizumab exposure on IL-6 and IL-6 receptor levels in patients with rheumatoid arthritis: graphical analysis of pooled data from four phase 3 clinical trials. Ann Rheum Dis. 2008;67(Suppl II):192. Abstract THU0176.
Levi et al., Effect of tocilizumab exposure on IL-6 and IL-6 receptor levels in patients with rheumatoid arthritis: graphical analysis of pooled data from four phase 3 clinical trials. Presentation EULAR conference. Jun. 11-14, 2008.
Levi et al., Reduction in inflammatory biomarkers with increasing exposure to the IL-6 inhibitor, tocilizumab, in patients with rheumatoid arthritis: Graphical analysis of pooled data. Ann Rheum Dis. 2008;67(Suppl II):192. Abstract THU0177.
Li et al., beta-Endorphin omission analogs: dissociation of immunoreactivity from other biological activities. Proc Natl Acad Sci U S A. Jun. 1980;77(6):3211-4.
Liautard et al., Epitope analysis of human IL-6 receptor gp80 molecule with monoclonal antibodies. Eur Cytokine Netw. May-Jun. 1994;5(3):293-300.
Lu et al., Acquired antagonistic activity of a bispecific diabody directed against two different epitopes on vascular endothelial growth factor receptor 2. J Immunol Methods. Nov. 19, 1999;230(1-2):159-71.
Martin, Protein Sequence and Structure Analysis of Antibody Variable Domains. In: Antibody Engineering Lab Manual (Ed.: Duebel, Kontermann, Springer-Verlag, Heidelberg). Chapter 3. 2010. 33-51.
Merk et al., Cell-free expression of two single-chain monoclonal antibodies against lysozyme: effect of domain arrangement on the expression. J Biochem. Feb. 1999;125(2):328-33.
Mihara et al., Humanized antibody to human interleukin-6 receptor inhibits the development of collagen arthritis in cynomolgus monkeys. Clin Immunol. Mar. 2001;98(3):319-26.
Murakami et al., The value of blocking IL-6 outside of rheumatoid arthritis: current perspective. Curr Opin Rheumatol. May 2011;23(3):273-7. doi: 10.1097/BOR.0b013e3283456797.
Muyldermans et al., Unique single-domain antigen binding fragments derived from naturally occurring camel heavy-chain antibodies. J Mol Recognit. Mar.-Apr. 1999;12(2):131-40.
Nakashima et al., Drug delivery options to increase patient adherence and satisfaction in the management of rheumatoid arthritis—focus on subcutaneous tocilizumab. Drug Des Devel Ther. Jul. 4, 2014;8:913-9. doi: 10.2147/DDDT.S52099. eCollection 2014.
Neurath et al., IL-6 signaling in autoimmunity, chronic inflammation and inflammation-associated cancer. Cytokine Growth Factor Rev. Apr. 2011;22(2):83-9. doi: 10.1016/j.cytogfr.2011.02.003. Epub Mar. 5, 2011.
Nishimoto et al., Humanized anti-interleukin-6 receptor antibody treatment of multicentric Castleman disease. Blood. Oct. 15, 2005;106(8):2627-32. Epub Jul. 5, 2005.
Nishimoto et al., Interleukin 6: from bench to bedside. Nat Clin Pract Rheumatol. Nov. 2006;2(11):619-26. Erratum in: Nat Clin Pract Rheumatol. Dec. 2006;2(12):691.
Nishimoto et al., Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood. Nov. 15, 2008;112(10):3959-64. doi: 10.1182/blood-2008-05-155846. Epub Sep. 10, 2008.
Nishimoto et al., Toxicity, pharmacokinetics, and dose-finding study of repetitive treatment with the humanized anti-interleukin 6 receptor antibody MRA in rheumatoid arthritis. Phase I/II clinical study. J Rheumatol. Jul. 2003;30(7):1426-35.
Nishimoto et al., Treatment of rheumatoid arthritis with humanized anti-interleukin-6 receptor antibody: a multicenter, double-blind, placebo-controlled trial. Arthritis Rheum. Jun. 2004;50(6):1761-9.
Nishimoto, Interleukin-6 as a therapeutic target in candidate inflammatory diseases. Clin Pharmacol Ther. Apr. 2010;87(4):483-7. doi: 10.1038/clpt.2009.313. Epub Feb. 24, 2010.
Nishimoto, Usefulness and problems in rheumatoid arthritis. CHIRYO-GAKU. 2002;36(12):1264-1267.
Nowell et al., Soluble IL-6 receptor governs IL-6 activity in experimental arthritis: blockade of arthritis severity by soluble glycoprotein 130. J Immunol. Sep. 15, 2003;171(6):3202-9.
Ogata et al., Advances in interleukin-6 therapy. Jpn J Clin Pathol. Apr. 1999;47(4):321-6.
Paul, Fundamental immunology. 3rd Edition. 1993:292-295.
Prabhakar et al., Correlation of serum CNTO 328-Anti IL-6 monoclonal antibody (Mab) concentrations and biomarker expression in renal cell carcinoma (RCC) patients. Journal of Clinical Oncology, 2004 ASCO Annual Meeting Proceedings (Post-Meeting Edition). 2004;22(14S, Jul. 15 Supplement):2560. Abstract.

(56) References Cited

OTHER PUBLICATIONS

Rajpal et al., A general method for greatly improving the affinity of antibodies by using combinatorial libraries. Proc Natl Acad Sci U S A. Jun. 14, 2005;102(24):8466-71. Epub Jun. 6, 2005.

Revets et al., Nanobodies as novel agents for cancer therapy. Expert Opin Biol Ther. Jan. 2005;5(1):111-24.

Richter et al., Mechanistic determinants of biotherapeutics absorption following SC administration. AAPS J. Sep. 2012;14(3):559-70. doi: 10.1208/s12248-012-9367-0. Epub May 23, 2012.

Richter et al., Subcutaneous absorption of biotherapeutics: knowns and unknowns. Drug Metab Dispos. Nov. 2014;42(11):1881-9. doi: 10.1124/dmd.114.059238. Epub Aug. 6, 2014.

Riechmann et al., Single domain antibodies: comparison of camel VH and camelised human VH domains. J Immunol Methods. Dec. 10, 1999;231(1-2):25-38.

Riechmann, Rearrangement of the former VL interface in the solution structure of a camelised, single antibody VH domain. J Mol Biol. Jun. 28, 1996;259(5):957-69.

Robert et al., Tumor targeting with newly designed biparatopic antibodies directed against two different epitopes of the carcinoembryonic antigen (CEA). Int J Cancer. Apr. 12, 1999;81(2):285-91.

Roitt et al., Immunology. 5th edition. 1998;80-81, 107. (translation of 110-111, 150 from Russian-language version of Roitt et al., Immunology).

Roodman et al., Interleukin 6. A potential autocrine/paracrine factor in Paget's disease of bone. J Clin Invest. Jan. 1992;89(1):46-52.

Roodman et al., Interleukin-6: an osteotropic factor? J Bone Miner Res. May 1992;7(5):475-8.

Roovers et al., Efficient inhibition of EGFR signaling and of tumour growth by antagonistic anti-EFGR Nanobodies. Cancer Immunol Immunother. Mar. 2007;56(3):303-317.

Roovers et al., Nanobodies in therapeutic applications. Curr Opin Mol Ther. Aug. 2007;9(4):327-35.

Rose-John et al., Interleukin-6 biology is coordinated by membrane-bound and soluble receptors: role in inflammation and cancer. J Leukoc Biol. Aug. 2006;80(2):227-36. Epub May 17, 2006.

Rudikoff et al., Single amino acid substitution altering antigen-binding specificity. Proc Natl Acad Sci U S A. Mar. 1982;79(6):1979-83.

Saito et al., Preparation of monoclonal antibodies against the IL-6 signal transducer, gp130, that can inhibit IL-6-mediated functions. J Immunol Methods. Aug. 9, 1993;163(2):217-23.

Sato et al., Reshaping a human antibody to inhibit the interleukin 6-dependent tumor cell growth. Cancer Res. Feb. 15, 1993;53(4):851-6.

Scheller et al., Interleukin-6 and its receptor: from bench to bedside. Med Microbiol Immunol. Dec. 2006;195(4):173-83. Epub May 31, 2006.

Schmitt et al., Disease-drug-drug interaction involving tocilizumab and simvastatin in patients with rheumatoid arthritis. Clin Pharmacol Ther. May 2011;89(5):735-40. doi: 10.1038/clpt.2011.35. Epub Mar. 23, 2011. Erratum in: Clin Pharmacol Ther. Sep. 2011;90(3):479.

Schoels et al., Blocking the effects of interleukin-6 in rheumatoid arthritis and other inflammatory rheumatic diseases: systematic literature review and meta-analysis informing a consensus statement. Ann Rheum Dis. Apr. 2013;72(4):583-9. doi: 10.1136/annrheumdis-2012-202470. Epub Nov. 10, 2012.

Shinkura et al., In vivo blocking effects of a humanized antibody to human interleukin-6 receptor on interleukin-6 function in primates. Anticancer Res. Mar.-Apr. 1998;18(2A):1217-21.

Smolen et al., OPTION Investigators. Effect of interleukin-6 receptor inhibition with tocilizumab in patients with rheumatoid arthritis (OPTION study): a double-blind, placebo-controlled, randomised trial. Lancet. Mar. 22, 2008;371(9617):987-97. doi: 10.1016/S0140-6736(08)60453-5.

Spinelli et al., The crystal structure of a llama heavy chain variable domain. Nat Struct Biol. Sep. 1996;3(9):752-7.

Starnes et al., Anti-IL-6 monoclonal antibodies protect against lethal Escherichia coli infection and lethal tumor necrosis factor-alpha challenge in mice [retraction of Starnes HF Jr, Pearce MK, Tewari A, Yim JH, Zou JC, Abrams JS. In: J Immunol. Dec. 15, 1990;145(12):4185-91]. J Immunol. Mar. 15, 1992;148(6):1968.

Strassman et al., Evidence for the involvement of interleukin 6 in experimental cancer cachexia. J Clin Invest. May 1992;89:1681-1684.

Taga et al., Interleukin-6 triggers the association of its receptor with a possible signal transducer, gp130. Cell. Aug. 11, 1989;58(3):573-81.

Tanaka et al., Targeting interleukin-6: all the way to treat autoimmune and inflammatory diseases. Int J Biol Sci. 2012;8(9):1227-36. doi: 10.7150/ijbs.4666. Epub Oct. 24, 2012.

Tanaka et al., Therapeutic targeting of the interleukin-6 receptor. Annu Rev Pharmacol Toxicol. 2012;52:199-219. doi:10.1146/annurev-pharmtox-010611-134715. Epub Sep. 9, 2011

Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi: 10.1158/1535-7163.MCT-07-2384.

Trikha et al., Targeted anti-interleukin-6 monoclonal antibody therapy for cancer: a review of the rationale and clinical evidence. Clin Cancer Res. Oct. 15, 2003;9(13):4653-65.

Usón et al., Soluble interleukin 6 (IL-6) receptor and IL-6 levels in serum and synovial fluid of patients with different arthropathies. J Rheumatol. Nov. 1997;24(11):2069-75.

Van Roy et al., ALX-0061, an anti-IL-6R Nanobody® for therapeutic use in rheumatoid arthritis, demonstrates in vitro a different biological activity profile as compared to tocilizumab. [Online] (Jan. 2014) ResearchGate. Retrieved on Jul. 18, 2019. Retrieved from: https://www.researchgate.net/profile/Maarten_Van_Roy/publication/275562632_FRI0021_Alx-0061_an_anti-ILr_nanobodyR_for_therapeutic_use_in_rheumatoid_arthritis_demonstrates_in_vitro_a_differential_biological_activity_profile_as_compared_to_tocilizumab/links/572ca03d08ae9e18450dgd3f/FRI0021_Alx-0061-an-anti-IL-6r-nanobodyR-for-therapeutic-use-in-rheumatoid-arthritis-demonstrates-in-vitro-a-differential-biological-activity-profile-as-compared-to-tocilizumab.pdf?origin=publiation_detail>. 5 pages. Page 1 is full poster. Pages 2-5 are magnifications of each quadrant.

Van Roy et al., The preclinical pharmacology of the high affinity anti-IL-6R Nanobody® ALX-0061 supports its clinical development in rheumatoid arthritis. Arthritis Res Ther. May 20, 2015;17:135. doi: 10.1186/s13075-015-0651-0.

Vierboom et al., Preclinical evaluation of anti-rheumatic drugs in a non-human primate model of arthritic disease. Drug Discovery Today: Disease Models. 2008; 30(20):e1-7. doi.10.1016/j.ddmod.2008.06.003.

Wang et al., Rapid analysis of gene expression (RAGE) facilitates universal expression profiling. Nucleic Acids Res. Dec. 1, 1999;27(23):4609-18.

Wendling et al., Treatment of severe rheumatoid arthritis by anti-interleukin 6 monoclonal antibody. J Rheumatol. Feb. 1993;20(2):259-62.

Wesolowski et al., Single domain antibodies: promising experimental and therapeutic tools in infection and immunity. Med Microbiol Immunol. Aug. 2009;198(3):157-74. doi: 10.1007/s00430-009-0116-7. Epub Jun. 16, 2009.

Woo et al., Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement. Arthritis Res Ther. 2005;7(6):R1281-8. Epub Sep. 15, 2005.

Yamasaki et al., Cloning and expression of the human interleukin-6 (BSF-2/IFN beta 2) receptor. Science. Aug. 12, 1988;241(4867):825-8.

Yau et al., Affinity maturation of a V(H)H by mutational hotspot randomization. J Immunol Methods. Feb. 2005;297(1-2):213-24. Epub Jan. 20, 2005.

Yokota et al., Phase 2 trials of anti-IL6 receptor antibody (MRA) for systemic onset juvenile idiopathic arthritis. Autoimmune Rev. 2004;3:599-600.

(56) References Cited

OTHER PUBLICATIONS

Zaki et al., CNTO 328, a monoclonal antibody to IL-6, inhibits human tumor-induced cachexia in nude mice. Int J Cancer. Sep. 10, 2004;111(4):592-5.

Zhang et al., Clinical pharmacology of tocilizumab for the treatment of patients with rheumatoid arthritis. Expert Rev Clin Pharmacol. Sep. 2011;4(5):539-58. doi: 10.1586/ecp.11.33.

Zheng et al., Minipig as a potential translatable model for monoclonal antibody pharmacokinetics after intravenous and subcutaneous administration. MAbs. Mar.-Apr. 2012;4(2):243-55. doi: 10.4161/mabs.4.2.19387. Epub Mar. 1, 2012.

PCT/EP2007/058587, Jan. 15, 2008, International Search Report and Written Opinion.

PCT/EP2007/058587, Mar. 5, 2009, International Preliminary Report on Patentability.

PCT/EP2010/054747, Jan. 5, 2011, International Search Report and Written Opinion.

PCT/EP2010/054747, Oct. 20, 2011, International Preliminary Report on Patentability.

PCT/EP2010/054764, Nov. 16, 2010, International Search Report and Written Opinion.

PCT/EP2010/054764, Oct. 20, 2011, International Preliminary Report on Patentability.

PCT/EP2012/068765, Dec. 12, 2012, International Search Report and Written Opinion.

PCT/EP2015/074364, Dec. 18, 2015, International Search Report and Written Opinion.

PCT/EP2015/074364, May 4, 2017, International Preliminary Report on Patentability.

PHARMACEUTICAL COMPOSITIONS COMPRISING A POLYPEPTIDE THAT BINDS TO IL-6

RELATED APPLICATIONS

This application is a divisional of U.S. application Ser. No. 14/904,864, filed Jan. 13, 2016, which is a national stage filing under 35 U.S.C. § 371 of international application PCT/EP2015/074364, filed Oct. 21, 2015, which was published under PCT Article 21(2) in English, and claims the benefit under 35 U.S.C. § 119(e) of U.S. provisional application Ser. No. 62/066,562, filed Oct. 21, 2014, the disclosure of each of which is incorporated by reference herein in its entirety.

FIELD OF THE INVENTION

The present invention provides methods for the treatment of IL-6R related diseases. More specifically, the present invention provides specific dose regimens for subcutaneous administration, to subjects suffering an IL-6R related disease, of immunoglobulin single variable domains that bind IL-6R.

BACKGROUND

IL-6 is a pleiotropic cytokine with a wide range of biological activities. The IL-6 pathway functions through the interaction of IL-6 with its receptor IL-6R. This cytokine-receptor complex interacts with a third partner, the adaptor molecule glycoprotein 130 (gp130), responsible for signal transduction and activation of the cell (Jones et al. 2011, J. Clin. Investig. 121: 3375-83). IL-6R is present not only as a membrane bound form but also as a soluble form. sIL-6R can interact with IL-6 and this complex can activate gp130-positive cells without the presence of membrane-bound (m)IL-6R on the surface of the cells. This process is called trans-signaling and implies that mIL-6R negative cells are also susceptible to activation, with soluble IL-6R acting as an agonist (Jones et al. 2011; Waetzig and Rose-John 2012, Exp. Opinion Therap. Targets, 16: 225-36).

As IL-6 is a pleiotropic cytokine, its function is highly diverse. Many studies revealed that this molecule, by binding to the target IL-6R and gp130, plays a role in the immune, hematopoietic, hepatic, and neuronal systems (Maini 2008, Plenary lecture EULAR conference 2008; Jones et al. 2005, J. Interferon Cytokine Res. 25: 241-253).

Deregulation of IL-6 production is implicated in the pathology of several autoimmune and chronic inflammatory proliferative disease processes (Ishihara and Hirano 2002, Biochim. Biophys. Acta 1592: 281-96). IL-6 overproduction and signaling (and in particular trans-signaling) are involved in various diseases and disorders, such as sepsis (Starnes et al. 1999, J. Immunol. 148: 1968) and various forms of cancer such as multiple myeloma disease (MM), renal cell carcinoma (RCC), plasma cell leukemia (Klein et al. 1991, Blood 78: 1198-204), lymphoma, B-lymphoproliferative disorder (BLPD) and prostate cancer. Non-limiting examples of other diseases caused by excessive IL-6 production or signaling include bone resorption (osteoporosis) (Roodman et al. 1992, J. Bone Miner. Res. 7: 475-8; Jilka et al. 1992, Science 257: 88-91), cachexia (Strassman et al. 1992, J. Clin. Invest. 89: 1681-1684), psoriasis, mesangial proliferative glomerulonephritis, Kaposi's sarcoma, AIDS-related lymphoma (Emilie et al. 1994, Int. J. Immunopharmacol. 16: 391-6), inflammatory diseases and disorder such as rheumatoid arthritis (RA), systemic onset juvenile idiopathic arthritis (JIA), hypergammaglobulinemia (Grau et al. 1990, J. Exp. Med. 172: 1505-8), Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al. 1991, J. Clin. Invest. 87: 739-742).

Rheumatoid arthritis (RA) is a chronic systemic inflammatory autoimmune disease that affects 0.5-1% of the population and is three times more prevalent in women than in men (Emery 2010, Int. J. Clin. Rheum. 5: 17-24). It is clinically characterized by joint pain, stiffness, and swelling due to synovial inflammation, leading to joint damage, deformity, severe disability, and increased mortality.

Patients may develop multiple systemic symptoms including fever, fatigue, anemia, and osteoporosis.

Initial treatment options include disease-modifying anti-rheumatic drugs (DMARDs), non-steroidal anti-inflammatory drugs (NSAIDs), corticosteroids, analgesics, surgery, physiotherapy, and occupational therapy. The synthetic DMARDs most commonly used include methotrexate (MTX), sulfasalazine, leflunomide, hydroxychloroquine, cyclosporine A, and glucocorticoids. The therapeutic benefits of DMARDs in RA include control of signs and symptoms, improvement of functional status and of quality of life, and retardation of joint damage progression (Firestein et al. 2006, Kelley's Textbook of Rheumatology ($8^{th}$ ed.) Elsevier, p. 1119-1143). MTX administered alone or in combination with another conventional DMARD, is the recommended first-line therapy for patients with RA (Coppieters et al. 2006, Arthritis Rheum. 54: 1856-1866).

For patients with an inadequate response to conventional DMARDs, biological drugs may be indicated. These biological drugs block certain key molecules that are involved in the pathogenesis of the illness. These targets include tumor necrosis factor alpha (TNFα), selective T-cell co-stimulation molecule (such as cytotoxic T-lymphocyte-associated protein 4), cluster of differentiation 20 (CD20), interleukin-1 (IL-1), IL-6, and interleukin-6 receptor (IL-6R). The development of immune-modulating agents has offered new treatment options for patients.

Although anti-TNFα agents and other biological DMARDs have been established as effective treatment options for RA, there are reasons to study the effectiveness of new therapeutic agents. For example, there is a subset of the patient population that does not achieve a clinical response, defined as American College of Rheumatology (ACR) 20 response, and only a small proportion achieve a high level ACR response (ACR50 or ACR70) (Dennis et al. 2002, J. Biol. Chem. 277: 35035-35043). Although therapy with biological DMARDs has been successful in the treatment of RA, certain patients may lose clinical response over time for various reasons such as disease burden, low drug serum levels, rapid clearance, and immunogenicity, in addition to other limitations with respect to safety, dosing regimen, and way of administration. Thus there is need for new therapeutic agents to address some of these limitations and to improve the effectiveness of biological agents in treating RA.

Systemic lupus erythematosus (SLE) or lupus, is a systemic autoimmune disease (or autoimmune connective tissue disease) that can affect any part of the body. As in other autoimmune diseases, the immune system attacks the body's cells and tissue, resulting in inflammation and tissue damage (James et al. 2005. Andrews' Diseases of the Skin: Clinical Dermatology. (10th ed.). Saunders). Bound antibody-antigen immune complexes precipitate and cause a further immune response.

The clinical presentation of SLE can be very diverse and can include disorders of joints, skin, heart, lungs, blood vessels, liver, kidneys, and nervous system. The course of the disease is unpredictable, with periods of illness (called flares) alternating with remissions. The disease occurs nine times more often in women than in men, especially in women in child-bearing years ages 15 to 35, and is also more common in those of non-European descent. Even if life expectancy of such patients has improved, a patient in whom lupus is diagnosed at 20 years of age still has a 1 in 6 chance of dying by 35 years of age, most often from lupus or infection. Later, myocardial infraction and stroke become important causes of death (Rahman and Isenberg 2008, N. Engl. J. Med. 358: 929-939).

There is no cure for SLE. Due to the variety of symptoms and organ system involvement with SLE, its severity in an individual must be assessed in order to initiate treatment.

Disease-modifying antirheumatic drugs (DMARDs) are used preventively to reduce the incidence of flares, to reduce the progress of the disease, and to lower the need for steroid use. Flares, when they occur, are treated with corticosteroids (prednisone). DMARDs commonly in use are antimalarials such as hydroxychloroquine and immunosuppressants (e.g. mycophenolate mofetil, methotrexate, leflunomide, tacrolimus and azathioprine). Hydroxychloroquine is an antimalarial used for constitutional, cutaneous, and articular manifestations. Hydroxychloroquine has relatively few side effects and there is evidence that it improves survival in SLE. Cyclophosphamide is used for severe glomerulonephritis or other organ-damaging complications. Mycophenolic acid is also used for treatment of lupus nephritis, but it is not FDA-approved for this indication, and FDA is investigating reports that it may be associated with birth defects when used by pregnant women.

Depending on the dosage, people who require steroids may develop Cushing's syndrome, symptoms of which may include obesity, puffy round face, diabetes mellitus, increased appetite, difficulty sleeping and osteoporosis. These may subside if and when the large initial dosage is reduced, but long-term use of even low doses can cause elevated blood pressure and cataracts.

Numerous new immunosuppressive drugs are being actively developed to treat SLE. Rather than suppressing the immune system nonspecifically, as corticosteroids do, they target the responses of individual immune cells and individual types of immune cells. Belimumab (trade name BENLYSTA®, previously known as LymphoStat-B), is a human monoclonal antibody that inhibits B-cell activating factor (BAFF), also known as B-lymphocyte stimulator (BLyS), and was approved by the FDA in March 2011.

There remains a need for new therapeutic agents to address some of the above limitations and to improve the effectiveness in treating SLE.

Available therapies for the prevention or treatment of these IL-6 related diseases may not be effective for all patients and/or may lose effectiveness over time for various reasons such as disease burden, low drug serum levels, rapid clearance, and immunogenicity, in addition to other limitations with respect to safety, dosing regimen, and route of administration. Furthermore, available therapies to treat, for example, IL-6 related autoimmune conditions, may only be appropriate for acute care because longer-term use of these therapies (e.g. steroids) can lead to the development of secondary medical conditions requiring further treatment.

Thus, for the treatment of IL-6 related disease, including, for example, rheumatoid arthritis (RA) and systemic lupus erythematosus (SLE), there is a need for new therapeutic agents to address the limitations of the available therapies and to improve the effectiveness of biological agents.

SEQ ID NO: 34 is a bivalent Nanobody consisting of two humanized and sequence-optimized variable domains derived from heavy chain-only llama antibodies. One domain (SEQ ID NO: 1) binds to IL-6R. The second domain (SEQ ID NO: 38) binds to human serum albumin (HSA). SEQ ID NO: 34 was extensively characterized in vitro (see for example WO 2010/115998).

A study assessing the safety, PK, PD, and efficacy after intravenous (i.v.) administration of SEQ ID NO: 34 in RA patients is described in WO 2013/041722. This placebo-controlled study included 28 subjects in an initial single ascending dose (SAD) part where single i.v. doses of 0.3, 1, 3, or 6 mg/kg were administered. In a subsequent multiple ascending dose (MAD) part, 37 subjects received multiple i.v. doses of 1 or 3 mg/kg every 4 weeks (q4w), or 6 mg/kg every 8 weeks, for 24 weeks in total. Dosing q4w at 3 mg/kg yielded the highest exposure, as indicated by the observed average trough levels (~10 µg/mL), strongest biomarker response (based on sIL-6R profile), and the highest clinical remission rates.

Intravenous (i.v.) injections, however, are generally performed by the physician or by the medical professional staff. Therefore, the patient is expected to visit a health care professional regularly in order to receive treatment. Besides the discomfort created, the time taken up by this type of application often leads to unsatisfactory compliance by the patient, particularly for chronic diseases. Subcutaneous (s.c.) injection renders the possibility to the patient to self-administer the drug and consequently improve patients' convenience. These advantages are even more evident in the case of a long-term therapy, such as the treatment of rheumatoid arthritis and systemic lupus erythematosus.

Drawbacks of subcutaneous administration, however, include the incomplete bioavailability after subcutaneous administration (Richter et al. 2012, AAPS J. 14: 559-570; Macdonald et al. 2010, Curr. Opin. Mol. Ther. 12: 461-470) and the relative slow subcutaneous absorption (Zheng et al. 2012, MAbs 4: 243-255). For marketed IgG, the subcutaneous bioavailability estimates are mostly around 60-80% (Richter and Jacobsen 2014, Drug Metab. Dispos. 2014, Aug. 6). In addition, subcutaneous absorption of protein, particularly monoclonal antibodies is slow, as indicated by time to maximum serum concentrations ($t_{max}$) ranging usually from around 3 to up to 8 days in humans (Richter and Jacobsen 2014).

Following i.v. administration a biotherapeutic is directly injected into the systemic circulation. Following s.c. administration, however, the biotherapeutic is injected into the extracellular space of the subcutaneous tissue, from where it has to be absorbed by blood or lymph capillaries in order to reach the systemic circulation. These processes are influenced by properties of the biotherapeutic as well as by host factors (Richter et al., 2012). These pre-systemic events have to be considered in understanding the subcutaneous administration of biotherapeutics. Transport in the subcutis to the absorbing blood or lymph capillaries appears to be a major contributor to the slow subcutaneous absorption. Larger proteins (>20 kDa) are mostly absorbed via the lymphatic system, though potential species differences are not fully understood yet. Also the presystemic catabolism leading to incomplete bioavailability is poorly understood, both the involved enzymes and its translation across species.

In view of these (poorly understood) factors that influence subcutaneous delivery of a biotherapeutic, the bioavailability and absorption rate of a new biotherapeutic upon subcutaneous administration cannot be predicted.

For IgGs, binding to neonatal Fc receptor (FcRn) appears important to obtain a high bioavailability. During s.c. absorption FcRn binding may prevent IgG from catabolism in subcutaneous tissue/lymphatics or may enhance the FcRn mediated transcytosis across the vascular endothelium (Richter et al., 2012). Subcutaneously administration of immunoglobulin single variable domains and their bioavailability and absorption rate has not yet been reported. These molecules do not possess an Fc region.

SUMMARY

The present disclosure demonstrates that subcutaneous administration of an immunoglobulin single variable domain provides a good bioavailability of more than 80% and an unexpectedly short time to maximum serum concentrations ($t_{max}$). Subcutaneous administration of an immunoglobulin single variable domain that binds and blocks IL-6R (SEQ ID NO: 34) resulted in a bioavailability of more than 80%. Maximum serum concentrations of the immunoglobulin single variable domain were already reached after about 1-3 days. Based on these results, the present invention provides dose regimens for subcutaneous administration of immunoglobulin single variable domains to human subjects. More specifically, the present invention provides dose regimens for subcutaneous administration of immunoglobulin single variable domains that bind and block IL-6R to human subjects suffering an IL-6R related disease.

Accordingly, the present invention relates to a method for the treatment of an IL-6R related disease in a human subject, said method comprising the administration to a human subject suffering from the IL-6R related disease, of a polypeptide comprising, consisting essentially of, or consisting of at least one immunoglobulin single variable domain that binds IL-6R and that blocks IL-6 binding to IL-6R, wherein the polypeptide is administered subcutaneously at a dose of 75-300 mg every week to every month or at a dose equivalent to 75-300 mg every week to every month.

In a preferred aspect, the immunoglobulin single variable domain binds IL-6R with a $K_D$ of $5\times10^{-11}$ M or less. Accordingly, the present invention relates to a method for the treatment of an IL-6R related disease in a human subject, said method comprising the administration to a human subject suffering from the IL-6R related disease, of a polypeptide comprising, consisting essentially of, or consisting of at least one immunoglobulin single variable domain that binds IL-6R with a $K_D$ of $5\times10^{-11}$ M or less, wherein the polypeptide is administered subcutaneously at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the dissociation constant ($K_D$) may be measured by, for example, surface plasmon resonance.

In another preferred aspect, the immunoglobulin single variable domain blocks IL-6 binding to IL-6R with an IC50 of $10^{-9}$ M or less. Accordingly, the present invention relates to a method for the treatment of an IL-6R related disease in a human subject, said method comprising the administration to a human subject suffering from the IL-6R related disease, of a polypeptide comprising, consisting essentially of, or consisting of at least one immunoglobulin single variable domain that blocks IL-6 binding to IL-6R with an IC50 of $10^{-9}$ M or less, wherein the polypeptide is administered subcutaneously at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the IC50 may be measured by, for example, a TF-1 potency assay. For certain embodiments or aspects of the immunoglobulin single variable domains and methods of use of the immunoglobulin single variable domains of the disclosure, the IC50 may be measured by, for example, a TF-1 proliferation assay at 100 IU/mL IL-6.

In a preferred aspect, the present invention relates to a method for the treatment of an IL-6R related disease in a human subject, said method comprising the administration to a human subject suffering from the IL-6R related disease, of a polypeptide comprising, consisting essentially of, or consisting of at least one immunoglobulin single variable domain that binds IL-6R with a $K_D$ of $5\times10^{-11}$ M or less and that blocks IL-6 binding to IL-6R with an IC50 of $10^{-9}$ M or less, wherein the polypeptide is administered subcutaneously at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the $K_D$ may be measured by, for example, surface plasmon resonance. For certain embodiments or aspects of the immunoglobulin single variable domains and methods of use of the immunoglobulin single variable domains of the disclosure, the IC50 may be measured by, for example, a TF-1 potency assay. For certain embodiments or aspects of the immunoglobulin single variable domains and methods of use of the immunoglobulin single variable domains of the disclosure, the IC50 may be measured by, for example, a TF-1 proliferation assay at 100 IU/mL IL-6.

The present invention also provides a polypeptide (also referred to herein as "polypeptide of the invention") comprising, consisting essentially of, or consisting of an immunoglobulin single variable domain that binds IL-6R and that blocks IL-6 binding to IL-6R, for use in the treatment of an IL-6R related disease in a human subject, wherein the polypeptide is administered subcutaneously to a human subject suffering the IL-6R related disease at a dose of 75-300 mg every week to every month or at a dose equivalent to 75-300 mg every week to every month.

In a preferred aspect, the immunoglobulin single variable domain binds IL-6R with a $K_D$ of $5\times10^{-11}$ M or less. Accordingly, the present invention relates to a polypeptide (also referred to herein as "polypeptide of the invention") comprising, consisting essentially of, or consisting of an immunoglobulin single variable domain that binds IL-6R with a $K_D$ of $5\times10^{-11}$ M or less, for use in the treatment of an IL-6R related disease in a human subject, wherein the polypeptide is administered subcutaneously to a human subject suffering the IL-6R related disease at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the $K_D$ may be measured by, for example, surface plasmon resonance.

In another preferred aspect, the immunoglobulin single variable domain blocks IL-6 binding to IL-6R with an IC50 of $10^{-9}$ M or less. Accordingly, the present invention relates to a polypeptide (also referred to herein as "polypeptide of the invention") comprising, consisting essentially of, or consisting of an immunoglobulin single variable domain that blocks IL-6 binding to IL-6R with an IC50 of $10^{-9}$ M, for use in the treatment of an IL-6R related disease in a human subject, wherein the polypeptide is administered subcutaneously to a human subject suffering the IL-6R related disease at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the IC50 may be measured by, for example, a TF-1 potency assay. For certain embodiments or aspects of the immunoglobulin single variable domains and methods of use of the immunoglobulin single variable domains of the disclosure, the IC50 may be measured by, for example, a TF-1 proliferation assay at 100 IU/mL IL-6.

In another preferred aspect, the present invention provides a polypeptide (also referred to herein as "polypeptide of the invention") comprising, consisting essentially of, or consisting of an immunoglobulin single variable domain that binds IL-6R with a $K_D$ of $5\times10^{-11}$ M or less and that blocks IL-6 binding to IL-6R with an IC50 of $10^{-9}$ M, for use in the treatment of an IL-6R related disease in a human subject, wherein the polypeptide is administered subcutaneously to a human subject suffering the IL-6R related disease at a dose of 75-300 mg every week to every month or at a dose equivalent to 75-300 mg every week to every month. For certain embodiments or aspects of the immunoglobulin single variable domains and methods of use of the immunoglobulin single variable domains of the disclosure, the $K_D$ may be measured by, for example, surface plasmon resonance. For certain embodiments or aspects of the immunoglobulin single variable domains and methods of use of the immunoglobulin single variable domains of the disclosure, the IC50 may be measured by, for example, a TF-1 potency assay.

The human subject treated with the polypeptide of the invention may be suffering from any IL-6R related disease (as further defined herein). In one aspect, the human subject is suffering from rheumatoid arthritis. In one aspect, the human subject is suffering from active rheumatoid arthritis. In one aspect, the human subject is suffering from active rheumatoid arthritis despite methotrexate therapy. In one aspect, the human subject is suffering from active rheumatoid arthritis and is intolerant to MTX. In one aspect, the human subject is suffering from systemic lupus erythematosus. In one aspect, the human subject is suffering from moderate to severe active systemic lupus erythematosus.

The immunoglobulin single variable domain encompassed in the polypeptide of the invention administered subcutaneously may be any immunoglobulin single variable domain that binds IL-6R. In one aspect, the immunoglobulin single variable domain binds IL-6R with a $K_D$ of $5\times10^{-11}$ M or less. In one aspect, the immunoglobulin single variable domain blocks IL-6 binding to IL-6R with an IC50 of $10^{-9}$M or less. In one aspect, the immunoglobulin single variable domain binds IL-6R with a $K_D$ of $5\times10^{-11}$ M or less and blocks IL-6 binding to IL-6R with an IC50 of $10^{-9}$ M or less. For certain embodiments or aspects of the immunoglobulin single variable domains and methods of use of the immunoglobulin single variable domains of the disclosure, the $K_D$ may be measured by, for example, surface plasmon resonance. For certain embodiments or aspects of the immunoglobulin single variable domains and methods of use of the immunoglobulin single variable domains of the disclosure, the IC50 may be measured by, for example, a TF-1 potency assay. For certain embodiments or aspects of the immunoglobulin single variable domains and methods of use of the immunoglobulin single variable domains of the disclosure, the IC50 may be measured by, for example, a TF-1 proliferation assay at 100 IU/mL IL-6.

In one aspect, the immunoglobulin single variable domain encompassed in the polypeptide of the invention administered subcutaneously comprises a CDR1 having the amino acid sequence of SEQ ID NO: 17, a CDR2 having the amino acid sequence of SEQ ID NO: 21, and a CDR3 having the amino acid sequence of SEQ ID NO: 30. In one aspect, the immunoglobulin single variable domain encompassed in the polypeptide of the invention administered subcutaneously is selected from SEQ ID NOs: 1-10.

The polypeptide of the invention that is administered subcutaneously may additionally comprise an immunoglobulin single variable domain that binds human serum albumin. In one aspect, the additional immunoglobulin single variable domain that binds human serum albumin is selected from SEQ ID NOs: 37-39.

In a preferred aspect, the polypeptide of the invention that is administered subcutaneously has the amino acid sequence of SEQ ID NO: 34. Accordingly, the present invention relates to a method for the treatment of an IL-6R related disease in a human subject, said method comprising the administration to a human subject suffering from the IL-6R related disease, of a polypeptide with SEQ ID NO: 34, wherein the polypeptide is administered subcutaneously at a dose of 75-300 mg every week to every month or at a dose equivalent to 75-300 mg every week to every month.

The polypeptide of the invention is administered subcutaneously every week to every month. In one aspect, the polypeptide of the invention is administered every week. In one aspect, the polypeptide of the invention is administered every two weeks. In one aspect, the polypeptide of the invention is administered every four weeks. In one aspect, the polypeptide of the invention is administered every month.

The polypeptide of the invention is administered subcutaneously at a dose of 75-300 mg. In one aspect, the polypeptide of the invention is administered at a dose of 75-150 mg, such as e.g. 75 mg. In one aspect, the polypeptide of the invention is administered at a dose of 150-200 mg, such as e.g. 150 mg. In one aspect, the polypeptide of the invention is administered at a dose of 200-250 mg, such as e.g. 225 mg. In one aspect, the polypeptide of the invention is administered at a dose of 250-300 mg, such as e.g. 300 mg.

The polypeptide of the invention may be administered as a monotherapy or as a combination therapy. In one aspect, the polypeptide of the invention is administered as a monotherapy. In one aspect, the polypeptide of the invention is administered in combination with at least one additional therapeutic agent. Without being limiting, additional therapeutic agents may include disease-modifying antirheumatic drugs (DMARDs), nonsteroidal anti-inflammatory drugs (NSAIDs), corticosteroids and biological therapies.

In one aspect, the polypeptide of the invention is administered in combination with methotrexate. Methotrexate can be co-administered e.g. at a dose of 12.5-25 mg weekly.

In one aspect, the pharmaceutical composition comprising the polypeptide of the invention is loaded into a pre-filled syringe (also referred to herein as "pre-filled syringe of the invention"). Accordingly, the present invention also relates to pre-filled syringes containing the polypeptide of the invention. In one aspect, the present invention relates to a pre-filled syringe containing a pharmaceutical composition comprising a polypeptide comprising, consisting essentially of, or consisting of an immunoglobulin single variable domain that binds IL-6R and that blocks IL-6 binding to IL-6R. In one aspect, the present invention relates to a pre-filled syringe containing a pharmaceutical composition comprising a polypeptide comprising, consisting essentially of, or consisting of an immunoglobulin single variable domain that binds IL-6R with a $K_D$ of $5\times10^{-11}$ M or less. In one aspect, the present invention relates to a pre-filled syringe containing a pharmaceutical composition comprising a polypeptide comprising, consisting essentially of, or consisting of an immunoglobulin single variable domain that blocks IL-6 binding to IL-6R with an IC50 of $10^{-9}$ M. In one aspect, the present invention relates to a pre-filled syringe containing a pharmaceutical composition comprising a polypeptide comprising, consisting essentially of, or consisting of an immunoglobulin single variable domain that binds IL-6R with a $K_D$ of $5\times10^{-11}$ M or less and that blocks IL-6 binding to IL-6R with an IC50 of $10^{-9}$ M. For certain embodiments or aspects of the immunoglobulin single variable domains and methods of use of the immunoglobulin single variable domains of the disclosure, the $K_D$ may be measured by, for example, surface plasmon resonance. For certain embodiments or aspects of the immunoglobulin single variable domains and methods of use of the immunoglobulin single variable domains of the disclosure, the IC50 may be measured by, for example, a TF-1 potency assay. For certain embodiments or aspects of the immunoglobulin single variable domains and methods of use of the immunoglobulin single variable domains of the disclosure, the IC50 may be measured by, for example, a TF-1 proliferation assay at 100 IU/mL IL-6.

In one aspect, the pre-filled syringe contains a polypeptide comprising, consisting essentially of, or consisting of an immunoglobulin single variable domain with a CDR1 having the amino acid sequence of SEQ ID NO: 17, a CDR2 having the amino acid sequence of SEQ ID NO: 21, and a CDR3 having the amino acid sequence of SEQ ID NO: 30. In one aspect, the pre-filled syringe contains a polypeptide comprising, consisting essentially of, or consisting of an immunoglobulin single variable domain selected from SEQ ID NOs: 1-10.

In one aspect, the pre-filled syringe contains a polypeptide that comprises an immunoglobulin single variable domain that binds IL-6R and that additionally comprises an immunoglobulin single variable domain that binds human serum albumin. In one aspect, the immunoglobulin single variable domain that binds human serum albumin has an amino acid sequence selected from SEQ ID NO: 37-39. In one aspect, the pre-filled syringe contains a polypeptide with SEQ ID NO: 34. Accordingly, the present invention relates to a pre-filled syringe containing a pharmaceutical composition comprising a polypeptide with SEQ ID NO: 34.

The pre-filled syringe can be any size that is suitable for subcutaneous administration. In one aspect, a 0.5 ml syringe is used. In one aspect, a 1 ml syringe is used.

The polypeptide of the invention can be present in the pharmaceutical composition at any concentration which is suitable for subcutaneous administration. In one aspect, the polypeptide is present in the pharmaceutical composition at a concentration of 150 mg/ml.

In a preferred aspect, a 1 ml syringe is used with a 150 mg/ml pharmaceutical composition of the polypeptide of the invention and, as such, the pre-filled syringe contains 150 mg of polypeptide of the invention. Accordingly, a dose of 150 mg can be obtained by subcutaneous administration of the pharmaceutical composition present in one such pre-filled syringe. A dose of 300 mg can be obtained by subcutaneous administration of the pharmaceutical composition present in two such pre-filled syringes.

In another preferred aspect, a 0.5 ml syringe is used with a 150 mg/ml pharmaceutical composition of the polypeptide of the invention and, as such, the pre-filled syringe contains 75 mg of polypeptide of the invention. Accordingly, a dose of 75 mg can be obtained by subcutaneous administration of the pharmaceutical composition present in one such pre-filled syringe. A dose of 150 mg can be obtained by subcutaneous administration of the pharmaceutical composition present in two such pre-filled syringes. A dose of 225 mg can be obtained by subcutaneous administration of the pharmaceutical composition present in one such 1 ml pre-filled syringes and 1 such 0.5 ml pre-filled syringe.

According to the present invention, the pre-filled syringe of the invention is used for the treatment of an IL-6R related disease in a human subject. Accordingly, the present invention relates to a pre-filled syringe containing a pharmaceutical composition comprising the polypeptide of the invention for use in the treatment of an IL-6R related disease in a human subject. The present invention further relates to a pre-filled syringe containing a pharmaceutical composition comprising the polypeptide of the invention for use in the treatment of an IL-6R related disease in a human subject, wherein the polypeptide is administered subcutaneously. The present invention also relates to a pre-filled syringe containing a pharmaceutical composition comprising the polypeptide of the invention for use in the treatment of an IL-6R related disease in a human subject, wherein the polypeptide is administered subcutaneously at a dose of 75-300 mg every week to every month or at a dose equivalent to 75-300 mg every week to every month.

The human subject treated with the pre-filled syringe of the present invention may be suffering from any IL-6R related disease (as further defined herein). In one aspect, the human subject is suffering from rheumatoid arthritis. In one aspect, the human subject is suffering from active rheumatoid arthritis. In one aspect, the human subject is suffering from active rheumatoid arthritis despite methotrexate therapy. In one aspect, the human subject is suffering from active rheumatoid arthritis and is intolerant to MTX. In one aspect, the human subject is suffering from systemic lupus erythematosus. In one aspect, the human subject is suffering from moderate to severe active systemic lupus erythematosus.

The polypeptide of the invention present in the pre-filled syringe is administered subcutaneously at a dose of 75-300 mg every week to every month or at a dose equivalent to 75-300 mg every week to every month.

In one aspect, the polypeptide in the pre-filled syringe is administered every week.

In one aspect, the polypeptide in the pre-filled syringe is administered every two weeks.

In one aspect, the polypeptide in the pre-filled syringe is administered every four weeks.

In one aspect, the polypeptide in the pre-filled syringe is administered every month.

In one aspect, the polypeptide in the pre-filled syringe is administered at a dose of 75-150 mg.

In one aspect, the polypeptide in the pre-filled syringe is administered at a dose of 75 mg.

In one aspect, the polypeptide in the pre-filled syringe is administered at a dose of 150-200 mg.

In one aspect, the polypeptide in the pre-filled syringe is administered at a dose of 150 mg.

In one aspect, the polypeptide in the pre-filled syringe is administered at a dose of 200-250 mg.

In one aspect, the polypeptide in the pre-filled syringe is administered at a dose of 225 mg.

In one aspect, the polypeptide in the pre-filled syringe is administered at a dose of 250-300 mg.

In one aspect, the polypeptide in the pre-filled syringe is administered at a dose of 300 mg.

The polypeptide present in the pre-filled syringe may be administered as a monotherapy or as a combination therapy. In one aspect, the polypeptide present in the pre-filled syringe is administered as a monotherapy. In one aspect, the polypeptide present in the pre-filled syringe is administered in combination with at least one additional therapeutic agent. Without being limiting, additional therapeutic agents include disease-modifying antirheumatic drugs (DMARDs), nonsteroidal anti-inflammatory drugs (NSAIDs), and corticosteroids.

In one aspect, the polypeptide present in the pre-filled syringe is administered in combination with methotrexate. Methotrexate can be co-administered e.g. at a dose of 12.5-25 mg weekly.

BRIEF DESCRIPTION OF THE DRAWINGS

(FIG. 1A) Linear; (FIG. 1B) Semi-Logarithmic.

DETAILED DESCRIPTION

Definitions

Figure 1A:
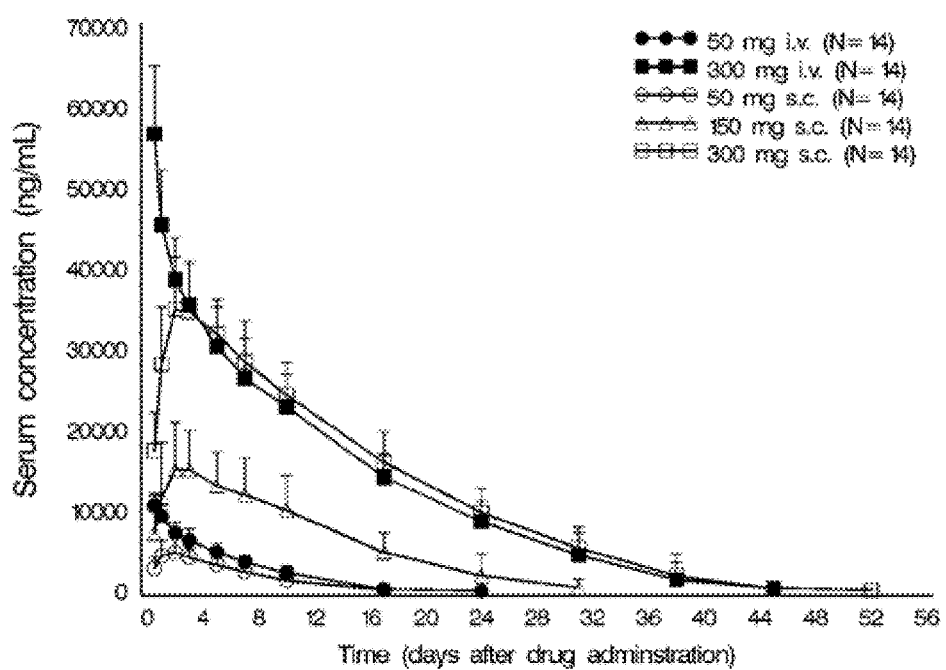
FIGS. 1A and 1B are a pair of graphs depicting the geometric mean serum concentration-time profiles of SEQ ID NO: 34 after s.c. and i.v. administration in healthy human subjects.

Unless indicated or defined otherwise, all terms used have their usual meaning in the art, which will be clear to the skilled person. Reference is for example made to the standard handbooks, such as Sambrook et al. "Molecular Cloning: A Laboratory Manual" (2nd. Ed.), Vols. 1-3, Cold Spring Harbor Laboratory Press (1989); F. Ausubel et al. eds., "Current protocols in molecular biology", Green Publishing and Wiley Interscience, New York (1987); Lewin "Genes II", John Wiley & Sons, New York, N.Y., (1985); Old et al. "Principles of Gene Manipulation: An Introduction to Genetic Engineering", 2nd edition, University of California Press, Berkeley, Calif. (1981); Roitt et al. "Immunology" (6th. Ed.), Mosby/Elsevier, Edinburgh (2001); Roitt et al. Roitt's Essential Immunology, 10$^{th}$ Ed. Blackwell Publishing, U K (2001); and Janeway et al. "Immunobiology" (6th Ed.), Garland Science Publishing/Churchill Livingstone, N.Y. (2005), as well as to the general background patent and non-patent publications cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta 2006 (Adv. Drug Deliv. Rev. 58 (5-6): 640-56), Levin and Weiss 2006 (Mol. Biosyst. 2(1): 49-57), Irving et al. 2001 (J. Immunol. Methods 248(1-2): 31-45), Schmitz et al. 2000 (Placenta 21 Suppl. A: S106-12), Gonzales et al. 2005 (Tumour Biol. 26(1): 31-43), which describe techniques for protein engineering, such as affinity maturation and other techniques for improving the specificity and other desired properties of proteins such as immunoglobulins.

A nucleic acid sequence or amino acid sequence is considered to be "(in) essentially isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist(s) of", "essentially consisting of", "consist(s) essentially of", "consisting essentially of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

In addition, the term "sequence" as used herein (for example in terms like "immunoglobulin sequence", "variable domain sequence", "immunoglobulin single variable domain sequence", "VHH sequence" or "protein sequence"), should generally be understood to include both the relevant amino acid sequence as well as nucleic acid sequences or nucleotide sequences encoding the same, unless the context requires a more limited interpretation.

An amino acid sequence (such as an immunoglobulin single variable domain, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The "affinity" denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules (such as immunoglobulin single variable domain or polypeptide of the invention and IL-6R) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well-known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$.

Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles or more). Any $K_D$ value greater than $10^{-4}$ mol/liter (or any $K_A$ value lower than $10^4$ liter/moles) is generally considered to indicate non-specific binding. Preferably, a monovalent immunoglobulin sequence of the invention will bind to the desired antigen with an affinity less than 500 nM, preferably less than 200 nM, more preferably less than 10 nM, such as e.g. less than 500 pM or $5\times10^{-11}$ M or less.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$ s$^{-1}$. The on-rate may vary between $10^2$ M$^{-1}$ s$^{-1}$ to about $10^7$ M$^{-1}$ s$^{-1}$, approaching the diffusion-limited association rate constant for bimolecular interactions. The off-rate is related to the half-life of a given molecular interaction by the relation $t_{1/2}$=ln(2)/$k_{off}$. The off-rate may vary between $10^{-6}$ s$^{-1}$ (near irreversible complex with a $t_{1/2}$ of multiple days) to 1 s$^{-1}$ ($t_{1/2}$=0.69 s).

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known Biacore instruments (Pharmacia Biosensor AB, Uppsala, Sweden). Kinetic Exclusion Assay (KinExA) (Drake et al. 2004, Analytical Biochemistry 328: 35-43) measures binding events in solution without labeling of the binding partners and is based upon kinetically excluding the dissociation of a complex.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

"Avidity" is the measure of the strength of binding between an antigen-binding molecule (such as an immunoglobulin single variable domain or polypeptide of the invention) and the pertinent antigen. Avidity is related to both the affinity between an antigenic determinant and its antigen binding site on the antigen-binding molecule and the number of pertinent binding sites present on the antigen-binding molecule.

The term "specificity" refers to the number of different types of antigens or antigenic determinants to which a particular antigen-binding molecule or antigen-binding protein (such as an immunoglobulin single variable domain or a polypeptide of the invention) can bind. The specificity of an antigen-binding protein can be determined based on affinity and/or avidity. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

"Blocking IL-6 binding to IL-6R" means that the immunoglobulin single variable domain is capable of competing with IL-6 for binding to the IL-6 receptor. As such, binding of IL-6 to IL-6R is blocked, inhibited or reduced compared to the binding of IL-6 to its IL-6R without the presence of the immunoglobulin single variable domain. Immunoglobulin single variable domains that "block IL-6 binding to IL-6" bind to an epitope on IL-6R close to the IL-6 interaction side on IL-6R. "Blocking IL-6 binding to IL-6R" by the immunoglobulin and/or polypeptide of the invention can be determined, for example, in the TF-1 assay as described by Kitamura et al. (1989, J. Cell Physiol., 140: 323). In this assay, the immunoglobulin single variable domain present in the polypeptide of the invention may have IC50 values (at 100 IU/mL IL-6) between 10 nM and 50 pM, preferably between 5 nM and 50 pM, more preferably between 1 nM and 50 pM or less, such as e.g. $10^{-9}$ M or less or about 750 or 500 pM or less. In this TF-1 assay the amino acid sequences of the invention may have IC50 values (at 5000 IU/mL IL-6) between 50 nM and 1 nM, preferably between 25 nM and 1 nM, more preferably between 10 nM and 1 nM or less, such as about 8 nM or less.

The "half-life" of a polypeptide of the invention can generally be defined as the time taken for the serum concentration of the polypeptide to be reduced by 50%, in vivo, for example due to degradation of the sequence or compound and/or clearance or sequestration of the sequence or compound by natural mechanisms. The in vivo half-life of a polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)), a suitable dose of the polypeptide of the invention; collecting blood samples or other samples from said animal; determining the level or concentration of the polypeptide of the invention in said blood sample; and calculating, from (a plot of) the data thus obtained, the time until the level or concentration of the polypeptide of the invention has been reduced by 50% compared to the initial level upon dosing. Reference is for example made to the Experimental Part below, as well as to the standard handbooks, such as Kenneth et al. 1996 (Chemical Stability of Pharmaceuticals: A Handbook for Pharmacists and Peters et al, Pharmacokinete analysis: A Practical Approach). Reference is also made to Gibaldi and Perron 1982 (Pharmacokinetics, published by Marcel Dekker, 2nd Rev. edition).

As will also be clear to the skilled person (see for example pages 6 and 7 of WO 04/003019 and in the further references cited therein), the half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t½-beta, either with or without an increase in the t½-alpha and/or the AUC or both.

"Bioavailability", as used in the present invention, refers to the fraction (or percent) of the administered dose systemically absorbed intact.

"$t_{max}$", as used in the present invention, is the time needed to obtain the maximum concentration of drug (such as the polypeptide of the invention) in the systemic circulation and, as such, refers to the rate of drug input into the systemic circulation.

The term "dose" refers to an amount of polypeptide of the invention that is administered to the subject. The term "dosing" refers to the administration of the polypeptide of the invention.

A "dose regimen" refers to the schedule of doses of the polypeptide of the invention per unit of time.

An "equivalent dose (to an indicated dose regimen)" or "a dose equivalent to (an indicated dose regimen)" as used in the present invention means that the amount of polypeptide administered to the subject per unit of time is identical to the amount of polypeptide administered to the subject per unit of time in the indicated dose regimen.

The terms "weekly" or "every week", "biweekly" or "every 2 weeks", "4 weekly" or "every 4 weeks" and "monthly" or "every month" in the context of "weekly", "biweekly", "4 weekly" and "monthly" administration and/ or "weekly", "biweekly", "4 weekly" and "monthly" dosing schedule, as used herein, refer to the time course of administering the polypeptide of the invention to the subject to achieve the treatment of the IL-6R related disease. In a "weekly" dosing regimen the polypeptide of the invention is administered every week, such as every 5-9 days, more preferably, every 6-8 days, and most preferably, every 7 days. In a "biweekly" dosing regimen the polypeptide of the invention is administered every 2 weeks, such as every 9-19 days, more preferably, every 11-17 days, even more preferably, every 13-15 days, and most preferably, every 14 days. In a "4 weekly" dosing regimen the polypeptide of the invention is administered every 4 weeks, such as every 23-33 days, more preferably, every 25-31 days, even more preferably, every 27-29 days, and most preferably, every 28 days. In a "monthly" dosing regimen the polypeptide of the invention is administered every month, such as every 25-34 days, more preferably, every 26-33 days, even more preferably, every 27-32 days, and most preferably, every 28-31 days.

Polypeptide of the Invention

Polypeptides of the invention may be non-naturally occurring. Thus, the polypeptides of the invention may have been designed, manufactured, synthesized, and/or recombined to produce a non-naturally occurring sequence.

Immunoglobulin Single Variable Domain

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, immunoglobulin single variable domains will be amino acid sequences that essentially consist of 4 framework regions (FR1 to FR4 respectively) and 3 complementarity determining regions (CDR1 to CDR3 respectively). Such immunoglobulin single variable domains and fragments are most preferably such that they comprise an immunoglobulin fold or are capable for forming, under suitable conditions, an immunoglobulin fold. As such, the immunoglobulin single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the immunoglobulin single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody.

For a general description of heavy chain antibodies and the variable domains thereof, reference is inter alia made to the patent and non-patent publications cited herein, as well as to the patent and non-patent publications mentioned on page 59 of WO 08/020079 and to the list of references mentioned on pages 41-43 of the International application WO 06/040153, which patent and non-patent publications as well as references are incorporated herein by reference.

For example, the single variable domain or immunoglobulin single variable domain (or an amino acid sequence that is suitable for use as an immunoglobulin single variable domain) may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH sequence); other immunoglobulin single variable domains, or any suitable fragment of any one thereof. For a general description of (single) domain antibodies, reference is also made to the patent and non-patent publications cited herein, as well as to EP 0 368 684. For the term "dAb's", reference is for example made to Ward et al. 1989 (Nature 341: 544-6), to Holt et al. 2003 (Trends Biotechnol. 21: 484-490); as well as to for example WO 04/068820, WO 06/030220, WO 06/003388 and other published patent applications of Domantis Ltd. It should also be noted that, although less preferred in the context of the present invention because they are not of mammalian origin, immunoglobulin single variable domains can be derived from certain species of shark (for example, the so-called "IgNAR domains", see for example WO 05/18629).

In particular, the immunoglobulin single variable domain may be a NANOBODY® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the patent and non-patent publications cited herein, such as e.g. described in WO 08/020079 (page 16).

The amino acid sequence and structure of an immunoglobulin sequence, in particular an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain can be in the region of 110-120, is preferably 112-115, and is most preferably 113. It should however be noted that parts, fragments, analogs or derivatives of an immunoglobulin single variable domain are not particularly limited as to their length and/or size, as long as such parts, fragments, analogs or derivatives meet the further requirements outlined herein and are also preferably suitable for the purposes described herein.

For a further description of VHH's and Nanobodies, reference is made to the review article by Muyldermans 2001 (Reviews in Molecular Biotechnology 74: 277-302); as well as to the following patent applications, which are mentioned as general background art: WO 94/04678, WO 95/04079, WO 96/34103, WO 94/25591, WO 99/37681, WO 00/40968, WO 00/43507, WO 00/65057, WO 01/40310, WO 01/44301, EP 1134231, WO 02/48193, WO 97/49805, WO 01/21817, WO 03/035694, WO 03/054016, WO 03/055527, WO 03/050531, WO 01/90190, WO 03/025020, WO 04/041867, WO 04/041862, WO 04/041865, WO 04/041868, WO 04/062551, WO 05/044858, WO 06/40153, WO 06/079372, WO 06/122786, WO 06/122787, WO 06/122825. Reference is also made to the further patent and non-patent publications mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "immunoglobulin single variable domain" or "single variable domain" comprises polypeptides which are derived from a non-human source, preferably a camelid, preferably a camel heavy chain antibody. They may be humanized, as previously described. Moreover, the term comprises polypeptides derived from non-camelid sources, e.g. mouse or human, which have been "camelized", as previously described.

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences (such as e.g. VHHs) and humanized camelid immunoglobulin sequences (such as e.g. humanized VHHs), or camelized immunoglobulin single variable domains, e.g. camelized dAb as described by Ward et al (see for example WO 94/04678 and Davies and Riechmann 1994, Febs Lett. 339: 285 and 1996, Protein Engineering 9: 531) and/or camelized VHs.

Immunoglobulin single variable domains (and polypeptides comprising the same) that are directed against IL-6R have been described in WO 2008/020079 and WO 2010/115998. Preferred immunoglobulin single variable domains for use in the polypeptides of the invention include the improved Nanobodies described in WO 2010/115998.

Preferred immunoglobulin single variable domains that specifically bind IL-6R, in some aspects have an apparent $K_D$ for binding to IL-6R, as determined by Biacore assay (surface plasmon resonance), of 1 nM to 1 pM (moles/litre) or less, preferably 500 pM to 1 pM (moles/litre) or less, more preferably 100 pM to 1 pM (moles/litre) or less, or even more preferably about 50 pM to 1 pM or less, such as $5 \times 10^{-11}$M or less.

Preferred immunoglobulin single variable domains that specifically bind IL-6R, in some aspects block binding of IL-6 to IL-6R, as e.g. measured in a TF-1 proliferation assay as described for example in WO 2010/115998 and/or by Kitamura et al. (1989, J. Cell Physiol., 140: 323), with an IC50 values (at 100 IU/mL IL-6) between 10 nM and 50 pM, preferably between 5 nM and 50 pM, more preferably between 1 nM and 50 pM or less, such as about 750 or 500 pM or less or $10^{-9}$M or less and/or with an IC50 values (at 5000 IU/mL IL-6) between 50 nM and 1 nM, preferably between 25 nM and 1 nM, more preferably between 10 nM and 1 nM or less, such as about 8 nM or less.

For example, preferred immunoglobulin single variable domains may essentially consist of 4 framework regions (FR1 to FR4, respectively) and 3 complementarity determining regions (CDR1 to CDR3, respectively), in which:
  a) CDR1 is chosen from the group consisting of: SEQ ID NOs: 17-19;
  b) CDR2 is chosen from the group consisting of: SEQ ID NO's: 21-28; and
  c) CDR3 is chosen from the group consisting of: SEQ ID NO's: 30-32.

More preferably, the immunoglobulin single variable domain used in the polypeptide of the invention essentially consists of 4 framework regions (FR1 to FR4, respectively) and 3 complementarity determining regions (CDR1 to CDR3, respectively), in which:
  a) CDR1 is chosen from SEQ ID NO: 17;
  b) CDR2 is chosen from SEQ ID NO: 21; and
  c) CDR3 is chosen from SEQ ID NO: 30.

Preferred immunoglobulin single variable domains for use in the polypeptide of the invention include SEQ ID NO's: 1-10, more particularly SEQ ID NO's: 1, 6, and 8-10 of which SEQ ID NO: 1 is particularly preferred.

Polypeptide of the Invention

The immunoglobulin single variable domains for use in the method of the invention may form part of a polypeptide (referred herein as "polypeptide of the invention"), which may comprise, consist essentially of, or consist of one or more immunoglobulin single variable domains that specifically binds IL-6R and which may optionally further comprise one or more further amino acid sequences (all optionally linked via one or more suitable linkers). The term "immunoglobulin single variable domain" may also encompass such polypeptide of the invention. For example, and without limitation, the one or more immunoglobulin single variable domains may be used as a binding unit in such a polypeptide, which may optionally contain one or more further amino acid sequences that can serve as a binding unit, so as to provide a monovalent, multivalent or multispecific polypeptide of the invention, respectively (for multivalent and multispecific polypeptides containing one or more VHH domains and their preparation, reference is also made to Conrath et al. 2001 (J. Biol. Chem. 276: 7346-7350), as well as to for example WO 96/34103, WO 99/23221 and WO 2010/115998).

The polypeptides of the invention may encompass constructs comprising two or more antigen binding units in the form of single variable domains. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, an immunoglobulin single variable domain according to the invention may comprise two or three immunoglobulin single variable domains directed against the same target (i.e. IL-6R), or one or two immunoglobulin single variable domains directed against target A (i.e. IL-6R), and one immunoglobulin single variable domain against target B. Such constructs and modifications thereof, which the skilled person can readily envisage, are all encompassed by the term immunoglobulin single variable domain as used herein.

In an aspect of the invention, the polypeptide of the invention that comprises, consists essentially of, or consists of one or more immunoglobulin single variable domains that specifically bind IL-6R, may further comprise one or more other groups, residues, moieties or binding units. Such further groups, residues, moieties, binding units may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the compound, construct or polypeptide is a (fusion) protein or (fusion) polypeptide. In a preferred but non-limiting aspect, said one or more other groups, residues, moieties or binding units are immunoglobulin sequences, preferably immunoglobulin single variable domains. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domain so as to provide a "derivative" of the immunoglobulin single variable domain.

In the polypeptides described above, the one or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

Suitable spacers or linkers for use in multivalent and/or multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background patent and non-patent publications cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent VH and VL domains to come together to form the complete antigen-binding site, there is no particular limitation on the length or the flexibility of the linker used in the polypeptide of the invention, since each amino acid sequence or Nanobody by itself forms a complete antigen-binding site).

For example, a linker may be a suitable amino acid sequence, and in particular amino acid sequences of between 1 and 50, preferably between 1 and 30, such as between 1 and 20 or between 1 and 10 amino acid residues. Widely used peptide linkers comprise Gly-Ser repeats, e.g. (Gly)4-Ser in one, two, three, four, five, six or more repeats, or for example of the type $(gly_xser_y)_2$, such as (for example $(gly_4ser)_3$ or $(gly_3ser_2)_3$, as described in WO 99/42077, or hinge-like regions such as the hinge regions of naturally occurring heavy chain antibodies or similar sequences (such as described in WO 94/04678). Some other particularly preferred linkers are poly-alanine (such as AAA), as well as the linkers mentioned in Table A-5, of which AAA, GS-7, GS-8 and GS-9 are particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

In one specific aspect of the invention, a polypeptide of the invention is prepared that has an increased half-life, compared to the corresponding immunoglobulin single variable domain. Examples of polypeptides of the invention that comprise such half-life extending moieties for example include, without limitation, polypeptides in which the immunoglobulin single variable domain is suitable linked to one or more serum proteins or fragments thereof (such as (human) serum albumin or suitable fragments thereof) or to one or more binding units or peptides that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrin); or polypeptides in which the one or more immunoglobulin single variable domains are suitable linked to one or more small proteins or peptides that can bind to serum proteins (such as, without limitation, the proteins and peptides described in WO 91/01743, WO 01/45746, or WO 02/076489).

A preferred polypeptide of the invention comprises one or more immunoglobulin single variable domains against IL-6R, e.g. according to SEQ ID NO's: 1-10, in particular SEQ ID NO: 1, in combination with at least one binding domain or peptide suitable for extending serum half-life (preferably T½ß) of the construct. In these constructs, the "serum-albumin binding domain or peptide" may be any suitable serum-albumin binding peptide or binding domain capable of increasing the half-life (preferably T½ß) of the construct (compared to the same construct without the serum-albumin binding peptide or binding domain). Specifically, the polypeptide sequence suitable for extending serum half-life is a polypeptide sequence capable of binding to a serum protein with a long serum half-life, such as serum albumin, transferring, IgG, etc., in particular serum albumin. Polypeptide sequences capable of binding to serum albumin have previously been described and may in particular be serum albumin binding peptides as described in WO 08/068280 by applicant (and in particular WO 09/127691 and WO 2011/095545, both by applicant), or a serum albumin binding immunoglobulin single variable domains (such as a serum-albumin binding Nanobody; for example SEQ ID NOs 37-39, for which reference is for example made to WO 06/122787 and Table A-4).

As discussed above, in the polypeptides of the invention the one or more immunoglobulin single variable domain binding to IL-6R and the amino acid sequences or domains suitable for extending serum half-life can be fused with or without a linker, e.g. a peptide linker.

In a preferred polypeptide for use in the method of the invention one or more immunoglobulin single variable domains against IL-6R, e.g. according to SEQ ID NO's: 1-10, in particular SEQ ID NO: 1, is linked to a serum albumin binding immunoglobulin single variable domains, such as for example SEQ ID NO's: 37-39. Preferred polypeptides of the invention include SEQ ID NO's: 34-36, particularly SEQ ID NO: 34.

SEQ ID NO: 34 is a bivalent polypeptide consisting of 2 humanized and sequence-optimized immunoglobulin variable domains derived from heavy chain-only llama antibodies. One domain (SEQ ID NO: 1) binds to human IL-6R and the second domain (SEQ ID NO: 38) binds to human serum albumin (HSA), as a means to improve the PK properties of the polypeptide (half-life extension).

The polypeptides of the invention may be produced by a method comprising the following steps:
 a) expressing, in a suitable host cell or host organism or in another suitable expression system, a nucleic acid or nucleotide sequence, or a genetic construct encoding the polypeptide of the invention;
 optionally followed by:
 b) isolating and/or purifying the polypeptide of the invention thus obtained.

The method for producing the polypeptide of the invention may comprise the steps of:
 a) cultivating and/or maintaining a host or host cell under conditions that are such that said host or host cell expresses and/or produces at least one polypeptide of the invention, optionally followed by:
 b) isolating and/or purifying the polypeptide of the invention thus obtained.

According to one preferred, but non-limiting aspect of the invention, the polypeptide of the invention is produced in a bacterial cell, in particular a bacterial cell suitable for large scale pharmaceutical production.

According to another preferred, but non-limiting aspect of the invention, the polypeptide of the invention is produced in a yeast cell, in particular a yeast cell suitable for large scale pharmaceutical production.

According to yet another preferred, but non-limiting aspect of the invention, the polypeptide of the invention is produced in a mammalian cell, in particular in a human cell or in a cell of a human cell line, and more in particular in a human cell or in a cell of a human cell line that is suitable for large scale pharmaceutical production.

For production on industrial scale, preferred heterologous hosts for the (industrial) production of immunoglobulin single variable domains or immunoglobulin single variable domain-containing protein therapeutics include strains of E. coli, Pichia pastoris, S. cerevisiae that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

Subsequently, the polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the amino acid sequence to be isolated).

Pharmaceutical Compositions and Pharmaceutical Administration

Generally, for pharmaceutical use, the polypeptides of the invention may be formulated as a pharmaceutical preparation, compositions or formulations (used interchangeably) comprising at least one polypeptide of the invention and at least one pharmaceutically acceptable carrier, diluent or excipient and/or adjuvant, and optionally one or more further pharmaceutically active polypeptides and/or compounds. Such a formulation should be in a form suitable for subcutaneous administration.

The polypeptides of the invention can be formulated in any suitable manner which is suitable for subcutaneous administration known per se, for which reference is for example made to the general background patent and non-patent publications cited above (and in particular to WO 04/041862, WO 04/041863, WO 04/041865 and WO 04/041867) as well as to the standard handbooks, such as Remington's Pharmaceutical Sciences, 18$^{th}$ Ed., Mack Publishing Company, USA (1990) or Remington, the Science and Practice of Pharmacy, 21th Edition, Lippincott Williams and Wilkins (2005).

Preparations for subcutaneous administration may for example be sterile solutions, suspensions, dispersions or emulsions that are suitable for infusion or injection. Suitable carriers or diluents for such preparations for example include, without limitation, sterile water and aqueous buffers (such as e.g. histidine or citrate buffers) and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The invention, however, also encompasses products obtainable by further processing of a liquid formulation, such as a frozen, lyophilized or spray dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have characteristics that are defined by the features specified for liquid formulations herein. The invention does not exclude reconstitution that leads to a composition that deviates from the original composition before e.g. freeze- or spray drying.

Sterile injectable solutions are prepared by incorporating the polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Preferred pharmaceutical compositions for use with the polypeptides of the invention are been described in WO 2011/026948 and include, without being limiting, histidine buffer at pH 6.5, sucrose and polysorbate 80 (such as e.g. 15 mM histidine buffer pH 6.5, 8% sucrose and 0.01% polysorbate 80).

Generally, the concentration of the polypeptides of the invention in a liquid composition, such as an injectable preparation, will be from about 0.1-25 wt-%, preferably from about 0.5-10 wt-%, although the amounts are not limited to these ranges and may be higher or lower weight percentages depending on the need for higher or lower doses that can be administered in a volume that is suitable.

As demonstrated herein in the working examples, concentrations of 150 mg/mL have been used for subcutaneous administration of the polypeptide of the invention. It is expected that other concentrations having values around these concentrations (and also outside these values, i.e., higher or lower than these values) therefore also can be used. For example, concentrations of 10, 20, 25, 30, 40, 50, 60, 70, 80, 90, 100, 120, 150 mg/mL or more can be used.

Pre-filled syringes are highly suitable for subcutaneous administration of therapeutics. In one aspect therefore, the pharmaceutical composition is loaded into a pre-filled syringe. Accordingly, the present invention also relates to a pre-filled syringe containing a pharmaceutical composition comprising the polypeptide of the invention. In a preferred aspect, the pre-filled syringe contains a pharmaceutical composition that comprises SEQ ID NO: 34. The polypeptide (such as SEQ ID NO: 34) of the invention can be present in the pre-filled syringe at any suitable concentration such as 10, 20, 25, 30, 40, 50, 60, 70, 80, 90, 100, 120, 150 mg/mL or more. In a preferred aspect, the polypeptide of the invention (such as SEQ ID NO: 34) is present in the pre-filled syringe at a concentration of 150 mg/mL.

Various volumes of pre-filled syringes can be used. For use in the method of the present invention, the volume of the pre-filled syringe is preferably from 0.25 to 5.0 ml, such as from 0.25 to 2 ml, most preferably from 0.5 to 1 ml, such as 0.5 ml or 1 ml.

To obtain the efficacy of treatment as described herein, the polypeptide of the invention is administered at a dose of 75-300 mg. The desired dose may conveniently be presented in a single dose or as divided doses, for example, as two separate subcutaneous injections. For example, for the administration of a dose of 75 mg, one single injection can be used with a 0.5 ml pre-filled syringe comprising the polypeptide of the invention at a concentration of 150 mg/mL. For the administration of a dose of 150 mg, one single injection can be used with a 1 ml pre-filled syringe comprising the polypeptide of the invention at a concentration of 150 mg/mL. For the administration of a dose of 225 mg, two injections can be used, one with a 0.5 mL pre-filled syringe and one with a 1 ml pre-filled syringe respectively, each pre-filled syringe comprising the polypeptide of the invention at a concentration of 150 mg/mL. For the administration of a dose of 300 mg, two injections can be used, each with a 1 ml pre-filled syringe comprising the polypeptide of the invention at a concentration of 150 mg/mL.

In one aspect, the polypeptide of the invention is administered subcutaneously every week (weekly). Based on the bioavailability study as described in the examples section, a preferred dose for weekly subcutaneous administration of the polypeptides is 75-150 mg, such as a weekly dose of 75 mg, 150-200 mg, such as a weekly dose of 150 mg, 200-250 mg, such as a weekly dose of 225 mg, or even 250-300 mg, such as a weekly dose of 300 mg, or at a dose equivalent thereto.

In one aspect, the polypeptide of the invention is administered subcutaneously every 2 weeks (biweekly). Based on the bioavailability study as described in the examples section, a preferred dose for biweekly subcutaneous administration of the polypeptides is 75-150 mg, such as a biweekly dose of 75 mg, 150-200 mg, such as a biweekly dose of 150 mg, 200-250 mg, such as a biweekly dose of 225 mg, or even 250-300 mg, such as a biweekly dose of 300 mg, or at a dose equivalent thereto.

In one aspect, the polypeptide of the invention is administered subcutaneously every 4 weeks (4 weekly). Based on the bioavailability study as described in the examples section, a preferred dose for 4 weekly subcutaneous administration of the polypeptides is 75-150 mg, such as a 4 weekly dose of 75 mg, 150-200 mg, such as a 4 weekly dose of 150 mg, 200-250 mg, such as a 4 weekly dose of 225 mg, or even 250-300 mg, such as a 4 weekly dose of 300 mg, or at a dose equivalent thereto.

In one aspect, the polypeptide of the invention is administered subcutaneously every month (monthly). Based on the bioavailability study as described in the examples section, a preferred dose for monthly subcutaneous administration of the polypeptides is 75-150 mg, such as a monthly dose of 75 mg, 150-200 mg, such as a monthly dose of 150 mg, 200-250 mg, such as a monthly dose of 225 mg, or even 250-300 mg, such as a monthly dose of 300 mg, or at a dose equivalent thereto.

The above doses are also referred to herein as the "selected dosing schedule(s)" or "selected dose regimen(s)".

Accordingly, the present invention relates to pre-filled syringe comprising the polypeptide of the invention for the treatment of an IL-6R related disease in a human subject, said method comprising subcutaneous administration to a human subject suffering the IL-6R related disease, of a polypeptide of the invention at the selected dosing schedule. More specifically, the present invention relates to pre-filled syringe comprising the polypeptide of the invention for the treatment of an IL-6R related disease in a human subject, said method comprising subcutaneous administration to a human subject suffering the IL-6R related disease, of a polypeptide of the invention at a dose of 75-300 mg every week to every month, or at a dose equivalent to 75-300 mg every week to every month.

In one aspect the polypeptide in the pre-filled syringe is administered at a dose of 75-300 mg every week or at a dose equivalent to 75-300 mg every week. In one aspect the polypeptide in the pre-filled syringe is administered at a dose of 75-150 mg every week or at a dose equivalent to 75-150 mg every week. In one aspect the polypeptide in the pre-filled syringe is administered at a dose of 75 mg every week or at a dose equivalent to 75 mg every week. In one aspect the polypeptide in the pre-filled syringe is administered at a dose of 150-200 mg every week or at a dose equivalent to 150-200 mg every week. In one aspect the polypeptide in the pre-filled syringe is administered at a dose of 150 mg every week or at a dose equivalent to 150 mg every week. In one aspect the polypeptide in the pre-filled syringe is administered at a dose of 200-250 mg every week or at a dose equivalent to 200-250 mg every week. In one aspect the polypeptide in the pre-filled syringe is administered at a dose of 225 mg every week or at a dose equivalent to 225 mg every week or at a dose equivalent to 225 mg every week. In one aspect the polypeptide in the pre-filled syringe is administered at a dose of 250-300 mg every week or at a dose equivalent to 250-300 mg every week. In one aspect the polypeptide in the pre-filled syringe is administered at a dose of 300 mg every week or at a dose equivalent to 300 mg every week.

In one aspect the polypeptide in the pre-filled syringe is administered at a dose of 75-300 mg every 2 weeks or at a dose equivalent to 75-300 mg every 2 weeks. In one aspect the polypeptide in the pre-filled syringe is administered at a dose of 75-150 mg every 2 weeks or at a dose equivalent to 75-150 mg every 2 weeks. In one aspect the polypeptide in the pre-filled syringe is administered at a dose of 75 mg every 2 weeks or at a dose equivalent to 75 mg every 2 weeks. In one aspect the polypeptide in the pre-filled syringe is administered at a dose of 150-200 mg every 2 weeks or at a dose equivalent to 150-200 mg every 2 weeks. In one aspect the polypeptide in the pre-filled syringe is administered at a dose of 150 mg every 2 weeks or at a dose equivalent to 150 mg every 2 weeks. In one aspect the polypeptide in the pre-filled syringe is administered at a dose of 200-250 mg every 2 weeks or at a dose equivalent to 200-250 mg every 2 weeks. In one aspect the polypeptide in the pre-filled syringe is administered at a dose of 225 mg every 2 weeks or at a dose equivalent to 225 mg every 2 weeks. In one aspect the polypeptide in the pre-filled syringe is administered at a dose of 250-300 mg every 2 weeks or at a dose equivalent to 250-300 mg every 2 weeks. In one aspect the polypeptide in the pre-filled syringe is administered at a dose of 300 mg every 2 weeks or at a dose equivalent to 300 mg every 2 weeks.

In one aspect the polypeptide in the pre-filled syringe is administered at a dose of 75-300 mg every 4 weeks or at a dose equivalent to 75-300 mg every 4 weeks. In one aspect the polypeptide in the pre-filled syringe is administered at a dose of 75-150 mg every 4 weeks or at a dose equivalent to 75-150 mg every 4 weeks. In one aspect the polypeptide in the pre-filled syringe is administered at a dose of 75 mg every 4 weeks or at a dose equivalent to 75 mg every 4 weeks. In one aspect the polypeptide in the pre-filled syringe is administered at a dose of 150-200 mg every 4 weeks or at a dose equivalent to 150-200 mg every 4 weeks. In one aspect the polypeptide in the pre-filled syringe is administered at a dose of 150 mg every 4 weeks or at a dose equivalent to 150 mg every 4 weeks. In one aspect the polypeptide in the pre-filled syringe is administered at a dose of 200-250 mg every 4 weeks or at a dose equivalent to 200-250 mg every 4 weeks. In one aspect the polypeptide in the pre-filled syringe is administered at a dose of 225 mg every 4 weeks or at a dose equivalent to 225 mg every 4 weeks. In one aspect the polypeptide in the pre-filled syringe is administered at a dose of 250-300 mg every 4 weeks or at a dose equivalent to 250-300 mg every 4 weeks. In one aspect the polypeptide in the pre-filled syringe is administered at a dose of 300 mg every 4 weeks or at a dose equivalent to 300 mg every 4 weeks.

In one aspect the polypeptide in the pre-filled syringe is administered at a dose of 75-300 mg every month or at a dose equivalent to 75-300 mg every month. In one aspect the polypeptide in the pre-filled syringe is administered at a dose of 75-150 mg every month or at a dose equivalent to 75-150 mg every month. In one aspect the polypeptide in the pre-filled syringe is administered at a dose of 75 mg every month or at a dose equivalent to 75 mg every month. In one aspect the polypeptide in the pre-filled syringe is administered at a dose of 150-200 mg every month or at a dose equivalent to 150-200 mg every month. In one aspect the polypeptide in the pre-filled syringe is administered at a dose of 150 mg every month or at a dose equivalent to 150 mg every month. In one aspect the polypeptide in the pre-filled syringe is administered at a dose of 200-250 mg every month or at a dose equivalent to 200-250 mg every month. In one aspect the polypeptide in the pre-filled syringe is administered at a dose of 225 mg every month or at a dose equivalent to 225 mg every month. In one aspect the polypeptide in the pre-filled syringe is administered at a dose of 250-300 mg every month or at a dose equivalent to 250-300 mg every month. In one aspect the polypeptide in the pre-filled syringe is administered at a dose of 300 mg every month or at a dose equivalent to 300 mg every month.

In one aspect, the human subject is suffering from rheumatoid arthritis. In one aspect, the human subject is suffering from active rheumatoid arthritis. In one aspect, the human subject is suffering from active rheumatoid arthritis despite methotrexate therapy. In one aspect, the human subject is suffering from rheumatoid arthritis and is intolerant to MTX. In one aspect, the human subject is suffering from rheumatoid arthritis and continuation of MTX treatment is inappropriate.

In one aspect, the human subject is suffering from systemic lupus erythematosus. In one aspect, the human subject is suffering from moderate to severe active systemic lupus erythematosus.

Method of the Invention

The present invention provides methods and dosing schedules for subcutaneous administration of polypeptides that bind and block IL-6R. As such, these methods and dosing schedules can be used for the prevention and treatment (as defined herein) of diseases and/or disorders related to IL-6 mediated signaling, also referred to herein as IL-6R related diseases.

Generally, "diseases and/or disorders related to IL-6 mediated signaling" can be defined as diseases and/or disorders that can be prevented and/or treated, respectively, by suitably administering to a subject in need thereof (i.e. having the disease and/or disorder or at least one symptom thereof and/or at risk of attracting or developing the disease or disorder) of either a polypeptide of the invention (and in particular, of a pharmaceutically active amount thereof) and/or of a known active principle active against IL-6, IL-6R, the IL-6/IL-6R complex (optionally in further complex with gp130) or a biological pathway or mechanism in which IL-6 and IL-6R are involved (and in particular, of a pharmaceutically active amount thereof).

Diseases and/or disorders related to IL-6 mediated signaling encompass diseases and disorders associated with IL-6R, with IL-6, with the IL-6/IL-6R complex (optionally in further complex with gp130), and/or with the signaling pathway(s) and/or the biological functions and responses in which IL-6, IL-6R and/or the IL-6/IL-6R complex (optionally in further complex with gp130) are involved, and in particular diseases and disorders associated with IL-6R, with IL-6, with the IL-6/IL-6R complex (optionally in further complex with gp130), and/or with the signaling pathway(s) and/or the biological functions and responses in which IL-6R, IL-6 and/or the IL-6/IL-6R complex (optionally in further complex with gp130) are involved, which are characterized by excessive and/or unwanted signaling mediated by IL-6 or by the pathway(s) in which IL-6 is involved. Such diseases and disorders are also generally referred to herein as "IL-6R related diseases".

The invention thus also relates to a polypeptide of the invention for the prevention and treatment (as defined herein) of these "IL-6R related diseases" and/or "diseases and/or disorders related to IL-6 mediated signaling" wherein the polypeptide is administered subcutaneously at the dosing schedule provided by the present invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be a human being. As will be clear to the skilled person, the subject to be treated will in particular be a person suffering from, or at risk of, the diseases and/or disorders mentioned herein. For example, the subject may be a person suffering from, or at risk of, a disease and/or disorder related to IL-6 mediated signaling and/or a disease in which IL-6R activity is detrimental.

In one aspect, the subject treated is a person suffering from rheumatoid arthritis (RA). More specifically, the subject treated is a person diagnosed with RA according to the 2010 European League Against Rheumatism [EULAR]/American College of Rheumatology [ACR] classification criteria.

In one aspect, the subject treated has an ACR functional class I-III.

In one aspect, the subject treated is suffering from moderate to severe RA.

In one aspect, the subject treated is suffering from active RA. Active RA is defined in the present invention by persistent disease activity with at least 6 swollen and 6 tender joints (66/68-joint count), at the time of screening and baseline, and C-reactive protein (CRP)≤1.2× upper limit of normal (ULN) at screening.

In one aspect, the subject treated is suffering from active RA despite methotrexate therapy.

In one aspect, the subject has received previous or current treatment with MTX, and is considered intolerant to MTX, and/or for whom continued treatment with MTX is considered inappropriate, or has contraindications for MTX use. Patients and physicians may discontinue MTX-treatment for a number of reasons, including gastrointestinal, hepatic, dermatologic as well as neurologic AEs. Accordingly, the subject treated is a person suffering from RA and intolerant to MTX and/or the human subject treated is suffering from RA for whom continuation of MTX treatment is inappropriate.

In another aspect, the subject treated is a person suffering from systemic lupus erythematosus (SLE). More specifically, the subject treated is a person diagnosed with SLE and who fulfills the 1997 ACR or 2012 SLICC classification criteria.

In one aspect, the subject treated is suffering from moderate to severe active SLE. Moderate to severe active SLE is defined by SLEDAI-2K score 6. Accordingly, in one aspect, the subject treated has a SLEDAI-2K score of 6 or more.

In one aspect, the subject treated has seropositive disease at screening for ANA (≥1:80) and/or anti-dsDNA (≥30 IU/ml).

In one aspect, the subject has renal involvement wherein proteinuria is 1 g/day or less or 1 g/day or more (measured, for example, by spot urine protein to creatinine ratio of 1 mg/mg) and the estimated Glomerular Filtration Rate (MDRD) is above 60 mL/min/1.73 m².

The polypeptide of the invention is administered subcutaneously at a dose of 75-300 mg every week to every month or at a dose equivalent to 75-300 mg every week to every month. The desired dose may conveniently be presented in a single dose or as divided doses, for example, as two separate subcutaneous injections (as described above).

In one aspect, the polypeptide of the invention is administered subcutaneously every week (weekly). Based on the bioavailability study as described in the examples section, a preferred dose for weekly subcutaneous administration of the polypeptides is 75-150 mg, such as a weekly dose of 75 mg or a dose equivalent to 75 mg every week. Another preferred dose for weekly subcutaneous administration of the polypeptides is 150-200 mg, such as a weekly dose of 150 mg or a dose equivalent to 150 mg every week. Another preferred dose for weekly subcutaneous administration of the polypeptides is 200-250 mg, such as a weekly dose of 225 mg or a dose equivalent to 225 mg every week. Another preferred dose for weekly subcutaneous administration of the polypeptides is 250-300 mg, such as a weekly dose of 300 mg or a dose equivalent to 300 mg every week.

Accordingly, the present invention relates to a method and a polypeptide of the invention for treatment of an IL-6R related disease, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week.

As such, the present invention relates to a method and a polypeptide of the invention for treatment of RA, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week. The present invention relates to a method and a polypeptide of the invention for treatment of active RA, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week. The present invention relates to a method and a polypeptide of the invention for treatment of active RA despite MTX therapy, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week.

As such, the present invention relates to a method and a polypeptide of the invention for treatment of SLE, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week. The present invention relates to a method and a polypeptide of the invention for treatment of moderate to severe active SLE, wherein the polypeptide of the invention is administered subcutaneously at a dose of 75-150 mg every week, such as a weekly dose of 75 mg or a dose equivalent to 75 mg every week, or 150-200 mg every week, such as a weekly dose of 150 mg or a dose equivalent to 150 mg every week, or 200-250 mg every week, such as a weekly dose of 225 mg or a dose equivalent to 225 mg every week, or 250-300 mg every week, such as a weekly dose of 300 mg or a dose equivalent to 300 mg every week.

In one aspect, the polypeptide of the invention is administered subcutaneously every 2 weeks (biweekly). Based on the bioavailability study as described in the examples section, a preferred dose for biweekly subcutaneous administration of the polypeptides is 75-150 mg, such as a biweekly dose of 75 mg or a dose equivalent to 75 mg every 2 weeks. Another preferred dose for biweekly subcutaneous administration of the polypeptides is 150-200 mg, such as a biweekly dose of 150 mg or a dose equivalent to 150 mg every 2 weeks. Another preferred dose for biweekly subcutaneous administration of the polypeptides is 200-250 mg, such as a biweekly dose of 225 mg or a dose equivalent to 225 mg every 2 weeks. Another preferred dose for biweekly subcutaneous administration of the polypeptides is 250-300 mg, such as a biweekly dose of 300 mg or a dose equivalent to 300 mg every 2 weeks.

Accordingly, the present invention relates to a method and a polypeptide of the invention for treatment of an IL-6R related disease, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks.

As such, the present invention relates to a method and a polypeptide of the invention for treatment of RA, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks. The present invention relates to a method and a polypeptide of the invention for treatment of active RA, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks. The present invention relates to a method and a polypeptide of the invention for treatment of active RA despite MTX therapy, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks.

As such, the present invention relates to a method and a polypeptide of the invention for treatment of SLE, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks. The present invention relates to a method and a polypeptide of the invention for treatment of moderate to severe active SLE, wherein the polypeptide of the invention is administered subcutaneously at a dose of 75-150 mg every two weeks, such as a biweekly dose of 75 mg or a dose equivalent to 75 mg every two weeks, or 150-200 mg every two weeks, such as a biweekly dose of 150 mg or a dose equivalent to 150 mg every two weeks, or 200-250 mg every two weeks, such as a biweekly dose of 225 mg or a dose equivalent to 225 mg every two weeks, or 250-300 mg every two weeks, such as a biweekly dose of 300 mg or a dose equivalent to 300 mg every two weeks.

In one aspect, the polypeptide of the invention is administered subcutaneously every 4 weeks (4 weekly). Based on the bioavailability study as described in the examples section, a preferred dose for 4 weekly subcutaneous administration of the polypeptides is 75-150 mg, such as a 4 weekly dose of 75 mg or a dose equivalent to 75 mg every 4 weeks. Another preferred dose for 4 weekly subcutaneous administration of the polypeptides is 150-200 mg, such as a 4 weekly dose of 150 mg or a dose equivalent to 150 mg every 4 weeks. Another preferred dose for 4 weekly subcutaneous administration of the polypeptides is 200-250 mg, such as a 4 weekly dose of 225 mg or a dose equivalent to 225 mg every 4 weeks. Another preferred dose for 4 weekly subcutaneous administration of the polypeptides is 250-300 mg, such as a 4 weekly dose of 300 mg or a dose equivalent to 300 mg every 4 weeks.

Accordingly, the present invention relates to a method and a polypeptide of the invention for treatment of an IL-6R related disease, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks.

As such, the present invention relates to a method and a polypeptide of the invention for treatment of RA, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks. The present invention relates to a method and a polypeptide of the invention for treatment of active RA, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks. The present invention relates to a method and a polypeptide of the invention for treatment of active RA despite MTX therapy, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks.

As such, the present invention relates to a method and a polypeptide of the invention for treatment of SLE, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks. The present invention relates to a method and a polypeptide of the invention for treatment of moderate to severe active SLE, wherein the polypeptide of the invention is administered subcutaneously at a dose of 75-150 mg every four weeks, such as a 4 weekly dose of 75 mg or a dose equivalent to 75 mg every 4 weeks, or 150-200 mg every four weeks, such as a 4 weekly dose of 150 mg or a dose equivalent to 150 mg every 4 weeks, or 200-250 mg every four weeks, such as a 4 weekly dose of 225 mg or a dose equivalent to 225 mg every 4 weeks, or 250-300 mg every four weeks, such as a 4 weekly dose of 300 mg or a dose equivalent to 300 mg every 4 weeks.

In one aspect, the polypeptide of the invention is administered subcutaneously every month (monthly). Based on the bioavailability study as described in the examples section, a preferred dose for monthly subcutaneous administration of the polypeptides is 75-150 mg, such as a monthly dose of 75 mg or a dose equivalent to 75 mg every month. Another preferred dose for monthly subcutaneous administration of the polypeptides is 150-200 mg, such as a monthly dose of 150 mg or a dose equivalent to 150 mg every month. Another preferred dose for monthly subcutaneous administration of the polypeptides is 200-250 mg, such as a monthly dose of 225 mg or a dose equivalent to 225 mg every month. Another preferred dose for monthly subcutaneous administration of the polypeptides is 250-300 mg, such as a monthly dose of 300 mg or a dose equivalent to 300 mg every month.

Accordingly, the present invention relates to a method and a polypeptide of the invention for treatment of an IL-6R related disease, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month.

As such, the present invention relates to a method and a polypeptide of the invention for treatment of RA, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month. The present invention relates to a method and a polypeptide of the invention for treatment of active RA, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month. The present invention relates to a method and a polypeptide of the invention for treatment of active RA despite MTX therapy, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month.

As such, the present invention relates to a method and a polypeptide of the invention for treatment of SLE, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month. The present invention relates to a method and a polypeptide of the invention for treatment of moderate to severe active SLE, wherein the polypeptide of the invention is administered subcutaneously at a dose of 75-150 mg every month, such as a monthly dose of 75 mg or a dose equivalent to 75 mg every month, or 150-200 mg every month, such as a monthly dose of 150 mg or a dose equivalent to 150 mg every month, or 200-250 mg every month, such as a monthly dose of 225 mg or a dose equivalent to 225 mg every month, or 250-300 mg every month, such as a monthly dose of 300 mg or a dose equivalent to 300 mg every month.

The above dose regimens are also referred to herein as the "selected dosing schedules" or "selected dose regimens".

In a preferred aspect the polypeptide of the invention is SEQ ID NO: 34.

In the method of the present invention the polypeptide of the invention, such as SEQ ID NO: 34, is administered subcutaneously to subjects suffering the IL-6R related disease, such as e.g. RA or SLE, at the selected dosing schedules such that treatment occurs.

Various biomarkers are available for measuring IL-6 mediated signaling and inhibition of IL-6R activity. In a preferred aspect, markers of IL-6 mediated signaling are selected from soluble interleukin-6 receptor (sIL-6R), interleukin-6 (IL-6), C-reactive protein (CRP), fibrinogen, anti-dsDNA, complement C3, complement C4, and complement CH50. These markers can be measured using standard methods known to and used by the skilled person, such as various immunologically based assays, including enzyme-linked immunosorbent assays (ELISA; also known as an enzyme immunoassay (EIA)), radioimmunoassays or immunoenzymetric assays. Chemical, colorimetric and enzymatic based assays also may be used when suitable.

Soluble IL-6R (sIL-6R) includes (plasma) sIL-6R free from IL-6 and (plasma) sIL-6R free from polypeptide of the invention as well as (plasma) sIL-6R in complex with IL-6, (plasma) sIL-6R in complex with IL-6 and (plasma) sIL-6R in an immune complex with the polypeptide of the invention. Plasma sIL-6R is free or bound to IL-6 before administration of the polypeptide of the invention. Following administration of the polypeptide of the invention, the sIL-6R binds to the polypeptide of the invention to form a sIL-6R/polypeptide of the invention immune complex.

sIL-6R and/or plasma sIL-6R levels can be determined by any method as described herein and/or known in the art. Preferred methods for determining sIL-6R levels include immunoassays such as flow cytometry, inhibition assay, immunoprecipitation, immunohistochemistry (Frozen) and ELISA (such as e.g. the QUANTIKINE® Human IL-6sR kit from R&D Systems, Minneapolis, Minn.; E91815Hu ELISA Kit for Interleukin 6 Receptor (IL6R) from Uscn Life Science Inc, Wuhan, China; SEK10398 human IL6R/CD126 ELISA kit from Sino Biological, Inc., Beijing, China; EL10034 Interleukin 6 Soluble Receptor (IL 6 sR) ELISA Kit, human from Biosupply, UK; or any other assay such as e.g. the assays described in the example section).

IL-6 includes serum IL-6 free from IL-6R as well as serum IL-6 in complex with IL-6R. Serum IL-6 levels are free or bound to IL-6R before administration of the polypeptide of the invention. Following administration of the polypeptide of the invention IL-6 temporarily increases. This increase is most likely caused by IL-6R blockade inhibiting clearance of IL-6 from the blood.

Serum IL-6 levels can be determined by any method as described herein and/or known in the art. Preferred methods for determining IL-6 levels include immunoassays such as flow cytometry, inhibition assay, immunoprecipitation, immunohistochemistry (Frozen) and ELISA (such as e.g. Human IL-6 QUANTIGLO® ELISA Kit" from R&D Systems, Minneapolis, Minn. (cat #Q6000B); Human IL-6 ELISA READY-SET-GO!® from eBioscience Ltd., Hatfield, United Kingdom; Human Interleukin-6 (IL6/IFNB2) ELISA Kit from Sino Biological Inc., Beijing, China; Interleukin 6 (IL 6) ELISA Kit, human from Biosupply, UK).

C-reactive protein (CRP) is an acute-phase protein found in the blood, of which the levels rise in response to inflammation. CRP is synthesized by hepatocytes as a direct effect of IL-6 stimulation. Elevated CRP levels are an indication of inflammation intensity in RA. It has been demonstrated that blockade of IL-6 mediated signaling (such as by blockade of IL-6R) can lower CRP levels (Nishimoto et al. 2008, Blood 112: 3959-3964).

The level of CRP in serum can be determined by any method as described herein and/or known in the art. Methods include (without being limiting) immunoassays such as the C-reactive protein detection kit (Difco Laboratories, Detroit, Mich., US), the Human C-Reactive Protein ELISA Kit (Abnova Corporation, Taipei, Taiwan R.O.C.), the Human CRP ELISA Kit, High sensitivity (American Diagnostic GmbH, Pfungstadt, Germany), the Human CRP ELISA Kit (Antigenix America Inc., NY, US) and the IMMAGE® Immunochemistry System (Beckman Coulter Inc., Brea, Calif., US; Kit Recorder #447280).

Erythrocytye Sedimentation Rate (ESR) is the rate at which red blood cells sediment in a period of 1 hour. It is a common hematology test, and is a non-specific measure of inflammation. To perform the test, anticoagulated blood is placed in an upright tube, known as a Westergren tube, and the rate at which the red blood cells fall is measured and reported in mm/h. The ESR is governed by the balance between pro-sedimentation factors, mainly fibrinogen, and those factors resisting sedimentation, namely the negative charge of the erythrocytes (zeta potential). When an inflammatory process is present, the high proportion of fibrinogen in the blood causes red blood cells to stick to each other. The red cells form stacks called 'rouleaux', which settle faster.

The ESR can further be determined (without being limiting) with the Greiner ESR tube (Cat. No. 454076), or with the Preanalytics—VACUETTE® Evacuated Collection Tubes (Greiner Bio-One, Wemmel, Belgium), with SEDIPLUS® S 2000 (Sarstedt; Nümbrecht, Germany), or with SEDITAINER™ (Product Number: 366016; Becton Dickinson, N.J. USA).

Fibrinogen (factor I) is a soluble 340 kDa glycoprotein, synthesized in the liver by hepatocytes, that is converted by thrombin into fibrin during blood coagulation. The concentration in blood plasma is 1.5-4.0 g/L (normally measured using the Clauss method) or about 7 µM. Recent research has shown that fibrin plays a key role in the inflammatory response and development of rheumatoid arthritis. It may be elevated in any form of inflammation, as it is an acute-phase protein (Gilliam et al. 2011, Pediatric Rheumatology 9: 8).

The fibrinogen level can be determined by any method as described herein and/or known in the art. Methods include (without being limiting) the STA® Fibrinogen 5 (Stago, Parsippany, N.J., USA) for quantitative determination of fibrinogen by the Clauss method, the STA COMPACT®, a fully automated, benchtop, Haemostasis analyser for clotting, chromogenic and immunological assays using random access mode (Stago, Parsippany, N.J., USA), ACL TOP® 500 CTS (Beckman Coulter Inc., Brea, Calif., US) and CEVERON® alpha (TC technoclone, Vienna, Austria).

Anti-dsDNA antibodies are a group of anti-nuclear antibodies and their target antigen is double stranded DNA. Blood tests such as enzyme-linked immunosorbent assay (ELISA) and immunofluorescence are routinely performed to detect anti-dsDNA antibodies in diagnostic laboratories. They are highly diagnostic of systemic lupus erythematosus (SLE) and are implicated in the pathogenesis of lupus nephritis.

Anti-dsDNA antibodies can be determined by any method as described herein and/or known in the art. Methods include (without being limiting) the Farr assay (Egner 2000, J. Clin.

Pathol. 53: 424-32), polyethylene glycol (PEG) assay precipitation (Nossent et al. 1989, Ann. Rheum. Dis. 48: 748-52), the use of HEp-2 cells (Bradwell 2003 Atlas of HEp-2 patterns and laboratory techniques. Birmingham: Binding Site. ISBN 0-7044-2437-1), Crithidia (Slater et al. 1976, Clin. Exp. Immunol. 25: 480-6), an EIA detecting antibodies using a DNA-coated polystyrene microtitre plate, flow cytometry or Multiplex immunoassay (MIA) (Yu et al. 2011, Ann. Biol. Clin. 69: 17-29; Kumar et al. 2009, Diagn. Pathol. 4: 1), or Microarrays (Hueber et al. 2002, Arthritis Res. 4: 290-5). The DNA used in these assays is often recombinant dsDNA or from calf thymus extract (Burnett and Crocker 1999, The Science of Laboratory Diagnosis. ISIS Medical Media. pp. 494-495).

The complement system is an integral part of the immune defenses. It can be activated via immune complexes (classic pathway) or by bacterial polysaccharides (alternative pathway). The classic complement pathway consists of recognition, (C1q, C1r, C1s), activation (C2, C3, C4), and attack (C5, C6, C7, C8, C9) mechanisms with respect to their role in antibody-mediated cytolysis.

C3 and C4 are one of the activation proteins of the classic pathway. Levels of C3 in the blood may be measured to support or refute a particular medical diagnosis. For example, low C3 levels are associated with some types of kidney disease such as post-infectious glomerulonephritis and shunt nephritis.

Complement component 3 can be determined by any method as described herein and/or known in the art. Methods include (without being limiting) the Human Complement C3 ELISA Kit from Assaypro LLC, MO, US (Cat #EC2101-1), the Complement C3 Human ELISA kit from Abcam, Cambridge, UK (Cat #ab108823), and Human Complement C3 ELISA Quantitation Kit from GenWay, San Diego, Calif. (Cat #GWB-1C0767).

Complement component 4 can be determined by any method as described herein and/or known in the art. Methods include (without being limiting) the AssayMax Human Complement C4 ELISA Kit from Assaypro LLC, MO, US (Cat #EC2102-1), the Complement C4 Human ELISA kit from Abcam, Cambridge, UK (Cat #ab108824), and ELISA Kit for Complement Component 4 from Uscn Life Science, Inc. (Cat #SEA888Hu).

Total complement activity (CH50) is a test performed to assess the level of functioning of the complement system. The Autokit CH50 Wako Diagnostics, Mountain View, Calif., US (Cat #995-40801), e.g., is an in vitro liposome immunoassay (LIA) for the quantitative determination of total complement activity in human serum (CH50).

The efficacy of the RA treatment (i.e. therapeutic effect) can be determined by various parameters including (without being limiting), ACR 20, 50, 70 and 90 response over time, ACR-N index of improvement over time, DAS 28 (using CRP and ESR) score over time, proportion of subjects with EULAR response over time, proportion of subjects in remission over time (making use of following definitions: DAS28, CDAI, SDAI, Boolean remission), including inhibition of structural damages, change from baseline in disease activity over time (making use of following disease activity scores (DAS28, SDAI, CDAI), change from baseline in HAQ-DI over time, the proportion of HAQ-DI responders over time, the changes from baseline in the physical and mental component scores of the SF-36, the change from baseline in FACIT-F, duration of morning stiffness.

The ACR responses are a broadly accepted clinical response measure to demonstrate reduction in RA signs and symptoms and sensitive enough to differentiate from placebo effects. ACR responses are presented as the numerical measurement of improvement in multiple disease assessment criteria. ACR20/50/70/90 responses are defined as below (2010 European League Against Rheumatism (EULAR)/American College of Rheumatology (ACR) classification criteria):

≥20/50/70/90% improvement in tender/painful joint count (TJC) (68 joints) relative to baseline AND
≥20/50/70% improvement in swollen joint count (SJC) (66 joints) relative to baseline AND
≥20/50/70% improvement in 3 of the following 5 areas relative to baseline:
  Patient's Assessment of Pain (100 mm-VAS).
  Patient's Global Assessment of Disease Activity (100 mm-VASPA).
  Physician's Global Assessment of Disease Activity (100 mm-VASPHA).
  Patient's assessment of physical function as measured by the Health Assessment Questionnaire Disability Index (HAQ-DI).
  C-reactive protein (CRP).

The ACR-N Index of Improvement (Williams 1991, J. Fla. Med. Assoc. 78: 517-519; Abdel-Razzak et al. 1993, 44: 707-715) is defined as the minimum of the following 3 criteria:

The percent improvement from baseline in tender joint counts (TJCs).
The percent improvement from baseline in swollen joint (SJCs).
The median percent improvement from baseline for the following 5 assessments:
  Patient's assessment of pain (VAS).
  Patient's global assessment of disease activity (VASPA).
  Physician's global assessment of disease activity (VASPHA).
  Patient's assessment of physical function as measured by the HAQ-DI.
  CRP.

Patient's assessment of pain (100 mm-VAS) can be performed by asking the subject: "How much pain have you had because of your condition over the past week?" and then instructing to place a mark between 0 ("no pain") and 100 mm ("pain as bad it could be") on the VAS scale to indicate how severe the pain has been.

Patient's Global Assessment of Disease Activity (100 mmm-VASPA) can be performed by instructing the subject as follows: "Considering all the ways in which illness and health conditions may affect you at this time, please make a mark between 0 ("very well") and 100 mm ("very bad") on the VAS scale to show how you are doing."

Physician's Global Assessment of Disease Activity (100 mm-VASPHA) can be performed by asking the physician to make a mark between 0 ("very good") and 100 mm ("very bad") on the VAS scale to indicate disease activity (independent of the subject's self-assessment).

Health Assessment Questionnaire Disability Index (HAQ-DI) is a 20-question instrument which assesses the degree of difficulty the subject had in accomplishing tasks in 8 functional areas (dressing and grooming, arising, eating, walking, hygiene, reaching, gripping, and errands and chores) over the previous week, Within each category, subjects report the amount of difficulty they have in performing the specific sub-category items. There are four response options ranging from: 0=No Difficulty; 1=With Some Difficulty; 2=With Much Difficulty; 3=Unable to Do.

Physical and mental component scores of Short Form (SF-36) consists of 36 items that can be summarized into 8 domains: physical functioning, role limitations due to physical health problems (role-physical), bodily pain, general health, vitality, social functioning, role limitations due to emotional problems (role-emotional), and mental health. Two summary measures, the physical component summary and the mental component summary, can be derived based on these domain scores. The concepts measured by the SF-36 are not specific to any disease, allowing comparison of relative burden of different diseases, in addition to the relative benefit of different treatments.

Functional Assessment of Chronic Illness Therapy-Fatigue (FACIT-F or FACIT-Fatigue) is a collection of health-related quality of life questionnaires that assess multidimensional health status in people with various chronic illnesses, including RA.

The DAS28 based on erythrocyte sedimentation rate (ESR) is a statistically derived index combining TJC (28 joints), SJC (28 joints), ESR, and VASPA (Briso et al. 2008, J. Immunol., 180: 7102-7106). CRP can be used as alternative to ESR in the calculation of DAS28. CRP is a more direct measure of inflammation than ESR, and it is more sensitive to short-term changes. CRP is considered at least as valid as ESR to measure RA disease activity. As such, the DAS28 using CRP is a statistically derived index combining TJC (28 joints), SJC (28 joints), CRP, and VASPA.

Cut-off points for DAS28 (ESR) to define if a subject is in clinical remission or in a state of high, moderate, or low disease activity have been defined (Betz and W. Muller 1998, Int. Immunol. 10: 1175-1184):

| High disease activity | DAS28 > 5.1 |
| Moderate disease activity | 3.2 < DAS28 ≤ 5.1 |
| Low disease activity | 2.6 ≤ DAS28 ≤ 3.2 |
| Remission | DAS28 < 2.6 |

Boolean remission is determined according to following criteria (Felson et al. 2011, American College of Rheumatology/European League against Rheumatism provisional definition of remission in rheumatoid arthritis for clinical trials. Annals of the rheumatic diseases 70: 404-13):
If TJC28≤1 and SJC28≤1 and VASPA (cm)≤1 and CRP (mg/dL)≤1
  Then remission="yes"
  Else remission="no"

The CDAI clinical score is determined according to following criteria (Felson, et al. 2011; Aletaha and Smolen 2007, Clinical rheumatology 21: 663-75):
Calculation of CDAI Score: CDAI=TJC28+SJC28+VASPA+VASPHA
Classification of CDAI Score:

| CDAI Score | CDAI ≤ 2.8 | 2.8 < CDAI ≤ 10 | 10 < CDAI ≤ 22 | 22 < CDAI |
|---|---|---|---|---|
| Disease Activity | remission | low disease activity | moderate disease activity | high disease activity |

The SDAI clinical score is determined according to following criteria (Aletaha and Smolen 2007):
Calculation of SDAI Score: SDAI=TJC28+SJC28+VASPA+VASPHA+CRP
Classification of SDAI Score:

| SDAI Score | SDAI ≤ 3.3 | 3.3 < SDAI ≤ 11.0 | 11.1 < SDAI ≤ 26.0 | SDAI > 26.0 |
|---|---|---|---|---|
| Disease Activity | remission | low disease activity | moderate disease activity | high disease activity |

EULAR response is assessed by comparing a subject's DAS28 score (using CRP and ESR) relative to baseline as follows:

| | Improvement in DAS28 Relative to Baseline | | |
|---|---|---|---|
| Present DAS28 | >1.2 | >0.6 and ≤1.2 | ≤0.6 |
| ≤3.2 | good response | moderate response | no response |
| >3.2 and ≤5.1 | moderate response | moderate response | no response |
| >5.1 | moderate response | no response | no response |

The efficacy of the treatment of subject suffering from SLE can be determined by the percentage of subjects who achieved a response. The response can be measured by the SLE Responder Index (SRI). SRI response can be defined as:
  Reduction from baseline in Systemic Lupus Erythematosus Disease Activity Index 2000 (SLEDAI-2K; Gladman et al. 2002, J. Rheumatol. 29: 288-91) of ≥4 points;
  No new A score and no more than one new B score on the British Isles Lupus Assessment Group's (BILAG 2004) disease activity index (Isenberg et al. 2005, Rheumatology 44: 902-6) compared with baseline;
  No increase in the Physician Global Assessment score of 0.3 point on a Visual Analogue Scale (VAS) of 0-3;
The response can also be measured by the modified SLE Responder Index (mSRI). mSRI response can be defined as:
  Reduction from baseline in modified SLEDAI-2K (mSLEDAI-2K) of ≥4 points;
  No new A score and no more than one new B score on the BILAG-2004 compared with baseline;
  No increase in the Physician Global Assessment score of 0.3 point on a Visual Analogue Scale (VAS) of 0-3;
A modified SLEDAI-2K index can be derived from the standard index by omitting 1 of the standard items (low complement). An anti-IL-6 compound strongly decreases production of acute phase reactants, including complement. (Illei 2010, Arthritis Rheum. 62: 542-52; Szepietowski 2013, Arthritis Rheum. 65: 2661-71). Therefore, the C¾ values (parameters of the low complement item in the SLEDAI-2K index) may be decreased due to decreased production while effect on complement consumption (relevant for disease activity evaluation) cannot be assessed.

Efficacy can also be determined by the change from baseline in mSLEDAI-2K total score as well as standard SLEDAI-2K measured over time.

In addition, efficacy can be determined by one or more of following criteria:
  Number and percent of subjects with BILAG-2004 improvement: all A scores at baseline improved to B/C/D and all B scores at baseline improved to C/D at Week 4, 8, 12, 16, 20, 24, 28, 32, 36, 40, 44 and 48;
  Number and percent of subjects with enhanced BILAG-2004 improvement: all A/B scores at baseline improved to C/D (with no new A score and <=1 new B score) at Week 4, 8, 12, 16, 20, 24, 32, 36, 40, 44 and 48) and the improvement in individual organ systems of the BILAG-2004 at Week 4, 8, 12, 16, 20, 24, 32, 36, 40, 44 and 48;

Change from baseline in Physician Global Assessment at Week 2, 4, 8, 12, 16, 20, 24, 32, 36, 40, 44 and 48;

Change from baseline in proteinuria/urine sediment/serum creatinine/eGFR at W12, 24, 36 and W48;

Proportion of treatment failures (defined as non-protocol allowed increase in steroid dose, start IV or IM steroids, start or increase of immunosuppressant) at W24 and W48;

Reduction in flare rate at W24 and at W48. Severe flare defined as one new A score in any system of the BILAG 2004 index; moderate flare as 2 new B scores;

Proportion of patients able to decrease the daily dose of oral corticosteroids at W48 by 25% compared to baseline without a worsening of SLEDAI-2K;

Change from baseline in mean oral corticosteroid dose at W24 and W48;

Changes from baseline in the physical and mental component scores of SF-36 at week 24 and at week 48.

Other disease scores include European Consensus Lupus Activity Measurements (ECLAM) (Vitali et al. 1992, Clin. Exp. Rheumatol. 10: 541-7), System Lupus International Collaborating Clinics/ACR Damage Index for Systemic Lupus Erythematosus (SLICC), and Systemic Lupus Erythematosus Disease Activity Index (SLEDAI) (American College of Rheumatology).

Additional Therapeutic Agents

The polypeptides of the invention may be administered as a monotherapy or in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

As such, the present invention also provides methods and dosing schedules for subcutaneous administration of polypeptides that bind and block IL-6R, wherein the polypeptide is administered in combination with at least one additional therapeutic agent.

Without being limiting, additional therapeutic agents can be selected from non-steroidal anti-inflammatory drugs (NSAIDs), Corticosteroids, Disease modifying antirheumatic drugs (DMARDs), and biological therapies.

NSAIDs may, for example, be selected from aspirin, selective cyclooxygenase 2 inhibitors, and analgesics.

Corticosteroids may include, for example, prednisone.

Disease modifying antirheumatic drugs (DMARDs) can, for example, be selected from oral or parenteral gold, sulfasalazine, azathioprine, cyclosporine A, mycophenolate mofetil, hydroxychloroquine, chloroquine, leflunomide, sodium aurothiomalate, penicillamine, methotrexate (MTX), and glucocorticoids.

Approved or investigational biological or targeted synthetic DMARDs for RA may, for example, be selected from tumor necrosis factor alpha-inhibitors, selective T-cell costimulation molecule (such as cytotoxic T-lymphocyte-associated protein 4), cluster of differentiation 20 (CD20) inhibitors, interleukin-1 (IL-1) inhibitors, IL-6 and interleukin-6 receptor (IL-6R) inhibitors, and Janus kinase [JAK]-inhibitors.

Accordingly, the present invention also relates to a method and a polypeptide of the invention, such as SEQ ID NO: 34, for treatment of an IL-6R related disease, wherein the polypeptide is administered subcutaneously at a dose of 75-300 mg every week to every month or at a dose equivalent to 75-300 mg every week to every month, such as 75 mg every week to every month or a dose equivalent to 75 mg every week to every month, such as 150 mg every weeks to every month or a dose equivalent to 150 mg every week to every month, such as 225 mg every weeks to every month or a dose equivalent to 225 mg every week to every month, or 300 mg every weeks to every month or a dose equivalent to 300 mg every week to every month, in combination with at least one additional therapeutic agent.

In one aspect, the polypeptide of the invention is administered according to the method of the invention in combination with MTX. In one aspect, the polypeptide of the invention is administered to a subject suffering RA, preferably active RA, according to the method of the invention in combination with MTX. In one aspect, the polypeptide of the invention is administered to a subject suffering SLE, preferably severe or moderate active SLE, according to the method of the invention in combination with MTX. MTX can be administered, for example, at a stable dose of 12.5 mg/week to 25 mg/week.

In one aspect, the polypeptide of the invention is administered according to the method of the invention in combination with a corticosteroid, for example prednisone. In one aspect, the polypeptide of the invention is administered to a subject suffering RA, preferably active RA, according to the method of the invention in combination with a corticosteroid, for example prednisone. In one aspect, the polypeptide of the invention is administered to a subject suffering SLE, preferably severe or moderate active SLE, according to the method of the invention in combination with a corticosteroid, for example prednisone. Prednisone can be administered, for example, at a stable dose of 15 mg/week.

In one aspect, the polypeptide of the invention is administered according to the method of the invention in combination with azathioprine. In one aspect, the polypeptide of the invention is administered to a subject suffering RA, preferably active RA, according to the method of the invention in combination with azathioprine. In one aspect, the polypeptide of the invention is administered to a subject suffering SLE, preferably severe or moderate active SLE, according to the method of the invention in combination with azathioprine. Azathioprine can be administered, for example, at a stable dose of 150 mg/day.

In one aspect, the polypeptide of the invention is administered according to the method of the invention in combination with mycophenolate mofetil. In one aspect, the polypeptide of the invention is administered to a subject suffering RA, preferably active RA, according to the method of the invention in combination with mycophenolate mofetil. In one aspect, the polypeptide of the invention is administered to a subject suffering SLE, preferably severe or moderate active SLE, according to the method of the invention in combination with mycophenolate mofetil. Mycophenolate mofetil can be administered, for example, at a stable dose of 1.5 g/day.

In one aspect, the polypeptide of the invention is administered according to the method of the invention in combination with cyclosporine. In one aspect, the polypeptide of the invention is administered to a subject suffering RA, preferably active RA, according to the method of the invention in combination with cyclosporine. In one aspect, the polypeptide of the invention is administered to a subject suffering SLE, preferably severe or moderate active SLE, according to the method of the invention in combination with cyclosporine. Cyclosporine can be administered, for example, at a stable dose of 20 mg/day.

In one aspect, the polypeptide of the invention is administered according to the method of the invention in combination with leflunomide. In one aspect, the polypeptide of the invention is administered to a subject suffering RA, preferably active RA, according to the method of the invention in combination with leflunomide. In one aspect, the polypeptide of the invention is administered to a subject suffering SLE, preferably severe or moderate active SLE, according to the method of the invention in combination with leflunomide. Leflunomide can be administered, for example, at a stable dose of 20 mg/day.

In one aspect, the polypeptide of the invention is administered according to the method of the invention in combination with hydroxychloroquine. In one aspect, the polypeptide of the invention is administered to a subject suffering RA, preferably active RA, according to the method of the invention in combination with hydroxychloroquine. In one aspect, the polypeptide of the invention is administered to a subject suffering SLE, preferably severe or moderate active SLE, according to the method of the invention in combination with hydroxychloroquine.

The Figures, and the Experimental Part/Examples are only given to further illustrate the invention and should not be interpreted or construed as limiting the scope of the invention and/or of the appended claims in any way, unless explicitly indicated otherwise herein.

EXAMPLES

Example 1: Evaluation of the Bioavailability of SEQ ID NO: 34 after Subcutaneous and Intravenous Administration in Healthy Volunteers In this study, the pharmacokinetics (PK), pharmacodynamics (PD) and safety of single subcutaneous (s.c.) and intravenous (i.v.) doses of SEQ ID NO: 34 was assessed in healthy volunteers.

70 human subjects were assigned to 1 of 5 treatment arms (with 14 subjects per treatment arm) and received one of the following single doses of SEQ ID NO: 34: 150 mg s.c., 300 mg s.c., 300 mg i.v., 50 mg s.c, or 50 mg i.v. Subjects in the i.v. groups of the study received a single dose of SEQ ID NO: 34 as i.v. infusion at a fixed infusion rate of 1.5 mL/min. Subjects in the s.c. parts of the study received a single dose of SEQ ID NO: 34 via s.c. injection in the abdominal region. For the 50 and 150 mg treatment arms, 1 injection (of 333 μL and 1 mL [of a 150 mg/ml SEQ ID NO: 34 composition], respectively) was performed in an abdominal quadrant of choice. For the 300 mg s.c. treatment arm, 2 injections (of 1 mL each [of a 150 mg/ml SEQ ID NO: 34 composition]) were required and these needed to be performed in 2 different locations.

After study drug administration, subjects were monitored for approximately 2 months for subjects in the 50 mg and 150 mg treatment arms and approximately 3 months for subjects in the 300 mg treatment arms, to allow adequate follow-up of PD. A total of 67 subjects completed the study.

Pharmacokinetics

Blood samples were taken for analysis of SEQ ID NO: 34 concentrations in serum at 12 hours, 24 hours, 48 hours, 3 days, 4 days, 6 days, 8 days, 11 days, 18 days, 25 days, 32 days, 39 days (150 mg and 300 mg treatment arms only), 46 days (150 mg and 300 mg treatment arms only), and 53 days (300 mg treatment arm only) after dosing.

The determination of total active SEQ ID NO: 34 concentrations in human serum samples was performed using a validated enzyme-linked immunosorbent assay (ELISA). In short, an anti-SEQ ID NO: 34 Nanobody was used to capture SEQ ID NO: 34. To determine total active SEQ ID NO: 34 concentrations, a complexation of the serum samples with human sIL-6R was performed. The complexes were detected with a mouse anti-human IL-6R antibody, followed by rabbit anti-mouse immunoglobulin G-horseradish peroxidase allowing detection via spectrophotometry.

Figure 1B:
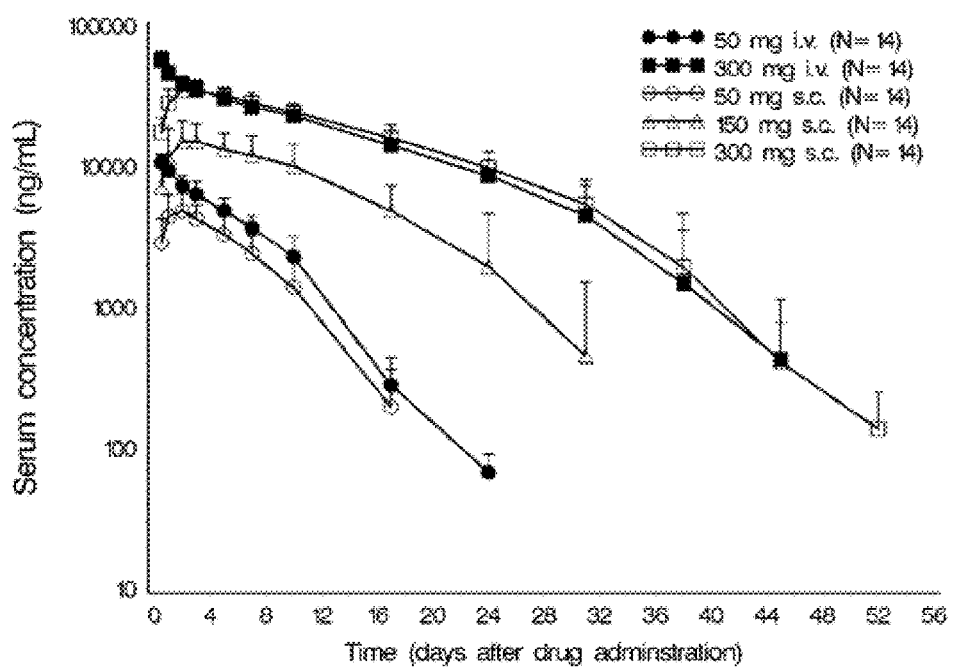

Mean serum concentrations of SEQ ID NO: 34 increased with increasing dose following single dose administration of SEQ ID NO: 34 as i.v. infusion (50 mg and 300 mg) or s.c. injection (50 mg, 150 mg and 300 mg) (FIG. 1). Following i.v. administration, mean serum concentration-time profiles of SEQ ID NO: 34 displayed a biphasic decline characterized by a dose-dependent disposition phase followed by a faster terminal elimination phase. After s.c. administration, mean SEQ ID NO: 34 serum concentrations increased with a peak already occurring at approximately 48 h post-dose and gradually declined thereafter.

The Pharmacokinetics (PK) of SEQ ID NO: 34 have been mainly characterized through population PK analysis of data pooled from the study described in WO 2013/041722 conducted in RA patients and healthy volunteers. Supportive Standard Non Compartmental PK Analysis (PK NCA) has been performed in clinical pharmacology studies, providing further insight on the understanding of the pharmacokinetic behaviour of SEQ ID NO: 34.

The PK of SEQ ID NO: 34 was characterized by non-linear kinetics over the tested dose-range (0.3-6 mg/kg iv doses, 50-300 mg s.c. doses) explained by concentration-dependent clearance (CL). Overall, after multiple dose the accumulation was limited, and PK parameters did not change over-time. After subcutaneous administration, PK NCA results indicated an apparent dose-dependent bioavailability, higher and almost complete at the highest tested dose.

The observed concentration-dependency of SEQ ID NO: 34 CL could be described by a population PK model. An empirical bi-compartmental disposition model with parallel linear (first-order) and non-linear saturable clearance characterized well the observed exposure after single and multiple intravenous administration. The volume of distribution was limited, indicating that SEQ ID NO: 34 was restricted to the systemic circulation, and rather constant across dose-levels. The non-linear component of the clearance, likely reflecting an elimination occurring after the drug binds to its IL-6R target, was saturated at relatively low serum concentrations, indicating that at higher levels of exposure the total CL is mainly determined by linear processes.

The addition of a subcutaneous absorption compartment to the population PK model indicated a rapid first-order absorption process of approximately 1 to 3 days. Mean $t_{max}$ ranged from 1.9 days (50 mg s.c. dose), 2.7 days (150 mg s.c. dose) to 3.23 days (300 mg s.c. dose). Dose-dependency of the subcutaneous bioavailability could not be concluded. Bioavailability was estimated at 82.3% based on a combination of the i.v. data available from the study described in WO 2013/041722 and the present study.

As SEQ ID NO: 34 PK was dose-dependent due to a different contribution of the non-linear clearance at different serum concentrations, also the terminal half-life (t½) was dose-dependent. At high concentrations, when non-linear clearance became negligible, the apparent t½ estimated from the only linear CL term, was estimated at approximately 15 days, based on data available from the study described in WO 2013/041722 and the present study.

Pharmacodynamics

The pharmacodynamics of single subcutaneous (s.c.) and intravenous (i.v.) doses of SEQ ID NO: 34 was assessed by measurement of the plasma total soluble interleukin-6 receptor (sIL-6R) concentration and the serum interleukin-6 (IL-6) concentration. Blood samples were taken for analysis of IL-6 and sIL-6R at 24 hours, 6 days, 11 days, 18 days, 25 days, 32 days, 39 days (150 mg and 300 mg treatment arms only), 46 days (150 mg and 300 mg treatment arms only), and 53 days (300 mg treatment arm only) after dosing.

IL-6

For determining IL-6 concentrations in human serum, the commercially available "Human IL-6 QUANTIGLO® ELISA Kit" from R&D Systems was used (cat #Q6000B). The assay was performed as described in the manufacturer's instructions.

Following administration of a single dose of SEQ ID NO: 34, mean IL-6 serum concentrations increased from 24 h post-dose. For both the i.v. and s.c. administration routes an initial rapid increase in mean IL-6 serum concentrations was seen. There was no clear dose response with respect to the maximal serum IL-6 concentrations.

In the 50 mg s.c. group a peak concentration was observed on Day 2 due to a markedly high IL-6 concentration (366.88 pg/mL) observed in one subject (50 mg s.c. dose group). This subject reported a sore throat (preferred term: oropharyngeal pain) on Day 2 and a tendency towards an increase in neutrophil count.

Figure 2:
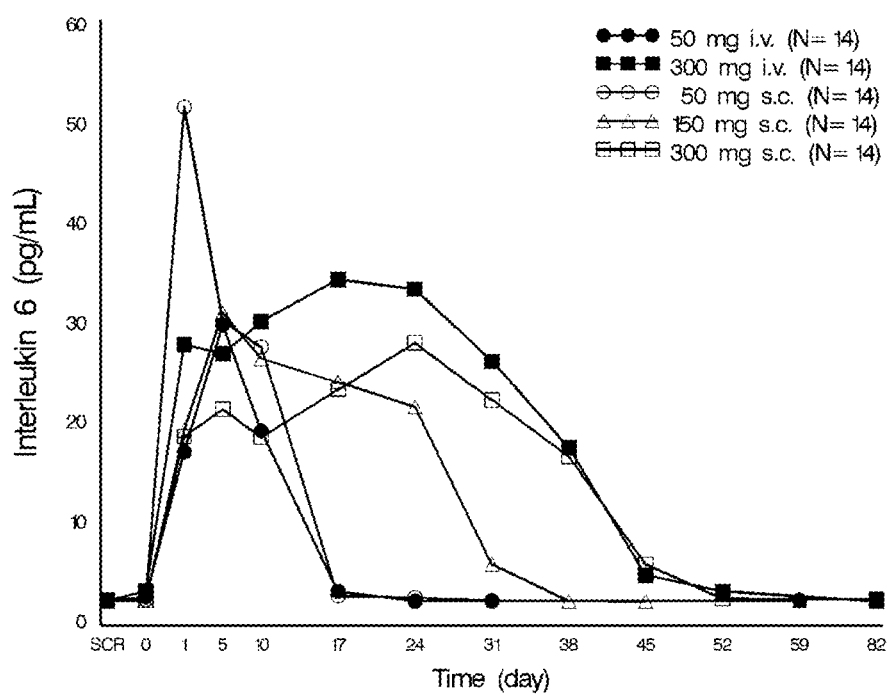
FIG. 2 is a graph depicting IL-6 serum concentrations after s.c. and i.v. administration of SEQ ID NO: 34 in healthy human subjects.

The duration of effect was dose-related and thus longer in the higher dose groups. Mean IL-6 levels returned to baseline values at Day 25, Day 39 and Day 53 for the 50, 150 and 300 mg dose groups, respectively (FIG. 2).

Total sIL-6R

The analysis of total sIL-6R in plasma was performed using a validated ELISA method. In short, a non-neutralizing anti-IL-6R monoclonal antibody was first coated on a 96 well MAXISORP® plate by adsorption, after which excess binding sites were blocked with PBS-1% casein. Calibrators and validation samples were prepared from stock solutions of recombinant human sIL-6R using cynomolgus monkey sIL-6R free plasma and diluent (PBS/0.1% casein/0.05% Tween20 supplemented with 100 ng/mL SEQ ID NO: 34 to overcome drug interference). After transfer of the calibrators and samples onto the plate, detection was performed with a biotinylated goat anti-human IL-6R antibody and horseradish peroxidase (HRP)-labeled streptavidin. In the presence of $H_2O_2$, the peroxidase catalyzes a chemical reaction with the enhanced soluble 3,3',5,5'-tetramethylbenzidine (es-TMB) resulting in a colorimetric change. After stopping the colorimetric reaction with 1M HCl, the optical density was measured at a wavelength of 450 nm in a plate spectrophotometer.

Figure 3:
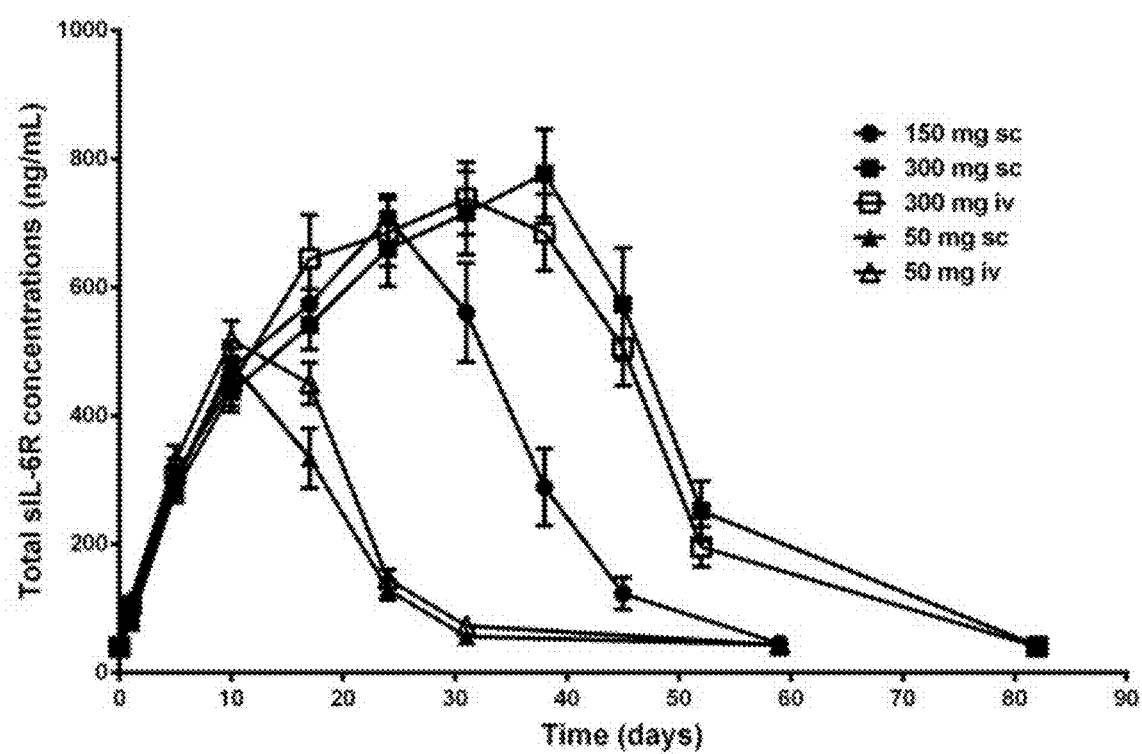
FIG. 3 is a graph depicting sIL-6R plasma concentrations after s.c. and i.v. administration of SEQ ID NO: 34 in healthy human subjects.

Baseline sIL-6R plasma concentrations were comparable for all treatment groups with mean baseline concentrations ranging between 38.4 ng/mL and 42.6 ng/mL. Following administration of a single dose of SEQ ID NO: 34, mean sIL-6R concentrations increased rapidly. A dose-related effect was observed on the magnitude and the duration of the increased sIL-6R concentrations. At each dose level, mean sIL-6R levels had returned to baseline values at follow-up (i.e., Day 60 for the 50 mg and 150 mg dose groups and Day 83 for the 300 mg dose groups) (FIG. 3).

Safety

Overall, treatment with a single i.v. or s.c. dose of SEQ ID NO: 34 up to a dose level of 300 mg appeared to be safe and well tolerated in healthy subjects. There were no clinically significant findings with respect to clinical laboratory, vital signs, ECGs, physical examination or body weight. A tendency towards a mild decrease in hsCRP, fibrinogen and neutrophil count was observed.

To assess immunogenicity, the presence of ADA was measured in serum. Pre-existing antibodies and treatment emergent (TE) ADA were detected in 11% and 10% of the subjects, respectively. Nine % (6/70) were classified as equivocal since in those subjects no TE ADA response was detected but pre-existing antibodies were present at levels possibly defying TE ADA. No apparent influence of pre-existing antibodies or TE ADA was seen on PK and PD by visual inspection of the PK and total sIL-6R curves.

Example 2: Dose Calculation for Treatment of RA Patients

The PK and PD results obtained in Example 1 were used to bridge from i.v. to s.c. administration, and to determine the appropriate doses for a study in subjects suffering RA and for a study in subjects suffering SLE.

A PK-PD model, developed based on data pooled from the i.v. study described in WO 2013/041722 and the study described in Example 1, was used to predict the response (in terms of DAS28) at different dose levels/regimens. Dose levels and regimens were selected based on profiles spread between the estimated DAS28 half maximal effective concentration ($EC_{50}$). As a result of this evaluation, the s.c. administration of 75 mg, 150 mg, 225 mg and 300 mg SEQ ID NO: 34 administered q2w or q4w appears to be appropriate for ensuring an adequate assessment of the dose-response and exposure-response relationships, while keeping adequate safety margins when considering the exposure levels attained in a preclinical toxicity program.

Simulations of the PK model were based on the expected body weight distribution of RA patients. RA patients were sampled from a distribution with mean body weight of 78 kg, with a standard deviation of 19 kg and a minimum and maximum body weight of 40 kg and 150 kg, respectively. Typical individual PK simulations (RA patient with body weight of 78 kg, n=1000) of the PK model were performed for a wide dose range between 0 and 600 mg s.c. q2w and q4w, at steady state. From these simulations, the predicted $C_{min}$ at steady state ($C_{min,ss}$) was derived and compared with the DAS28 $EC_{50}$ (SEQ ID NO: 34 concentration resulting in half-maximal effect of SEQ ID NO: 34 on the DAS28 efficacy measure) estimated by the PK-DAS28 model. Based on this analysis, the doses 75 and 150 mg q4w and 150 and 225 mg q2w of SEQ ID NO: 34 were selected as adequate doses to assess the exposure-response relationship of SEQ ID NO: 34 in RA patients. Through simulations, it was shown that these doses are covered by adequate safety margins, when comparing the model predicted human exposure with the observed exposure in the toxicity studies.

Figure 4:
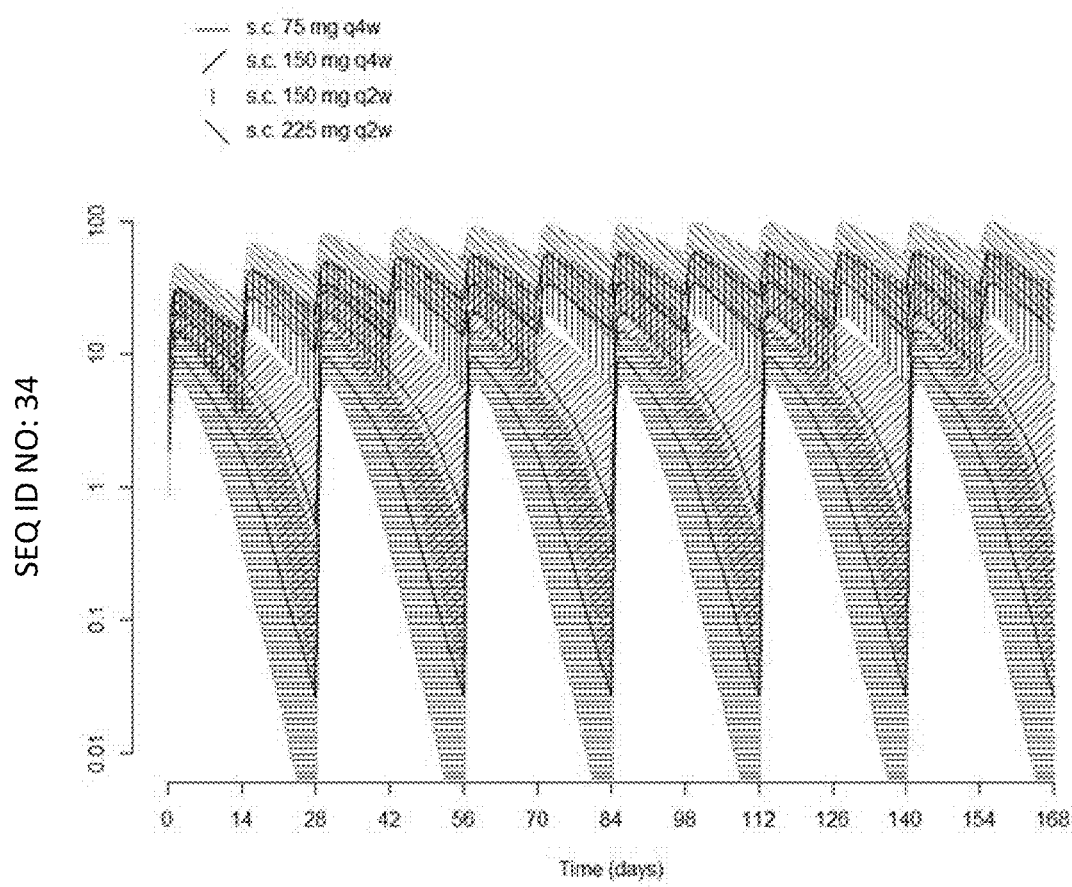
FIG. 4 is a graph depicting model-predicted PK profiles of SEQ ID NO: 34 following s.c. administration of SEQ ID NO: 34 at a dose of 75 and 150 mg q4w and 150 and 225 mg q2w. The PK profiles were simulated by sampling a thousand RA patients from the expected body weight distribution as specified in Example 2.

FIG. 4 shows the model-predicted PK profiles of SEQ ID NO: 34 simulated by sampling a thousand RA patients from the expected body weight distribution as specified above following s.c. administration of SEQ ID NO: 34 at a dose of 75 and 150 mg q4w and 150 and 225 mg q2w.

Figure 5:
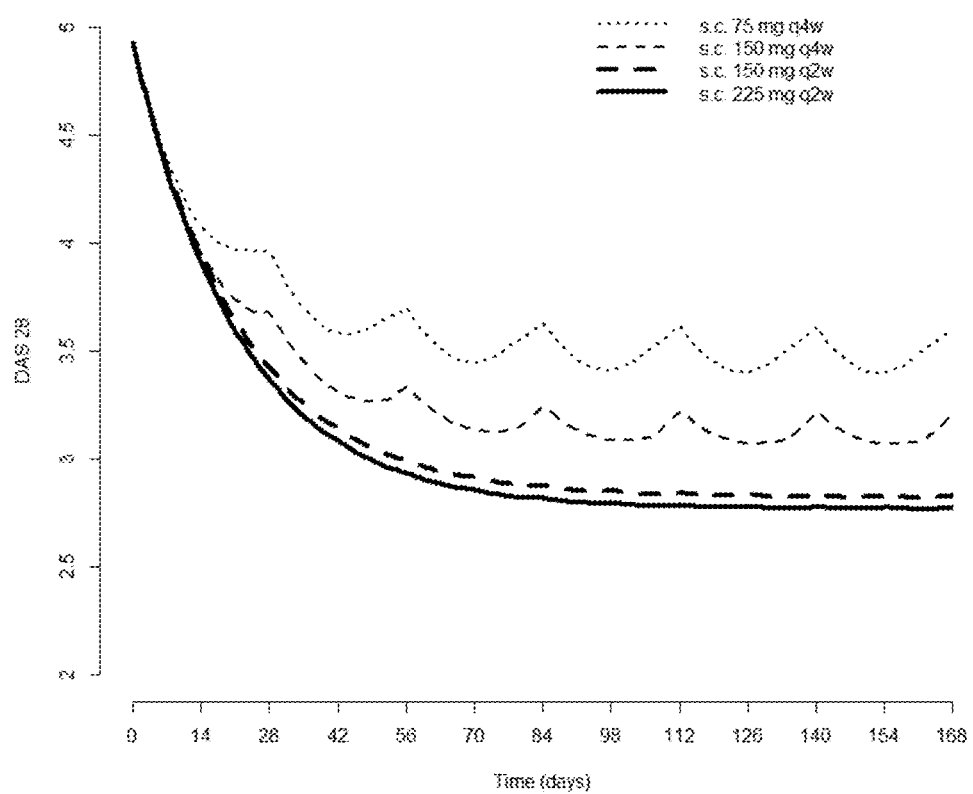
FIG. 5 is a graph depicting model-predicted median DAS28 response following s.c. administration of SEQ ID NO: 34 at a dose of 75 and 150 mg q4w and 150 and 225 mg q2w (DAS28 baseline value of 4.93). The median DAS28 response was based on simulations performed using the same 1000 RA patients as for the simulated PK profiles.

FIG. 5 shows the model-predicted median DAS28 response based on simulations performed using the same 1000 RA patients as for the simulated PK profiles following s.c. administration of SEQ ID NO: 34 at a dose of 75 and 150 mg q4w and 150 and 225 mg q2w (DAS28 baseline value of 4.93).

Example 3: Subcutaneous Administration of SEQ ID NO: 34 to RA Patients

In this study the efficacy and safety is assessed of dose regimens of SEQ ID NO: 34 administered subcutaneously (s.c.) in combination with methotrexate (MTX) to subjects with active rheumatoid arthritis despite MTX therapy. Additionally, the effects of dose regimens of SEQ ID NO: 34 on quality of life, pharmacokinetics (PK), pharmacodynamics (PD), and immunogenicity of SEQ ID NO: 34 is assessed.

Study Design

A multicenter, randomized, double-blind, placebo-controlled study of SEQ ID NO: 34 administered s.c. in combination with MTX is conducted in subjects with active RA despite MTX therapy. Up to approximately 330 subjects are randomized in 5 treatment arms in a 1:1:1:1:1 ratio as follows: placebo, 75 mg of SEQ ID NO: 34 every 4 weeks (q4w) (0.5 mL of a 150 mg/ml SEQ ID NO: 34 composition), 150 mg of SEQ ID NO: 34 q4w (1 mL of a 150 mg/ml SEQ ID NO: 34 composition), 150 mg of SEQ ID NO: 34 q2w (1 mL of a 150 mg/ml SEQ ID NO: 34 composition), 225 mg of SEQ ID NO: 34 q2w (1.5 mL of a 150 mg/ml SEQ ID NO: 34 composition). SEQ ID NO: 34 is administered subcutaneously using a single-use pre-filled syringe comprising a pharmaceutical composition with SEQ ID NO: 34 at a concentration of 150 mg/ml. Subjects receive SEQ ID NO: 34 and/or placebo on top of their stable dose of MTX (12.5-25 mg weekly).

Subjects receive treatment from Week 0 up to and including Week 22. Subjects return for 13 ambulatory visits planned at Weeks 0, 2, 4, 6, 8, 10, 12, 14, 16, 18, 20, 22 and 24.

Any subject with less than 20% improvement from baseline in both swollen and tender joint count (SJC and TJC; 66/68 counts) at any of the visits at week 12, 16 or 20 discontinueS from the trial. The visit at which subjects meet the efficacy discontinuation criteria, is defined as the Early Termination Visit for these patients.

Subjects who discontinue early for reasons other than the efficacy discontinuation criteria have an Early Termination Visit at 2 weeks after the last study drug administration unless they discontinue during a study visit in which case that becomes their Early Termination Visit. Subjects should also return for a Follow-up Visit 12 weeks after last study drug administration.

Efficacy

The reduction of signs and symptoms of RA is evaluated by calculating the proportion of subjects achieving an ACR20 response at week 12. In addition, higher levels of response, as measured by ACR50 and ACR70 response rates, and measures of remission using the DAS28, Clinical Disease Activity Index (CDAI), Simplified Disease Activity Index (SDAI), as well as the Boolean remission definition, are used as supportive evidence of efficacy. In addition, endpoints, including ACR responses and disease activity scores, are documented over time, including earlier time points, before the therapeutic plateau is expected. This allows evaluation of potential differences in early clinical efficacy between the doses. Other RA domains, such as improvement in physical function and health-related quality of life, are evaluated using the HAQ-DI, FACIT-Fatigue scale and the SF-36 questionnaires.

Physician's Assessment of Tender and Swollen Joint Count

All joints listed are used in the determination of the ACR response, where 68 joints are assessed for tenderness and 66 joints are assessed for swelling.

If tenderness or swelling is noted, a "1" is entered for that joint in the appropriate field. If tenderness or swelling is absent, a "0" is entered for that joint in the appropriate field.

Duration of Morning Stiffness

The average duration of morning stiffness during the previous week in minutes is assessed. If a subject has stiffness that lasts the entire day, this is recorded as 1440 minutes of morning stiffness.

Patient's Assessment of Pain (100 mm-VAS)

Patient's assessment of pain (100 mm-VAS) is performed as part of ACR response and prior to the joint count assessments. The subject is asked, "How much pain have you had because of your condition over the past week?" and then instructed to place a mark between 0 ("no pain") and 100 mm ("pain as bad it could be") on the VAS scale to indicate how severe the pain has been.

Patient's Global Assessment of Disease Activity (100 mmm-VASPA)

Patient's Global Assessment of Disease Activity (100 mmm-VASPA) is performed as part of ACR response, DAS28 score, SDAI, CDAI, and Boolean remission. The subject must complete the patient's global assessment independently of the physician when completing the physician global assessment.

The subject is instructed as follows: "Considering all the ways in which illness and health conditions may affect you at this time, please make a mark between 0 ("very well") and 100 mm ("very bad") on the VAS scale to show how you are doing."

Physician's Global Assessment of Disease Activity (100 mm-VASPHA)

Physician's Global Assessment of Disease Activity (100 mm-VASPHA) is performed as part of ACR response, SDAI, and CDAI. The physician must complete the physician's global assessment independently of the subject when completing the patient's global assessment. The physician makes a mark between 0 ("very good") and 100 mm ("very bad") on the VAS scale to indicate disease activity (independent of the subject's self-assessment).

C-Reactive Protein

C-reactive protein (CRP) is measured as part of ACR response, DAS28 score, SDAI, Boolean remission and EULAR Response.

For determining CRP concentrations in human serum, any method available in the art can be used such as e.g. the commercially available "IMMAGE® Immunochemistry Systems C-Reactive Protein (Kit Recorder #447280)" from Beckman Coulter Inc. (Brea, Calif., US). CRP concentration is to be provided in mg/L.

Erythrocyte Sedimentation Rate

Erythrocyte Sedimentation Rate (ESR) is measured as part of the DAS28 score and EULAR Response.

For determining ESR levels in serum, any method available in the art can be used such as e.g. the commercially available Greiner ESR tube or the Preanalytics—VACUETTE® Evacuated Collection Tubes (Greiner Bio-One GmbH, Kremsmuenster, Austria), the Sarstedt SEDIPLUS® 2000 (Sarstedt, Nümbrecht, Germany), or the Becton Dickinson SEDITAINER® (Becton Dickinson, Franklin Lakes, N.J., USA). The ESR concentration is to be provided in mm/h.

Health Assessment Questionnaire Disability Index

Health Assessment Questionnaire Disability Index (HAQ-DI) is performed as part of ACR response and on its own.

The HAQ-DI is a 20-question instrument which assesses the degree of difficulty the subject had in accomplishing tasks in 8 functional areas (dressing and grooming, arising, eating, walking, hygiene, reaching, gripping, and errands and chores) over the previous week. Within each category, subjects report the amount of difficulty they have in performing the specific sub-category items. There are four response options ranging from: 0=No Difficulty; 1=With Some Difficulty; 2=With Much Difficulty; 3=Unable to Do.

SF-36

The SF-36 consists of 36 items that can be summarized into 8 domains: physical functioning, role limitations due to physical health problems (role-physical), bodily pain, general health, vitality, social functioning, role limitations due to emotional problems (role-emotional), and mental health. Two summary measures, the physical component summary and the mental component summary, can be derived based on these domain scores.

The concepts measured by the SF-36 are not specific to any disease, allowing comparison of relative burden of different diseases, in addition to the relative benefit of different treatments.

FACIT-Fatigue

The FACIT Measurement System is a collection of health-related quality of life questionnaires that assess multidimensional health status in people with various chronic illnesses, including RA.

ACR20, ACR50, ACR70 Responses

ACR responses are measured according to the 2010 European League Against Rheumatism [EULAR]/American College of Rheumatology [ACR] classification criteria. ACR20/50/70 responses are defined as below:

≥20/50/70% improvement in tender/painful joint count (TJC) (68 joints) relative to baseline AND ≥20/50/70% improvement in swollen joint count (SJC) (66 joints) relative to baseline AND ≥20/50/70% improvement in 3 of the following 5 areas relative to baseline:

Patient's Assessment of Pain (100 mm-VAS).

Patient's Global Assessment of Disease Activity (100 mm-VASPA).

Physician's Global Assessment of Disease Activity (100 mm-VASPHA).

Patient's Asessment of physical function as measured by the Health Assessment Questionnaire Disability Index (HAQ-DI).

C-reactive protein (CRP).

ACR-N Index of Improvement

The ACR-N Index of Improvement is defined as the minimum of the following 3 criteria:

The percent improvement from baseline in tender joint counts (TJCs).

The percent improvement from baseline in swollen joint (SJCs).

The median percent improvement from baseline for the following 5 assessments:

Patient's Assessment of Pain (VAS).

Patient's Global Assessment of Disease Activity (VASPA).

Physician's Global Assessment of Disease Activity (VASPHA).

Patient's Assessment of physical function as measured by the HAQ-DI.

CRP.

DAS28

The DAS28 based on erythrocyte sedimentation rate (ESR) is a statistically derived index combining TJC (28 joints), SJC (28 joints), ESR, and VASPA (Briso et al. 2008, J. Immunol., 180: 7102-7106). CRP can be used in addition to ESR in the calculation of DAS28. CRP is a more direct measure of inflammation than ESR, and it is more sensitive to short-term changes. CRP is considered at least as valid as ESR to measure RA disease activity. As such, the DAS28 using CRP is a statistically derived index combining TJC (28 joints), SJC (28 joints), CRP, and VASPA.

Cut-off points for DAS28 (ESR) to define if a subject is in clinical remission or in a state of high, moderate, or low disease activity have been defined (Betz and W. Muller 1998, Int. Immunol. 10: 1175-1184):

| High disease activity | DAS28 > 5.1 |
| Moderate disease activity | 3.2 < DAS28 ≤ 5.1 |
| Low disease activity | 2.6 ≤ DAS28 ≤ 3.2 |
| Remission | DAS28 < 2.6 |

EULAR response is assessed by comparing a subject's DAS28 score (using CRP and ESR) relative to baseline as follows.

| | Improvement in DAS28 Relative to Baseline | | |
| --- | --- | --- | --- |
| Present DAS28 | >1.2 | >0.6 and ≤1.2 | ≤0.6 |
| ≤3.2 | good response | moderate response | no response |
| >3.2 and ≤5.1 | moderate response | moderate response | no response |
| >5.1 | moderate response | no response | no response |

Disease Activity

For measurement of the disease activity, the Disease Activity Score is determined using 28 joint counts (DAS28 using CRP and erythrocyte sedimentation rate (ESR)). In addition, the Simplified Disease Activity Index (SDAI) and Clinical Disease Activity Index (CDAI) is determined.

The CDAI clinical score is determined according to following criteria (Felson, et al. 2011; Aletaha and Smolen 2007, Clinical rheumatology 21: 663-75):

Calculation of CDAI Score: CDAI=TJC28+SJC28+VASPA+VASPHA

Classification of CDAI Score:

| CDAI Score | CDAI ≤ 2.8 | 2.8 < CDAI ≤ 10 | 10 < CDAI ≤ 22 | 22 < CDAI |
|---|---|---|---|---|
| Disease Activity | remission | low disease activity | moderate disease activity | high disease activity |

The SDAI clinical score is determined according to following criteria (Aletaha and Smolen 2007):
   Calculation of SDAI Score: SDAI=TJC28+SJC28+VASPA+VASPHA+CRP
   Classification of SDAI Score:

| SDAI Score | SDAI ≤ 3.3 | 3.3 < SDAI ≤ 11.0 | 11.1 < SDAI ≤ 26.0 | SDAI > 26.0 |
|---|---|---|---|---|
| Disease Activity | remission | low disease activity | moderate disease activity | high disease activity |

Remission

Remission is determined using disease remission parameters: DAS28, Simplified Disease Activity Index (SDAI), Clinical Disease Activity Index (CDAI), Boolean.

Boolean remission is determined according to following criteria (Felson et al. 2011, American College of Rheumatology/European League against Rheumatism provisional definition of remission in rheumatoid arthritis for clinical trials. Annals of the rheumatic diseases 70: 404-13):
   If TJC28≤1 and SJC28≤1 and VASPA (cm)≤1 and CRP (mg/dL)≤1
     Then remission="yes"
     Else remission="no"

Pharmacokinetics

Blood samples are taken for analysis of SEQ ID NO: 34 in serum at 2, 4, 6, 8, 10, 12, 16, 20, and 24 weeks after dosing. The determination of total active SEQ ID NO: 34 concentrations in human serum samples is performed using a validated enzyme-linked immunosorbent assay (ELISA) similar as described in Example 1.

Pharmacodynamics

The pharmacodynamics of SEQ ID NO: 34 is assessed by measurement of the total soluble interleukin-6 receptor (sIL-6R) in blood samples.

For determining plasma sIL-6R concentrations, blood samples are taken at 2, 4, 6, 10, 12, and 24 weeks after dosing. The analysis of total sIL-6R in plasma is performed using a validated ELISA method as described in Example 1.

Safety

Safety and tolerability assessments includes evaluation of (serious) AEs and injection site reactions, laboratory assessment, urinalysis, vital signs, and physical examination.

To assess immunogenicity, the presence of ADA is measured in serum until the follow-up visit.

Example 4: Subcutaneous Administration of SEQ ID NO: 34 to SLE Patients

In this study the efficacy and safety is assessed of dose regimens of SEQ ID NO: 34 administered subcutaneously (s.c.) to subjects with Systemic Lupus Erythematosus (SLE). Additionally, the effects of dose regimens of SEQ ID NO: 34 on quality of life, pharmacokinetics (PK), pharmacodynamics (PD), immunogenicity of SEQ ID NO: 34, flare rate, and steroid reduction is assessed.

Study Design

A multicenter, randomized, double-blind study of SEQ ID NO: 34 administered s.c. (on top of standard care) is conducted in subjects with moderate to severe active SLE. Up to approximately 300 subjects are randomized in 5 treatment arms in a 1:1:1:1:1 ratio as follows: placebo, 75 mg of SEQ ID NO: 34 every 4 weeks (q4w) (0.5 mL of a 150 mg/ml SEQ ID NO: 34 composition), 150 mg of SEQ ID NO: 34 q4w (1 mL of a 150 mg/ml SEQ ID NO: 34 composition), 150 mg of SEQ ID NO: 34 q2w (1 mL of a 150 mg/ml SEQ ID NO: 34 composition), 225 mg of SEQ ID NO: 34 q2w (1.5 mL of a 150 mg/ml SEQ ID NO: 34 composition). SEQ ID NO: 34 is administered subcutaneously using a single-use pre-filled syringe comprising a pharmaceutical composition with SEQ ID NO: 34 at a concentration of 150 mg/ml.

Subjects receive treatment at week 0 and up to week 46. Subjects come to the site every 2 weeks for study drug administration up to Week 24. After Week 24, patients return to the site on a monthly basis and patients self-administer at home at weeks 26, 30, 34, 38, 42 and 46. In all treatment arms, subjects receive their last dose at week 46.

Efficacy

Efficacy is determined by the percentage of patients who achieved a response at Week 24 according to the (modified) SLE Responder Index ((m)SRI). (m)SRI responder is defined as:
   Reduction from baseline in (modified) SLEDAI-2K (mSLEDAI-2K) of ≥4 points;
   No new A score and no more than one new B score on the BILAG-2004 compared with baseline;
   No increase in the Physician Global Assessment score of 0.3 point on a Visual Analogue Scale (VAS) of 0-3;

The modified as well as the standard index is analyzed as individual criteria and as components of the composite endpoint. A modified SLEDAI-2K index is derived from the standard index by omitting 1 of the standard items (low complement). An anti-IL-6 compound strongly decreases production of acute phase reactants, including complement (Illei 2010, Arthritis Rheum. 62: 542-52; Szepietowski 2013 Arthritis Rheum. 65: 2661-71). Therefore, the C¾ values (parameters of the low complement item in the SLEDAI-2K index) may be decreased due to decreased production while effect on complement consumption (relevant for disease activity evaluation) cannot be assessed.

Efficacy is further determined by composite endpoint mSRI as well as standard SRI (using the standard SLEDAI-2K including the low complement item) over time (weeks 2, 4, 8, 12, 16, 20, 24, 28, 32, 36, 40, 44 and 48).

Efficacy is also determined by the change from baseline in mSLEDAI-2K total score as well as standard SLEDAI-2K measured over time (weeks 2, 4 and every 4 weeks up to week 48).

In addition, efficacy is determined by following criteria:
   Number and percent of subjects with BILAG-2004 improvement: all A scores at baseline improved to B/C/D and all B scores at baseline improved to C/D at Week 4, 8, 12, 16, 20, 24, 28, 32, 36, 40, 44 and 48;
   Number and percent of subjects with enhanced BILAG-2004 improvement: all A/B scores at baseline improved to C/D (with no new A score and <=1 new B score) at Week 4, 8, 12, 16, 20, 24, 32, 36, 40, 44 and 48) and the improvement in individual organ systems of the BILAG-2004 at Week 4, 8, 12, 16, 20, 24, 32, 36, 40, 44 and 48;
   Change from baseline in Physician Global Assessment at Week 2, 4, 8, 12, 16, 20, 24, 32, 36, 40, 44 and 48;

Change from baseline in proteinuria/urine sediment/serum creatinine/eGFR at W12, 24, 36 and W48;

Proportion of treatment failures (defined as non-protocol allowed increase in steroid dose, start IV or IM steroids, start or increase of immunosuppressant) at W24 and W48;

Reduction in flare rate at W24 and at W48. Severe flare defined as one new A score in any system of the BILAG 2004 index; moderate flare as 2 new B scores;

Proportion of patients able to decrease the daily dose of oral corticosteroids at W48 by 25% compared to baseline without a worsening of SLEDAI-2K;

Change from baseline in mean oral corticosteroid dose at W24 and W48;

Changes from baseline in the physical and mental component scores of SF-36 at week 24 and at week 48.

Pharmacokinetics

Blood samples are taken for analysis of SEQ ID NO: 34 in serum every 2 weeks starting at Week 0 up to Week 12 and monthly thereafter up to Week 48 or early termination visit. The determination of total active SEQ ID NO: 34 concentrations in human serum samples is performed using a validated enzyme-linked immunosorbent assay (ELISA) similar as described in Example 1.

Pharmacodynamics

Samples for determination of biomarker levels, including but not limited to total sIL-6R, IL-6, CRP, fibrinogen, anti-dsDNA, C3, C4, CH50 are taken at the following times (at the time points when a dose is to be administered, samples are taken pre-dose): every 2 weeks from screening up to Week 12 and every 4 weeks thereafter up to Week 48 or early termination, and follow-up visit.

Safety

Safety and tolerability assessments include evaluation of (serious) AEs and injection site reactions, laboratory assessment, urinalysis, ECG, vital signs, and physical examination.

To assess immunogenicity, the presence of ADA is measured in serum until the follow-up visit.

Example 5: Subcutaneous Administration of SEQ ID NO: 34 to RA Patients (Monotherapy)

In this study the efficacy and safety is assessed of dose regimens of SEQ ID NO: 34 administered subcutaneously (s.c.) as monotherapy to subjects with active rheumatoid arthritis who are intolerant to MTX therapy. Additionally, the effects of dose regimens of SEQ ID NO: 34 on quality of life, pharmacokinetics (PK), pharmacodynamics (PD), and immunogenicity of SEQ ID NO: 34 is assessed.

Study Design

A multicenter study of SEQ ID NO: 34 administered s.c. as monotherapy is conducted in subjects with active RA who are intolerant to MTX, or whom continued MTX treatment is inappropriate. Up to approximately 228 subjects are randomized in 4 treatment arms in a 1:1:1:1 ratio as follows: 150 mg of SEQ ID NO: 34 q4w (1 mL of a 150 mg/ml SEQ ID NO: 34 composition), 150 mg of SEQ ID NO: 34 q2w (1 mL of a 150 mg/ml SEQ ID NO: 34 composition), 225 mg of SEQ ID NO: 34 q2w (1.5 mL of a 150 mg/ml SEQ ID NO: 34 composition), and 162 mg of tocilizumab (TCZ) (Ro-Actemra, Roche—Actemra, Genentech, Inc.) q1w or q2w (US-subjects only). SEQ ID NO: 34 is administered subcutaneously using a single-use pre-filled syringe comprising a pharmaceutical composition with SEQ ID NO: 34 at a concentration of 150 mg/ml. Note that since there is a difference in approved dosing frequency in the US (q2w) versus the EU (q1w), 2 different dosing regimens for TCZ are included in the study. Subjects receive the dosing regimen approved in their region.

Subjects receive treatment from Week 0 up to and including Week 10 for subjects assigned to the SEQ ID NO: 34 and q2w TCZ treatment groups, or up to and including Week 11 for subjects receiving TCZ q1w. Subjects assigned to the SEQ ID NO: 34 and TCZ q2w treatment groups return for 7 ambulatory visits planned on Weeks 0, 2, 4, 6, 8, 10, and 12. Subjects assigned to the q1w TCZ-arm return for 13 ambulatory visits planned on Weeks 0, 1, 2, 3, 4, 5, 6, 7, 8, 9, 10, 11, and 12. A follow up visit is planned 12 weeks after the last dosing.

Efficacy

The reduction of signs and symptoms of RA is evaluated by calculating the proportion of subjects achieving an ACR20 response at week 12. In addition, higher levels of response, as measured by ACR50 and ACR70 response rates, and measures of remission, using the DAS28, Clinical Disease Activity Index (CDAI), Simplified Disease Activity Index (SDAI), as well as the Boolean remission definition, is used as supportive evidence of efficacy. In addition, endpoints, including ACR responses and disease activity scores, are documented over time, including earlier time points (i.e., at Week 2 up to and including Week 10). Other RA domains, such as improvement in physical function and health-related quality of life, is evaluated using the Health Assessment Questionnaire-Disability Index (HAQ-DI), Physical and mental component scores of Short Form (SF-36) Health Survey, and Functional Assessment of Chronic Illness Therapy-Fatigue (FACIT-F).

Physician's Assessment of Tender and Swollen Joint Count

All joints listed are used in the determination of the ACR response, where 68 joints are assessed for tenderness and 66 joints are assessed for swelling.

If tenderness or swelling is noted, a "1" is entered for that joint in the appropriate field. If tenderness or swelling is absent, a "0" is entered for that joint in the appropriate field.

Duration of Morning Stiffness

The average duration of morning stiffness during the previous week in minutes is assessed. If a subject has stiffness that lasts the entire day, this is recorded as 1440 minutes of morning stiffness.

Patient's Assessment of Pain (100 mm-VAS)

Patient's assessment of pain (100 mm-VAS) is performed as part of ACR response and prior to the joint count assessments. The subject is asked, "How much pain have you had because of your condition over the past week?" and then instructed to place a mark between 0 ("no pain") and 100 mm ("pain as bad it could be") on the VAS scale to indicate how severe the pain has been.

Patient's Global Assessment of Disease Activity (100 Mmm-VASPA)

Patient's Global Assessment of Disease Activity (100 mmm-VASPA) is performed as part of ACR response, DAS28 score, SDAI, CDAI, and Boolean remission. The subject must complete the patient's global assessment independently of the physician when completing the physician global assessment.

The subject is instructed as follows: "Considering all the ways in which illness and health conditions may affect you at this time, please make a mark between 0 ("very well") and 100 mm ("very bad") on the VAS scale to show how you are doing."

Physician's Global Assessment of Disease Activity (100 mm-VASPHA)

Physician's Global Assessment of Disease Activity (100 mm-VASPHA) is performed as part of ACR response, SDAI, and CDAI. The physician must complete the physician's global assessment independently of the subject when completing the patient's global assessment. The physician makes a mark between 0 ("very good") and 100 mm ("very bad") on the VAS scale to indicate disease activity (independent of the subject's self-assessment).

C-Reactive Protein

C-reactive protein (CRP) is measured as part of ACR response, DAS28 score, SDAI, Boolean remission and EULAR Response For determining CRP concentrations in human serum, any method available in the art can be used such as e.g. the commercially available "IMMAGE® Immunochemistry Systems C-Reactive Protein (Kit Recorder #447280)" from Beckman Coulter Inc. (Brea, Calif., US). CRP concentration is to be provided in mg/L.

Erythrocyte Sedimentation Rate

Erythrocyte Sedimentation Rate (ESR) is measured as part of the DAS28 score and EULAR Response.

For determining ESR levels in serum, any method available in the art can be used such as e.g. the commercially available Greiner ESR tube or the Preanalytics—VACUETTE® Evacuated Collection Tubes (Greiner Bio-One GmbH, Kremsmuenster, Austria), the Sarstedt SEDIPLUS® 2000 (Sarstedt, Nümbrecht, Germany), or the Becton Dickinson SEDITAINER® (Becton Dickinson, Franklin Lakes, N.J., USA). The ESR concentration is to be provided in mm/h.

Health Assessment Questionnaire Disability Index

Health Assessment Questionnaire Disability Index (HAQ-DI) is performed as part of ACR response and on its own.

The HAQ-DI is a 20-question instrument which assesses the degree of difficulty the subject had in accomplishing tasks in 8 functional areas (dressing and grooming, arising, eating, walking, hygiene, reaching, gripping, and errands and chores) over the previous week. Within each category, subjects report the amount of difficulty they have in performing the specific sub-category items. There are four response options ranging from: 0=No Difficulty; 1=With Some Difficulty; 2=With Much Difficulty; 3=Unable to Do.

SF-36

The SF-36 consists of 36 items that can be summarized into 8 domains: physical functioning, role limitations due to physical health problems (role-physical), bodily pain, general health, vitality, social functioning, role limitations due to emotional problems (role-emotional), and mental health. Two summary measures, the physical component summary and the mental component summary, can be derived based on these domain scores.

The concepts measured by the SF-36 are not specific to any disease, allowing comparison of relative burden of different diseases, in addition to the relative benefit of different treatments.

FACIT-Fatigue

The FACIT Measurement System is a collection of health-related quality of life questionnaires that assess multidimensional health status in people with various chronic illnesses, including RA.

ACR20, ACR50, ACR70 Responses

ACR responses are measured according to the 2010 European League Against Rheumatism [EULAR]/American College of Rheumatology [ACR] classification criteria. ACR20/50/70 responses are defined as below:

≥20/50/70% improvement in tender/painful joint count (TJC) (68 joints) relative to baseline AND
≥20/50/70% improvement in swollen joint count (SJC) (66 joints) relative to baseline AND
≥20/50/70% improvement in 3 of the following 5 areas relative to baseline:
  Patient's Assessment of Pain (100 mm-VAS).
  Patient's Global Assessment of Disease Activity (100 mm-VASPA).
  Physician's Global Assessment of Disease Activity (100 mm-VASPHA).
  Patient's Asessment of physical function as measured by the Health Assessment Questionnaire Disability Index (HAQ-DI).
  C-reactive protein (CRP).

ACR-N Index of Improvement

The ACR-N Index of Improvement is defined as the minimum of the following 3 criteria:
  The percent improvement from baseline in tender joint counts (TJCs).
  The percent improvement from baseline in swollen joint (SJCs).
  The median percent improvement from baseline for the following 5 assessments:
    Patient's Assessment of Pain (VAS).
    Patient's Global Assessment of Disease Activity (VASPA).
    Physician's Global Assessment of Disease Activity (VASPHA).
    Patient's Assessment of physical function as measured by the HAQ-DI.
    CRP.

DAS28

The DAS28 based on erythrocyte sedimentation rate (ESR) is a statistically derived index combining TJC (28 joints), SJC (28 joints), ESR, and VASPA (Briso et al. 2008, J. Immunol., 180: 7102-7106). CRP can be used in addition to ESR in the calculation of DAS28. CRP is a more direct measure of inflammation than ESR, and it is more sensitive to short-term changes. CRP is considered at least as valid as ESR to measure RA disease activity. As such, the DAS28 using CRP is a statistically derived index combining TJC (28 joints), SJC (28 joints), CRP, and VASPA.

Cut-off points for DAS28 (ESR) to define if a subject is in clinical remission or in a state of high, moderate, or low disease activity have been defined (Betz and W. Muller 1998, Int. Immunol. 10: 1175-1184):

| High disease activity | DAS28 > 5.1 |
| Moderate disease activity | 3.2 < DAS28 ≤ 5.1 |
| Low disease activity | 2.6 ≤ DAS28 ≤ 3.2 |
| Remission | DAS28 < 2.6 |

EULAR response is assessed by comparing a subject's DAS28 score (using CRP and ESR) relative to baseline as follows.

| | Improvement in DAS28 Relative to Baseline | | |
|---|---|---|---|
| Present DAS28 | >1.2 | >0.6 and ≤1.2 | ≤0.6 |
| ≤3.2 | good response | moderate response | no response |
| >3.2 and ≤5.1 | moderate response | moderate response | no response |
| >5.1 | moderate response | no response | no response |

Disease Activity

For measurement of the disease activity, the Disease Activity Score is determined using 28 joint counts (DAS28 using CRP and erythrocyte sedimentation rate [ESR]). In addition, the Simplified Disease Activity Index (SDAI) and Clinical Disease Activity Index (CDAI) is determined.

The CDAI clinical score is determined according to following criteria (Felson, et al. 2011; Aletaha and Smolen 2007, Clinical rheumatology 21: 663-75):

Calculation of CDAI Score: CDAI=TJC28+SJC28+VASPA+VASPHA

Classification of CDAI Score:

| CDAI Score | CDAI ≤ 2.8 | 2.8 < CDAI ≤ 10 | 10 < CDAI ≤ 22 | 22 < CDAI |
|---|---|---|---|---|
| Disease Activity | remission | low disease activity | moderate disease activity | high disease activity |

The SDAI clinical score is determined according to following criteria (Aletaha and Smolen 2007):

Calculation of SDAI Score: SDAI=TJC28+SJC28+VASPA+VASPHA+CRP

Classification of SDAI Score:

| SDAI Score | SDAI ≤ 3.3 | 3.3 < SDAI ≤ 11.0 | 11.1 < SDAI ≤ 26.0 | SDAI > 26.0 |
|---|---|---|---|---|
| Disease Activity | remission | low disease activity | moderate disease activity | high disease activity |

Remission

Remission is determined using disease remission parameters: DAS28, Simplified Disease Activity Index (SDAI), Clinical Disease Activity Index (CDAI), Boolean.

Boolean remission is determined according to following criteria (Felson et al. 2011, American College of Rheumatology/European League against Rheumatism provisional definition of remission in rheumatoid arthritis for clinical trials. Annals of the rheumatic diseases 70: 404-13):

If TJC28≤1 and SJC28≤1 and VASPA (cm)≤1 and CRP (mg/dL)≤1
Then remission="yes"
Else remission="no"

Pharmacokinetics

Blood samples are taken for analysis of SEQ ID NO: 34 in serum at 2, 4, 6, 8, 10, and 12 weeks after dosing. The determination of total active SEQ ID NO: 34 concentrations in human serum samples is performed using a validated enzyme-linked immunosorbent assay (ELISA) similar as described in Example 1.

Pharmacodynamics

The pharmacodynamics of SEQ ID NO: 34 is assessed by measurement of the total soluble interleukin-6 receptor (sIL-6R) in blood samples.

For determining plasma sIL-6R concentrations, blood samples are taken at baseline, 2, 4, 6, 10, and 12 weeks after dosing. The analysis of total sIL-6R in plasma is performed using a validated ELISA method as described in Example 1.

Safety

Safety and tolerability assessments include evaluation of (serious) AEs and injection site reactions, laboratory assessment, urinalysis, ECG, vital signs, and physical examination. To assess immunogenicity, the presence of ADA is measured in serum until the follow-up visit.

Tables

TABLE A-1

Protein sequences of improved Nanobodies (with FR and CDR sequences indicated)

| Nanobody | SEQ ID | FR1 | SEQ ID | CDR 1 | SEQ ID | FR2 | SEQ ID | CD 2 | SEQ ID | FR3 | SEQ ID | CDR 3 | SEQ ID | FR4 | SEQ ID |
|---|---|---|---|---|---|---|---|---|---|---|---|---|---|---|---|
| PMP7F4 | 7 | EVQLVESGGGLVQPGGSLRLSCAASGTTFK | 11 | VNVMA | 18 | WYRQAPGKGRELVA | 20 | GIINGGSTTYADSVKG | 27 | RFTISRDNAKNTLYLQMNSLRPEDTAVYYCAF | 29 | VTTNSDYDLGRDY | 32 | WGQGTLVTVSS | 33 |
| PMP7C4 | 2 | EVQLVESGGGLVQPGGSLRLSCAASGTTFR | 12 | INVMA | 18 | WYRQAPGKGRELVA | 20 | GIITNGSTSYADSVKG | 22 | RFTISRDNAKNTLYLQMNSLRPEDTAVYYCAF | 29 | VTTNSDYDLGRDY | 32 | WGQGTLVTVSS | 33 |
| PMP7D6 | 3 | EVQLVESGGGLVQPGGSLRLSCAASGSIFR | 13 | VNVMA | 18 | WYRQAPGKGRELVA | 20 | AVINGGTTTYADSVKG | 23 | RFTISRDNAKNTLYLQMNSLRPEDTAVYYCAF | 29 | VTTNSDYDLGRDY | 32 | WGQGTLVTVSS | 33 |
| PMP7G7 | 4 | EVQLVESGGGLVQPGGSLRLSCAASGTTFK | 11 | INIMA | 19 | WYRQAPGKGRELVA | 20 | GVITGGNTTYADSVKG | 24 | RFTISRDNAKNTLYLQMNSLRPEDTAVYYCAF | 29 | VTTNSDYDLGRDY | 32 | WGQGTLVTVSS | 33 |
| PMP7G8 | 5 | EVQLVESGGGLVQPGGSLRLSCAASGSTFR | 14 | INVMA | 17 | WYRQAPGKGRELVA | 20 | GVINDGSTTYADSVKG | 25 | RFTISRDNAKNTLYLQMNSLRPEDTAVYYCAF | 29 | VTTNSDYDLGRDY | 32 | WGQGTLVTVSS | 33 |
| PMP20F6 | 6 | EVQLVESGGGLVQPGGSLRLSCAASGSVFK | 15 | INVMA | 17 | WYRQAPGKGRELVA | 20 | GIVSGGSTSYADSVKG | 26 | RFTISRDNAKNTLYLQMNSLRPEDTAVYYCAF | 29 | ITTNSDYDLGRRY | 31 | WGQGTLVTVSS | 33 |

TABLE A-1-continued

Protein sequences of improved Nanobodies (with FR and CDR sequences indicated)

| Nanobody | SEQ ID | FR1 | SEQ ID | CDR 1 | SEQ ID | FR2 | SEQ ID | CD 2 | SEQ ID | FR3 | SEQ ID | CDR 3 | SEQ ID | FR4 | SEQ ID |
|---|---|---|---|---|---|---|---|---|---|---|---|---|---|---|---|
| PMP20A11 | 1 | EVQLVESGGGLVQPGGSLRLSCAASGSVFK | 15 | INVMA | 17 | WYRQAPGKGRELVA | 20 | GIISGGSTSYADSVKG | 21 | RFTISRDNAKNTLYLQMNSLRPEDTAVYYCAF | 29 | ITTESDYDLGRRY | 30 | WGQGTLVTVSS | 33 |
| PMP20E10 | 8 | EVQLVESGGGLVQPGGSLRLSCAASGSVFK | 15 | INVMA | 17 | WYRQAPGKGRELVA | 20 | GIVSGGSTSYADSVKG | 26 | RFTISRDNAKNTLYLQMNSLRPEDTAVYYCAF | 29 | ITTESDYDLGRRY | 30 | WGQGTLVTVSS | 33 |
| PMP21A10 | 9 | EVQLVESGGGLVQPGGSLRLSCAASGSIFK | 16 | INVMA | 17 | WYRQAPGKGRELVA | 20 | GIVTGGSTSYADSVKG | 28 | RFTISRDNAKNTLYLQMNSLRPEDTAVYYCAF | 29 | ITTESDYDLGRRY | 30 | WGQGTLVTVSS | 33 |
| PMP21D11 | 10 | EVQLVESGGGLVQPGGSLRLSCAASGSVFK | 15 | INVMA | 17 | WYRQAPGKGRELVA | 20 | GIVTGGSTSYADSVKG | 28 | RFTISRDNAKNTLYLQMNSLRPEDTAVYYCAF | 29 | ITTESDYDLGRRY | 30 | WGQGTLVTVSS | 33 |

TABLE A-2

Protein sequences of improved Nanobodies

PMP7F4, SEQ ID NO: 7

EVQLVESGGGLVQPGGSLRLSCAASGTTFKVNVMAWYRQAPGKGRELVAG
IINGGSTTYADSVKGRFTISRDNAKNTLYLQMNSLRPEDTAVYYCAFVTT
NSDYDLGRDYWGQGTLVTVSS

PMP7C4, SEQ ID NO: 2

EVQLVESGGGLVQPGGSLRLSCAASGTTFRINVMAWYRQAPGKGRELVAG
IITNGSTSYADSVKGRFTISRDNAKNTLYLQMNSLRPEDTAVYYCAFVTT
NSDYDLGRDYWGQGTLVTVSS

PMP7D6, SEQ ID NO: 3

EVQLVESGGGLVQPGGSLRLSCAASGSIFRVNVMAWYRQAPGKGRELVAA
VINGGTTTYADSVKGRFTISRDNAKNTLYLQMNSLRPEDTAVYYCAFVTT
NSDYDLGRDYWGQGTLVTVSS

PMP7G7, SEQ ID NO: 4

EVQLVESGGGLVQPGGSLRLSCAASGTTFKINIMAWYRQAPGKGRELVAG
VITGGNTTYADSVKGRFTISRDNAKNTLYLQMNSLRPEDTAVYYCAFVTT
NSDYDLGRDYWGQGTLVTVSS

PMP7G8, SEQ ID NO: 5

EVQLVESGGGLVQPGGSLRLSCAASGSTFRINVMAWYRQAPGKGRELVAG
VINDGSTTYADSVKGRFTISRDNAKNTLYLQMNSLRPEDTAVYYCAFVTT
NSDYDLGRDYWGQGTLVTVSS

PMP20F6, SEQ ID NO: 6

EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
NSDYDLGRRYWGQGTLVTVSS

PMP20A11, IL6R300, SEQ ID NO: 1

EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSS

PMP20E10, SEQ ID NO: 8

EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
ESDYDLGRRYWGQGTLVTVSS

PMP21A10, SEQ ID NO: 9

EVQLVESGGGLVQPGGSLRLSCAASGSIFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

PMP21D11, SEQ ID NO: 10

EVQLVESGGGLVQPGGSLRLSCAASGSVFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

TABLE A-3

Protein sequences of preferred polypeptides of the invention

IL6R304, SEQ ID NO: 34

EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSS

IL6R305, SEQ ID NO: 35

EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGGSLRL
SCAASGSVFKINVMAWYRQAPGKGRELVAGIISGGSTSYADSVKGRFTIS
RDNAKNTLYLQMNSLRPEDTAVYYCAFITTESDYDLGRRYWGQGTLVTVS
SGGGGSGGGSEVQLVESGGGLVQPGNSLRLSCAASGFTFSSFGMSWVRQA
PGKGLEWVSSISGSGSDTLYADSVKGRFTISRDNAKTTLYLQMNSLRPED
TAVYYCTIGGSLSRSSQGTLVTVSS

IL6R306, SEQ ID NO: 36

EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSSGGGGS
GGGSEVQLVESGGGLVQPGGSLRLSCAASGSVFKINVMAWYRQAPGKGRE

TABLE A-3-continued

Protein sequences of preferred polypeptides of the invention

LVAGIISGGSTSYADSVKGRFTISRDNAKNTLYLQMNSLRPEDTAVYYCA
FITTESDYDLGRRYWGQGTLVTVSS

TABLE A-4

Preferred, but non-limiting examples of albumin-binding Nanobodies

ALB-1, SEQ ID NO: 37

AVQLVESGGGLVQPGNSLRLSCAASGFTFRSFGMSWVRQAPGKEPEWVSS
ISGSGSDTLYADSVKGRFTISRDNAKTTLYLQMNSLKPEDTAVYYCTIGG
SLSRSSQGTQVTVSS

ALB-8 (humanized ALB-1), SEQ ID NO: 38

EVQLVESGGGLVQPGNSLRLSCAASGFTFSSFGMSWVRQAPGKGLEWVSS
ISGSGSDTLYADSVKGRFTISRDNAKTTLYLQMNSLRPEDTAVYYCTIGG
SLSRSSQGTLVTVSS

ALB-2, SEQ ID NO: 39

AVQLVESGGGLVQGGGSLRLACAASERIFDLNLMGWYRQGPGNERELVAT
CITVGDSTNYADSVKGRFTISMDYTKQTVYLHMNSLRPEDTGLYYCKIRR
TWHSELWGQGTQVTVSS

TABLE A-5

Sequence listing of linkers

| Linker | SEQ ID NO: | Sequences |
| --- | --- | --- |
| 5GS | 40 | GGGGS |
| 7GS | 41 | SGGSGGS |
| GS8 | 42 | GGGGSGGGS |
| 9GS | 43 | GGGGSGGGS |
| 10GS | 44 | GGGGSGGGGS |
| 15GS | 45 | GGGGSGGGGSGGGGS |
| 18GS | 46 | GGGGSGGGGSGGGGGGS |
| 20GS | 47 | GGGGSGGGGSGGGGSGGGGS |
| 25GS | 48 | GGGGSGGGGSGGGGSGGGGSGGGGS |
| 30GS | 49 | GGGGSGGGGSGGGGSGGGGSGGGGSGGGGS |
| 35GS | 50 | GGGGSGGGGSGGGGSGGGGSGGGGSGGGGSGGGGS |
| G1 hinge | 51 | EPKSCDKTHTCPPCP |
| 9GS-G1 hinge | 52 | GGGGSGGGSEPKSCDKTHTCPPCP |
| Llama upper long hinge region | 53 | EPKTPKPQPAAA |
| G3 hinge | 54 | ELKTPLGDTTHTCPRCPEPKSCDTPPPCPRCPEPKSCDTPPPCPRCPEPKSCDTPPPCPRCP |
| Ala | 55 | AAA |

---

The invention claimed is:

1. A pre-filled syringe containing 0.5-1 ml of a pharmaceutical composition comprising a polypeptide comprising, consisting essentially of, or consisting of an immunoglobulin single variable domain that binds interleukin-6 receptor LIL-6R), that is at a concentration of 150 mg/ml, and that comprises a CDR1 comprising the amino acid sequence of SEQ ID NO: 17, a CDR2 comprising the amino acid sequence of SEQ ID NO: 21, and a CDR3 comprising the amino acid sequence of SEQ ID NO: 30.

2. The pre-filled syringe according to claim 1, wherein the immunoglobulin single variable domain that binds IL-6R has the amino acid sequence of SEQ ID NO: 1.

3. The pre-filled syringe according to claim 1, wherein the polypeptide additionally comprises an immunoglobulin single variable domain that binds human serum albumin.

4. The pre-filled syringe according to claim 3, wherein the immunoglobulin single variable domain that binds human serum albumin has the amino acid sequence of SEQ ID NO: 38.

5. The pre-filled syringe according to claim 1, wherein the polypeptide has the amino acid sequence of SEQ ID NO: 34.

6. The pre-filled syringe according to claim 1, wherein the pharmaceutical composition further comprises a disease-modifying antirheumatic drug (DMARD), a nonsteroidal anti-inflammatory drug (NSAID), a corticosteroid, an additional biological therapeutic, or a combination thereof.

7. The pre-filled syringe according to claim 6, wherein the DMARD is methotrexate.

* * * * *

UNITED STATES PATENT AND TRADEMARK OFFICE
CERTIFICATE OF CORRECTION

PATENT NO. : 11,008,393 B2
APPLICATION NO. : 16/143580
DATED : May 18, 2021
INVENTOR(S) : Sven Hoefman et al.

Page 1 of 1

It is certified that error appears in the above-identified patent and that said Letters Patent is hereby corrected as shown below:

In the Claims

Claim 1, beginning at Column 93, Line 13, should read:
1. A pre-filled syringe containing 0.5-1ml of a pharmaceutical composition comprising a polypeptide comprising, consisting essentially of, or consisting of an immunoglobulin single variable domain that binds interleukin-6 receptor (IL-6R), that is at a concentration of 150 mg/ml, and that comprises a CDR1 comprising the amino acid sequence of SEQ ID NO: 17, a CDR2 comprising the amino acid sequence of SEQ ID NO: 21, and a CDR3 comprising the amino acid sequence of SEQ ID NO: 30.

Signed and Sealed this
Tenth Day of August, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 55

<210> SEQ ID NO 1
<211> LENGTH: 121
<212> TYPE: PRT
<213> ORGANISM: Artificial Sequence
<220> FEATURE:
<223> OTHER INFORMATION: Nanobody

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95
```

```
Phe Ile Thr Thr Glu Ser Asp Tyr Asp Leu Gly Arg Arg Tyr Trp Gly
            100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Nanobody

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Nanobody

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Val Met Ala Trp Tyr Arg Gln Ala Pro Gly Lys Gly Arg Glu Leu Val
        35                  40                  45

Ala Ala Val Ile Asn Gly Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
```

```
<213> ORGANISM: Artificial Sequence
<220> FEATURE:
<223> OTHER INFORMATION: Nanobody

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Thr Thr Phe Lys Ile Asn
             20                  25                  30

Ile Met Ala Trp Tyr Arg Gln Ala Pro Gly Lys Gly Arg Glu Leu Val
         35                  40                  45

Ala Gly Val Ile Thr Gly Gly Asn Thr Thr Tyr Ala Asp Ser Val Lys
     50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Nanobody

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Phe Arg Ile Asn
             20                  25                  30

Val Met Ala Trp Tyr Arg Gln Ala Pro Gly Lys Gly Arg Glu Leu Val
         35                  40                  45

Ala Gly Val Ile Asn Asp Gly Ser Thr Thr Tyr Ala Asp Ser Val Lys
     50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Nanobody

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val Phe Lys Ile Asn
             20                  25                  30
```

-continued

Val Met Ala Trp Tyr Arg Gln Ala Pro Gly Lys Gly Arg Glu Leu Val
            35                  40                  45

Ala Gly Ile Val Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Asn Ser Asp Tyr Asp Leu Gly Arg Arg Tyr Trp Gly
            100                 105                 110

Gln Gly Thr Leu Val Thr Val Ser Ser
            115                 120

<210> SEQ ID NO 7
<211> LENGTH: 121
<212> TYPE: PRT
<213> ORGANISM: Artificial Sequence
<220> FEATURE:
<223> OTHER INFORMATION: Nanobody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Val Asn
            20                  25                  30

Val Met Ala Trp Tyr Arg Gln Ala Pro Gly Lys Gly Arg Glu Leu Val
            35                  40                  45

Ala Gly Ile Ile Asn Gly Gly Ser Thr Thr Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: Nanobody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala

```
                    85                  90                  95
Phe Ile Thr Thr Glu Ser Asp Tyr Asp Leu Gly Arg Arg Tyr Trp Gly
                100                 105                 110
Gln Gly Thr Leu Val Thr Val Ser Ser
        115                 120
```

<210> SEQ ID NO 9
<211> LENGTH: 121
<212> TYPE: PRT
<213> ORGANISM: Artificial Sequence
<220> FEATURE:
<223> OTHER INFORMATION: Nanobody

<400> SEQUENCE: 9

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Lys Ile Asn
            20                  25                  30
Val Met Ala Trp Tyr Arg Gln Ala Pro Gly Lys Gly Arg Glu Leu Val
        35                  40                  45
Ala Gly Ile Val Thr Gly Gly Ser Thr Ser Tyr Ala Asp Ser Val Lys
    50                  55                  60
Gly Arg Phe Thr Ile Ser Arg Asp Asn Ala Lys Asn Thr Leu Tyr Leu
65                  70                  75                  80
Gln Met Asn Ser Leu Arg Pro Glu Asp Thr Ala Val Tyr Tyr Cys Ala
                85                  90                  95
Phe Ile Thr Thr Glu Ser Asp Tyr Asp Leu Gly Arg Arg Tyr Trp Gly
                100                 105                 110
Gln Gly Thr Leu Val Thr Val Ser Ser
        115                 120
```

<210> SEQ ID NO 10
<211> LENGTH: 121
<212> TYPE: PRT
<213> ORGANISM: Artificial Sequence
<220> FEATURE:
<223> OTHER INFORMATION: Nanobody

<400> SEQUENCE: 10

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Val Phe Lys Ile Asn
            20                  25                  30
Val Met Ala Trp Tyr Arg Gln Ala Pro Gly Lys Gly Arg Glu Leu Val
        35                  40                  45
Ala Gly Ile Val Thr Gly Gly Ser Thr Ser Tyr Ala Asp Ser Val Lys
    50                  55                  60
Gly Arg Phe Thr Ile Ser Arg Asp Asn Ala Lys Asn Thr Leu Tyr Leu
65                  70                  75                  80
Gln Met Asn Ser Leu Arg Pro Glu Asp Thr Ala Val Tyr Tyr Cys Ala
                85                  90                  95
Phe Ile Thr Thr Glu Ser Asp Tyr Asp Leu Gly Arg Arg Tyr Trp Gly
                100                 105                 110
Gln Gly Thr Leu Val Thr Val Ser Ser
        115                 120
```

<210> SEQ ID NO 11
<211> LENGTH: 30

<212> TYPE: PRT
<213> ORGANISM: Artificial Sequence
<220> FEATURE:
<223> OTHER INFORMATION: Framework sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Framework sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Framework sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Framework sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Framework sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys
            20                  25                  30

<210> SEQ ID NO 16

```
<211> LENGTH: 30
<212> TYPE: PRT
<213> ORGANISM: Artificial Sequence
<220> FEATURE:
<223> OTHER INFORMATION: Framework sequence

<400> SEQUENCE: 16

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Lys
            20                  25                  30

<210> SEQ ID NO 17
<211> LENGTH: 5
<212> TYPE: PRT
<213> ORGANISM: Artificial Sequence
<220> FEATURE:
<223> OTHER INFORMATION: CDR sequence

<400> SEQUENCE: 17

Ile Asn Val Met Ala
1               5

<210> SEQ ID NO 18
<211> LENGTH: 5
<212> TYPE: PRT
<213> ORGANISM: Artificial Sequence
<220> FEATURE:
<223> OTHER INFORMATION: CDR sequence

<400> SEQUENCE: 18

Val Asn Val Met Ala
1               5

<210> SEQ ID NO 19
<211> LENGTH: 5
<212> TYPE: PRT
<213> ORGANISM: Artificial Sequence
<220> FEATURE:
<223> OTHER INFORMATION: CDR sequence

<400> SEQUENCE: 19

Ile Asn Ile Met Ala
1               5

<210> SEQ ID NO 20
<211> LENGTH: 14
<212> TYPE: PRT
<213> ORGANISM: Artificial Sequence
<220> FEATURE:
<223> OTHER INFORMATION: Framework sequence

<400> SEQUENCE: 20

Trp Tyr Arg Gln Ala Pro Gly Lys Gly Arg Glu Leu Val Ala
1               5                   10

<210> SEQ ID NO 21
<211> LENGTH: 16
<212> TYPE: PRT
<213> ORGANISM: Artificial Sequence
<220> FEATURE:
<223> OTHER INFORMATION: CDR sequence

<400> SEQUENCE: 21

Gly Ile Ile Ser Gly Gly Ser Thr Ser Tyr Ala Asp Ser Val Lys Gly
1               5                   10                  15
```

<210> SEQ ID NO 22
<211> LENGTH: 16
<212> TYPE: PRT
<213> ORGANISM: Artificial Sequence
<220> FEATURE:
<223> OTHER INFORMATION: CDR sequence

<400> SEQUENCE: 22

Gly Ile Ile Thr Asn Gly Ser Thr Ser Tyr Ala Asp Ser Val Lys Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: CDR sequence

<400> SEQUENCE: 23

Ala Val Ile Asn Gly Gly Thr Thr Thr Tyr Ala Asp Ser Val Lys Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: CDR sequence

<400> SEQUENCE: 24

Gly Val Ile Thr Gly Gly Asn Thr Thr Tyr Ala Asp Ser Val Lys Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: CDR sequence

<400> SEQUENCE: 25

Gly Val Ile Asn Asp Gly Ser Thr Thr Tyr Ala Asp Ser Val Lys Gly
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: CDR sequence

<400> SEQUENCE: 26

Gly Ile Val Ser Gly Gly Ser Thr Ser Tyr Ala Asp Ser Val Lys Gly
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: CDR sequence

<400> SEQUENCE: 27

Gly Ile Ile Asn Gly Gly Ser Thr Thr Tyr Ala Asp Ser Val Lys Gly
1               5                   10                  15

```
<210> SEQ ID NO 28
<211> LENGTH: 16
<212> TYPE: PRT
<213> ORGANISM: Artificial Sequence
<220> FEATURE:
<223> OTHER INFORMATION: CDR sequence

<400> SEQUENCE: 28

Gly Ile Val Thr Gly Gly Ser Thr Ser Tyr Ala Asp Ser Val Lys Gly
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Framework sequence

<400> SEQUENCE: 29

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Phe
            20                  25                  30

<210> SEQ ID NO 30
<211> LENGTH: 13
<212> TYPE: PRT
<213> ORGANISM: Artificial Sequence
<220> FEATURE:
<223> OTHER INFORMATION: CDR sequence

<400> SEQUENCE: 30

Ile Thr Thr Glu Ser Asp Tyr Asp Leu Gly Arg Arg Tyr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: CDR sequence

<400> SEQUENCE: 31

Ile Thr Thr Asn Ser Asp Tyr Asp Leu Gly Arg Arg Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: CDR sequence

<400> SEQUENCE: 32

Val Thr Thr Asn Ser Asp Tyr Asp Leu Gly Arg Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Framework sequence

<400> SEQUENCE: 33

Trp Gly Gln Gly Thr Leu Val Thr Val Ser Ser
1               5                   10
```

<210> SEQ ID NO 34
<211> LENGTH: 245
<212> TYPE: PRT
<213> ORGANISM: Artificial Sequence
<220> FEATURE:
<223> OTHER INFORMATION: Nanobody

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245
```

<210> SEQ ID NO 35
<211> LENGTH: 375
<212> TYPE: PRT
<213> ORGANISM: Artificial Sequence
<220> FEATURE:
<223> OTHER INFORMATION: Nanobody

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
```

```
                50                  55                  60
Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                     85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Gly Leu Val Gln Pro
        130                 135                 140

Gly Gly Ser Leu Arg Leu Ser Cys Ala Ala Ser Gly Ser Val Phe Lys
145                 150                 155                 160

Ile Asn Val Met Ala Trp Tyr Arg Gln Ala Pro Gly Lys Gly Arg Glu
                165                 170                 175

Leu Val Ala Gly Ile Ile Ser Gly Gly Ser Thr Ser Tyr Ala Asp Ser
                180                 185                 190

Val Lys Gly Arg Phe Thr Ile Ser Arg Asp Asn Ala Lys Asn Thr Leu
            195                 200                 205

Tyr Leu Gln Met Asn Ser Leu Arg Pro Glu Asp Thr Ala Val Tyr Tyr
    210                 215                 220

Cys Ala Phe Ile Thr Thr Glu Ser Asp Tyr Asp Leu Gly Arg Arg Tyr
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Asn Ser Leu Arg Leu Ser Cys Ala Ala Ser Gly Phe Thr
        275                 280                 285

Phe Ser Ser Phe Gly Met Ser Trp Val Arg Gln Ala Pro Gly Lys Gly
    290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser
    370                 375

<210> SEQ ID NO 36
<211> LENGTH: 375
<212> TYPE: PRT
<213> ORGANISM: Artificial Sequence
<220> FEATURE:
<223> OTHER INFORMATION: Nanobody

<400> SEQUENCE: 36

Glu Val Gln Leu Val Glu Ser Gly Gly Gly Leu Val Gln Pro Gly Gly
 1                   5                  10                  15

Ser Leu Arg Leu Ser Cys Ala Ala Ser Gly Ser Val Phe Lys Ile Asn
                20                  25                  30

Val Met Ala Trp Tyr Arg Gln Ala Pro Gly Lys Gly Arg Glu Leu Val
```

```
            35                  40                  45
Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Arg Leu Ser Cys Ala Ala Ser Gly Ser Val Phe Lys Ile Asn Val Met
        275                 280                 285

Ala Trp Tyr Arg Gln Ala Pro Gly Lys Gly Arg Glu Leu Val Ala Gly
    290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
                325                 330                 335

Asn Ser Leu Arg Pro Glu Asp Thr Ala Val Tyr Tyr Cys Ala Phe Ile
            340                 345                 350

Thr Thr Glu Ser Asp Tyr Asp Leu Gly Arg Arg Tyr Trp Gly Gln Gly
        355                 360                 365

Thr Leu Val Thr Val Ser Ser
    370                 375

<210> SEQ ID NO 37
<211> LENGTH: 115
<212> TYPE: PRT
<213> ORGANISM: Artificial Sequence
<220> FEATURE:
<223> OTHER INFORMATION: Nanobody

<400> SEQUENCE: 37

Ala Val Gln Leu Val Glu Ser Gly Gly Gly Leu Val Gln Pro Gly Asn
1               5                  10                  15

Ser Leu Arg Leu Ser Cys Ala Ala Ser Gly Phe Thr Phe Arg Ser Phe
```

```
                20                  25                  30
Gly Met Ser Trp Val Arg Gln Ala Pro Gly Lys Glu Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: Nanobody

<400> SEQUENCE: 38

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: Nanobody

<400> SEQUENCE: 39

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
                20                  25                  30

Leu Met Gly Trp Tyr Arg Gln Gly Pro Gly Asn Glu Arg Glu Leu Val
            35                  40                  45

Ala Thr Cys Ile Thr Val Gly Asp Ser Thr Asn Tyr Ala Asp Ser Val
        50                  55                  60

Lys Gly Arg Phe Thr Ile Ser Met Asp Tyr Thr Lys Gln Thr Val Tyr
65                  70                  75                  80
```

Leu His Met Asn Ser Leu Arg Pro Glu Asp Thr Gly Leu Tyr Tyr Cys
            85                  90                  95

Lys Ile Arg Arg Thr Trp His Ser Glu Leu Trp Gly Gln Gly Thr Gln
        100                 105                 110

Val Thr Val Ser Ser
        115

<210> SEQ ID NO 40
<211> LENGTH: 5
<212> TYPE: PRT
<213> ORGANISM: Artificial Sequence
<220> FEATURE:
<223> OTHER INFORMATION: Linker sequence

<400> SEQUENCE: 40

Gly Gly Gly Gly Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Linker sequence

<400> SEQUENCE: 41

Ser Gly Gly Ser Gly Gly Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Linker sequence

<400> SEQUENCE: 42

Gly Gly Gly Gly Ser Gly Gly Gly Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Linker sequence

<400> SEQUENCE: 43

Gly Gly Gly Gly Ser Gly Gly Gly Ser
1               5

<210> SEQ ID NO 44
<211> LENGTH: 10
<212> TYPE: PRT
<213> ORGANISM: Artificial Sequence
<220> FEATURE:
<223> OTHER INFORMATION: Linker sequence

<400> SEQUENCE: 44

Gly Gly Gly Gly Ser Gly Gly Gly Gly Ser
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Linker sequence

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: Linker sequence

<400> SEQUENCE: 46

Gly Gly Gly Gly Ser Gly Gly Gly Gly Ser Gly Gly Gly Gly Gly
1               5                   10                  15

Gly Ser

<210> SEQ ID NO 47
<211> LENGTH: 20
<212> TYPE: PRT
<213> ORGANISM: Artificial Sequence
<220> FEATURE:
<223> OTHER INFORMATION: Linker sequence

<400> SEQUENCE: 47

Gly Gly Gly Gly Ser Gly Gly Gly Gly Ser Gly Gly Gly Gly Ser Gly
1               5                   10                  15

Gly Gly Gly Ser
            20

<210> SEQ ID NO 48
<211> LENGTH: 25
<212> TYPE: PRT
<213> ORGANISM: Artificial Sequence
<220> FEATURE:
<223> OTHER INFORMATION: Linker sequence

<400> SEQUENCE: 48

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 49
<211> LENGTH: 30
<212> TYPE: PRT
<213> ORGANISM: Artificial Sequence
<220> FEATURE:
<223> OTHER INFORMATION: Linker sequence

<400> SEQUENCE: 49

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 50
<211> LENGTH: 35
<212> TYPE: PRT
<213> ORGANISM: Artificial Sequence
<220> FEATURE:
<223> OTHER INFORMATION: Linker sequence

```
<400> SEQUENCE: 50

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 51
<211> LENGTH: 15
<212> TYPE: PRT
<213> ORGANISM: Artificial Sequence
<220> FEATURE:
<223> OTHER INFORMATION: Linker sequence

<400> SEQUENCE: 51

Glu Pro Lys Ser Cys Asp Lys Thr His Thr Cys Pro Pro Cys Pro
1               5                   10                  15

<210> SEQ ID NO 52
<211> LENGTH: 24
<212> TYPE: PRT
<213> ORGANISM: Artificial Sequence
<220> FEATURE:
<223> OTHER INFORMATION: Linker sequence

<400> SEQUENCE: 52

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 53
<211> LENGTH: 12
<212> TYPE: PRT
<213> ORGANISM: Artificial Sequence
<220> FEATURE:
<223> OTHER INFORMATION: Linker sequence

<400> SEQUENCE: 53

Glu Pro Lys Thr Pro Lys Pro Gln Pro Ala Ala Ala
1               5                   10

<210> SEQ ID NO 54
<211> LENGTH: 62
<212> TYPE: PRT
<213> ORGANISM: Artificial Sequence
<220> FEATURE:
<223> OTHER INFORMATION: Linker sequence

<400> SEQUENCE: 54

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60

<210> SEQ ID NO 55
<211> LENGTH: 3
<212> TYPE: PRT
```

```
<213> ORGANISM: Artificial Sequence
<220> FEATURE:
<223> OTHER INFORMATION: Linker sequence

<400> SEQUENCE: 55

Ala Ala Ala
1
```